United States Patent
Walters et al.

(10) Patent No.: US 6,653,114 B2
(45) Date of Patent: Nov. 25, 2003

(54) METHOD AND APPARATUS FOR TREATING MATERIALS WITH ELECTRICAL FIELDS HAVING VARYING ORIENTATIONS

(76) Inventors: Richard E. Walters, 6248 Wild Swan Way, Columbia, MD (US) 21045; Alan D. King, 405 Lincoln Ave., Takoma Park, MD (US) 20912; Derin C. Walters, 11931 Meadowfire Dr., Austin, TX (US) 78758-3321

(*) Notice: Subject to any disclaimer, the term of this patent is extended or adjusted under 35 U.S.C. 154(b) by 0 days.

(21) Appl. No.: 10/265,133

(22) Filed: Oct. 7, 2002

(65) Prior Publication Data

US 2003/0159943 A2 Aug. 28, 2003

Related U.S. Application Data

(60) Continuation of application No. 09/637,380, filed on Aug. 15, 2000, now abandoned, which is a division of application No. 09/242,174, filed as application No. PCT/US97/09300 on Jun. 10, 1997, now Pat. No. 6,117,660.

(51) Int. Cl.[7] .............................................. C12N 13/00
(52) U.S. Cl. ................. 435/173.6; 435/173.4; 435/173.5; 205/701
(58) Field of Search ....................... 205/701; 435/173.6, 435/173.4, 173.5, 173.1

(56) References Cited

U.S. PATENT DOCUMENTS 6,010,613 A  *  1/2000  Walters et al. .............. 205/701

OTHER PUBLICATIONS

"Electrochemotherapy: Transition from Laboratory to the Clinic", by Gunter A. Hofmann, Sukhendu B. Dev, and Gurvinder S. Nanda, in IEEE Engineering in Medicine and Biology, Nov./Dec. 1996, pp. 124–132.

* cited by examiner

Primary Examiner—James J. Seidleck
Assistant Examiner—Thao Tran
(74) Attorney, Agent, or Firm—Marvin S. Towsend

(57) ABSTRACT

The object of the invention is to provide a method and apparatus for treating membrane-containing material with electrical fields, in vitro, and with an added treating substance. With the method, a plurality of electrodes are arrayed around the material to be treated and are connected to outputs of an electrode selection apparatus. Inputs of the electrode selection apparatus are connected to outputs of a pulse sequence generator. A treating substance is added to the membrane-containing material. Electrical pulses are applied to the electrode selection apparatus and are routed through the electrode selection apparatus in a predetermined, computer-controlled sequence to selected electrodes in the array of electrodes, whereby the membrane-containing material is treated with the added treating substance and with electrical fields. The routing of applied pulses through the electrode selection apparatus to selected electrodes can be done in an enormous number of ways.

10 Claims, 36 Drawing Sheets

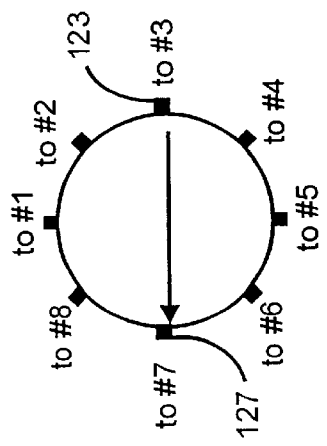
FIG. 10C
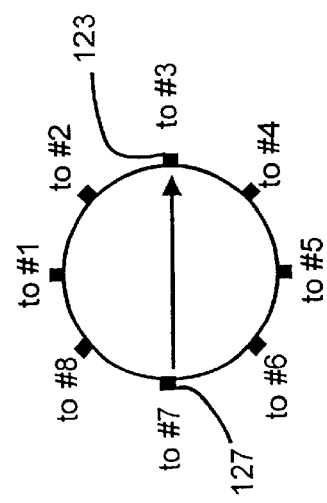
FIG. 10F
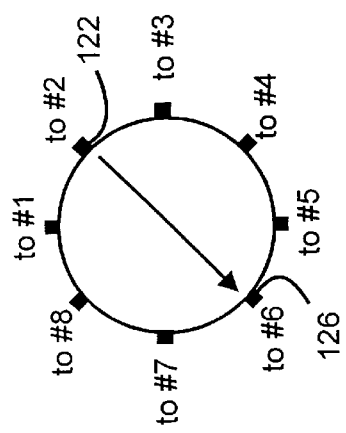
FIG. 10B
FIG. 10E
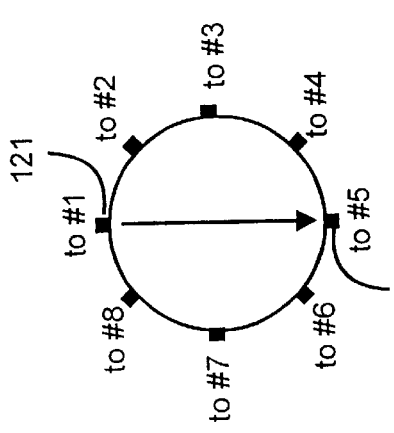
FIG. 10A
FIG. 10D

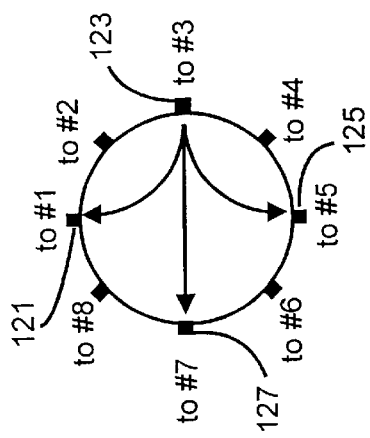
FIG. 11A
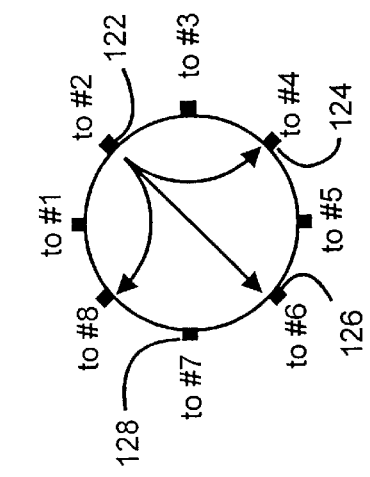
FIG. 11B
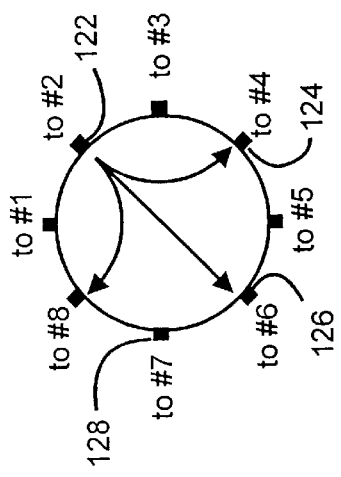
FIG. 11C
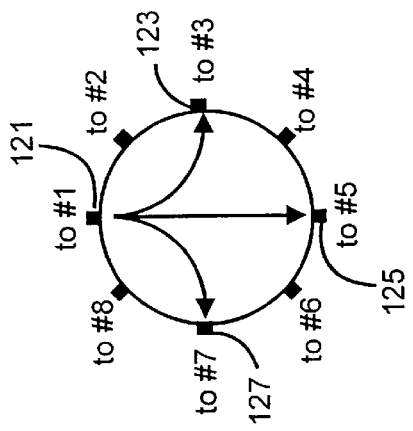
FIG. 11D
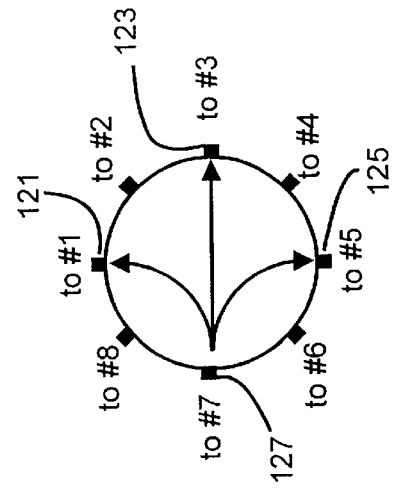
FIG. 11E
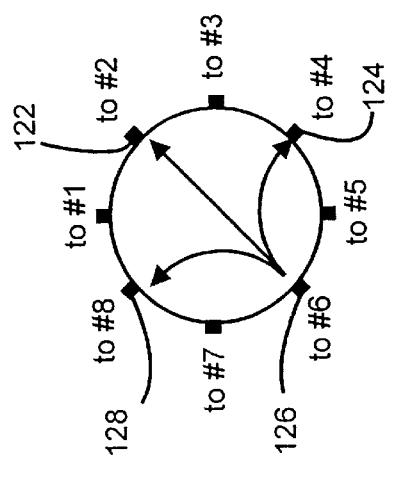
FIG. 11F
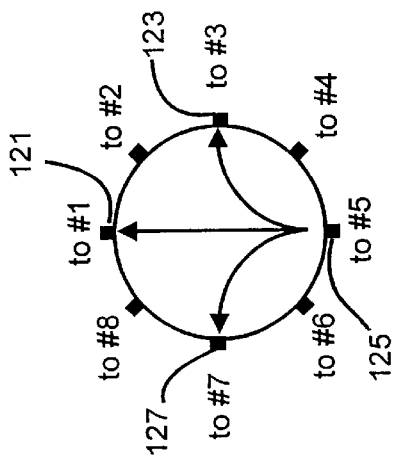

METHOD AND APPARATUS FOR TREATING MATERIALS WITH ELECTRICAL FIELDS HAVING VARYING ORIENTATIONS

CROSS-REFERENCE TO RELATED APPLICATION

This application is a continuation of application Ser. No. 09/637,381, filed Aug. 15, 2000 now abandoned, which is a division of Ser. No. 09/242,174, filed Feb. 10, 1999, now U.S. Pat. No. 6,117,660; which is a 371 of PCT/US97/09300, filed Jun. 10, 1997.

TECHNICAL FIELD

The present invention relates to the field of applying a defined pattern of pulsed electrical fields to materials, especially living cells. More specifically, the present invention is especially concerned with the fields of electroporation, electrofusion, and electromanipulation.

BACKGROUND ART

Electroporation and electrofusion are related phenomena with a variety of uses in manipulation of prokaryotic and eukaryotic cells. Electroporation is the destabalization of cell membranes by application of a brief electric potential (pulse) across the cell membrane. Properly administered, the destabalization results in a temporary pore in the membrane through which macromolecules can pass while the pore exists. Therefore, in electroporation, membranes of membrane-containing material open to admit treating substances. Electrofusion is the fusion of two or more cells by application of a brief electric potential across a cell membrane. In electrofusion, membranes of membrane-containing material open to merge with membranes of other membrane-containing material. In this respect, one membrane-containing material may be regarded as a treating substance for another membrane-containing material. The physical and biological parameters of electrofusion are similar to those of electroporation.

The potential applied to cell membranes is applied using instruments delivering various pulse shapes. The two most common pulse shapes are exponential decay and rectangular wave. The exponential decay pulse is generated with capacitance discharge pulse generators. It is the least expensive pulse generator and gives the operator the least control over pulse parameters. The rectangular wave pulse generator is more expensive, gives more control over pulse parameters and generates a pulse that is less lethal to cells. With both pulse shapes, the energy needed to generate resealable pores in cells is related to cell size, shape, and composition.

With electrofusion, cells must be in contact at the time of membrane destabalization. This is accomplished by physical means such as centrifugation, biochemical means such as antibody bridging, or electrical means through dielectrophoresis. Dielectrophoresis is the creation of a dipole within a cell by application of a low voltage potential across a cell membrane in an uneven electrical field. The dipole can be created in DC or AC fields. Since DC fields tend to generate unacceptable heat, radio frequency AC is often used for dielectrophoresis.

The uses of electroporation and electrofusion are many. A partial list follows: (1) transient introduction of DNA or RNA into both eukaryotic and prokaryotic cells; (2) permanent transfection of DNA into both eukaryotic and prokaryotic cells; (3) permanent and temporary transfection of DNA into human and animal cells for gene therapy; (4) introduction of antibodies, other proteins, or drugs into cells; (5) production of antibody producing hybridomas; (6) pollen electrotransformation in plants; (7) electroinsertion; (8) manipulation of animal embryos; (9) electrofusion of adherent cells; (10) production of plant somatic hybrids; (11) DNA vaccination; and (12) cancer therapy.

One of the ways that electroporation or electrofusion works is to induce the formation of holes or pores in the cell membrane. There is some controversy about the exact nature of the cell pore induced by the application of an electrical pulse to a cell, but the practical effect is an induced cell permeability and a tendency to fuse with other similarly affected cells that are in close contact. There is a DC voltage threshold for the induction of pores in or for the fusion of cell membranes. Voltages below the threshold will not bring about substantial cell membrane disturbance. The threshold potential for many cells is approximately one volt across the cell membrane. The total DC voltage applied per centimeter between electrodes to achieve one volt potential across the cell membrane is therefore proportional to the diameter of a cell. Small cells such as bacteria, require high DC voltages while larger cells, such as many mammalian cells, require somewhat lower voltages. There are other cell specific variables such as the structure of the cellular cytoskeleton that affect the voltage required for that cell.

When using DC electrical pulses which are powerful enough to bring about electroporation or electrofusion of cells, the main problem is that the process is often lethal to an unacceptable percentage of the cells. The lethality rate may be as high as 50% or higher. There are a number of reasons why such high lethality rates to cells are not desirable. When cells are treated for further use in ex vivo gene therapy, lethality to the cells will prevent an adequate number of cells from uptaking therapeutic genetic material. When in vivo gene therapy is employed in a patient, lethality to cells may not only result in less effective treatment, but may also result in causing injury to the patient.

A number of methods have been used to reduce cell killing in electroporation and electrofusion. The most commonly used method is to apply a rectangular shaped DC pulse to cells instead of an exponential decay pulse. This method reduces the total energy applied to the cell while applying enough DC voltage to overcome the threshold. While the rectangular shaped pulse is an improvement, there is still substantial cell killing during an effective application of electrical energy to the cells.

Rectangular wave pulsers currently marketed for electroporation and electrofusion have a number of adjustable parameters (voltage, pulse width, total number of pulses, and pulse frequency). These parameters, once set, are fixed for each pulse in each pulse session. For example if a voltage of 1,000 volts per centimeter, pulse width of 20 microseconds, pulse number equal to 10, and a pulse frequency of 1 Hz is chosen, then each of the 10 pulses will be fixed at 1000 volts per centimeter and 20 microseconds for the pulse session.

However, even when using rectangular wave pulsers that employ fixed pulse parameters, an undesirably high lethality rate of the cells may still occur. In this respect, it would be desirable if wave pulses could be controlled in such a way that the lethality rate of cells would be significantly reduced.

In an article by Sukharev et al entitled "Electroporation and electrophoretic DNA transfer into cells" in Biophys. J., Volume 63, November 1992, pages 1320–1327, there is a disclosure that three generators are employed to generate DC pulses. A time delay generator controls a first pulse generator to generate a first DC pulse to be imposed on biological Cos-1 cells. The first pulse has an amplitude sufficient to induce pore formation in the cells. The time delay generator causes a time delay and then controls a second pulse generator to generate a second DC pulse which is imposed on the cells. The second DC pulse is insufficient to sustain the induced pores formed from the first pulse. However, the second pulse is sufficient to bring about electrophoresis of DNA material into the previously pulsed cells. Several key points are noted with respect to the disclosures in the Sukharev et al article. First, the induced pores that are formed in the cells as a result of the first pulse begin to contract after the first pulse is over without any additional pulse being imposed on the cells sufficient to sustain the induced pores. Second, the Sukharev et al article does not address the issue of cell viability after the induced-pore-forming pulse. Third, there are only two pulses provided with Sukharev et al. Therefore, the time period that the DNA material can enter the cells is constrained by the effects of only two brief pulses. In this respect, it would be desirable if a pulse protocol were provided that sustains induced pores formed in electroporation. Moreover, it would be desirable if a pulse protocol were provided which is directed towards improving cell viability in cells undergoing electroporation. Furthermore, it would be desirable if a pulse protocol were provided which provides three or more pulses to allow more time for materials to enter cells undergoing electroporation.

In an article by Ohno-Shosaku et al entitled "Somatic Hybridization between Human and Mouse Lymphoblast Cells Produced by an Electric Pulse-Induced Fusion Technique" in Cell Structure and Function, Vol. 9, (1984), pages 193–196, there is a disclosure if the use of an alternating electric field of 0.8 kV/cm at 100 kHz to fuse biological cells together. It is noted that the alternating current provides a series of electrical pulses all of which have the same duration, the same magnitude, and the same interval between pulses.

In an article by Okamoto et al entitled "Optimization of Electroporation for Transfection of Human Fibroblast Cell Lines with Origin-Defective SV40 DNA: Development of Human Transformed Fibroblast Cell Lines with Mucopolysaccharidoses (I–VII)" in Cell Structure and Function, Vol. 17, (1992), pages 123–128, there is a disclosure that a variety of electric parameters were tested to obtain optimum electroporation. The electric parameters included voltage, pulse-duration, the number of pulses, and pulse shape. It is noted that for any particular set of electric parameters that were selected, all of pulses with the selected parameters had the same duration, the same magnitude, and the same interval between pulses.

In an article by Orias et al entitled "Replacement of the macronuclear ribosomal RNA genes of a mutant Tetrahymena using electroporation" in Gene, Vol. 70, (1988), pages 295–301, there is a disclosure that two different electroporation devices were employed. It is noted that each electroporation device provided a series of electrical pulses (pulse train) for each electroporation run. For any particular electroporation run, all of the pulses in the pulse train had the same duration, the same magnitude, and the same interval between pulses.

In an article by Miller et al entitled "High-voltage electroporation of bacteria: Genetic transformation of *Campylobacter jejuni* with plasmid DNA" in Proc. Natl. Acad. Sci USA, Vol. 85, February 1988, pages 856–860, there is a disclosure that a variety of electric pulse parameters were tested to obtain optimum electroporation. The electric pulse parameters included field strength and time constant. It is noted that for any particular set of pulse parameters that were selected, all of pulses with the selected parameters had the same field strength and the same time constant.

In an article by Ogura et al entitled "Birth of normal young after electrofusion of mouse oocytes with round spermatids" in Proc. Natl. Acad. Sci USA, Vol. 91, August 1994, pages 7460–7462, there is a disclosure that oocytes were electroactivated by exposures to AC (2 MHz, 20–50 V/cm for 10 seconds) and DC (1500 V/cm for 80 microsec.) pulses in Dulbecco's PBS medium. Following electroactivation, the cells were removed from the Dulbecco's PBS medium and placed in a Hepes/Whitten medium and injected with single spermatids. The oocyte-spermatid pairs were placed in fusion medium and exposed to, in sequence, an AC pulse (2 MHz, 100 V/cm, for 15–30 seconds), a fusion DC pulse (3750–4000 V/cm for 10 microsec.), and a subsequent AC pulse (2 MHz, 100 V/cm for 15–3.0 seconds). The time interval between application of the oocyte activation pulse and the oocyte-spermatid fusion pulse was 15–40 minutes. Several points are noted with respect to the disclosures in the Ogura et al article. First, electroporation is not conducted; instead, electrofusion is conducted. Moreover, entry of the spermatid into the oocyte is by injection, not electroporation. Second, only two DC pulses are employed. Neither of the AC pulses has a sufficient voltage level to provide an electroporation threshold, e.g. 200 V/cm. The sequence of two DC pulses are not disclosed as having induced pore formation. Pore formation is not utilized in this method of cell fusion. No provision is made to sustain pores formed or to maintain viability of cells treated.

In an article by Andreason et al entitled "Optimization of electroporation for transfection of mammalian cell lines" in Anal. Biochem., Vol. 180, No. 2, pages 269–275, Aug. 1, 1989, there is a disclosure that transfection by electroporation using square wave pulses, as opposed to exponentially decaying pulses, was found to be significantly increased by repetitive pulses. Different pulse amplitudes were tried in different experimental runs to determine the effects of different electric field strengths. For a given experimental run, each DC pulse has the same voltage and same duration as each other DC pulse.

In an article by Vanbever et al entitled "Transdermal Delivery of Metoprolol by Electroporation" in Pharmaceutical Research, Vol. 11, No. 11, pages 1657–1662, (1994), there is a disclosure that electroporation can be used to deliver drugs across skin tissues. The article discloses a series of electroporation experiments for the purpose of determining optimum electroporation conditions. An electroporation apparatus was employed that could be programmed to produce three types of pulses based on exponentially decaying capacitive discharge: a single HV pulse (ranging from 3500 V to 100 V; a single LV pulse (ranging from 450 V to 20 V); and a twin pulse consisting of a first HV pulse, and interpulse delay (1 second), and a second LV pulse. If more than one pulse were applied, they were separated by 1 minute. It is noted that none of the pulses applied are rectangular in shape. In actual experiments run, using a twin pulse, the second LV pulse had a pulse amplitude of 100 volts (see FIGS. 1 and 2 on page 1659). As a result of comparisons made between the results of actual experiments conducted, it was concluded in the second column on page 1659 that "single pulse was as efficient as the twin pulse to promote metoprolol permeation, indicating that twin pulse application was not necessary". Moreover, a further conclusion beginning in the same column of the same page and extending to the first column of page 1660 states "long pulse (621±39 ms) at a low voltage was much more efficient than a high voltage pulse with a short pulse time (3.1±0.1 ms) to promote metoprolol permeation". Beginning in the first paragraph of the first column on page 1660, the authors state "The short high voltage pulses used in this study hardly had any effect, while pulses of hundreds of volts and a few ms time constants were reported to have dramatic effect on transdermal permeation". Clearly, Vanbever et al teach away from using a pulse train having pulses of different amplitudes. Moreover, nothing in the Vanbever et al article relates to the issue of cell viability for cells undergoing electroporation.

In an abstract of an article by Bahnson et al entitled "Addition of serum to electroporated cells enhances survival and transfection efficiency" in Biochem. Biophys. Res. Commun., Vol. 171, No. 2, pages 752–757, Sep. 14, 1990, there is a disclosure that serum rapidly reseals the membranes of electroporated cells and that timely addition of serum following electroporation can improve cell survival and transfection efficiency. Rather than require the use of serum, it would be desirable is an electrical way were provided to improve cell survival and transfection efficiency.

In an abstract of an article by Knutson et al entitled "Electroporation: parameters affecting transfer of DNA into mammalian cells" in Anal. Biochem., Vol. 164, No. 1, pages 44–52, July 1987, there is a disclosure of an instrument which permits the high-voltage discharge waveform to be varied with respect to rise time, peak voltage, and fall time. Tests were done in which the mammalian cells were exposed to multiple voltage discharges, but the multiple exposures did not improve DNA transfer. It is noted that with the use of multiple pulses, each pulse has the same voltage and same duration as each other pulse.

In an abstract of an article by Kubiniec et al entitled "Effects of pulse length and pulse strength on transfection by electroporation" in Biotechniques, Vol. 8, No. 1, pages 16–20, January 1990, there is a disclosure that the relative importance of pulse field strength E and pulse length tau ½ (half decay time of an exponential decay pulse) were investigated for HeLa or HUT-78 cells. In the abstract, there is no disclosure of using a plurality of DC pulses for carrying out the electroporation.

Throughout the years a number of innovations have been developed in the fields and electroporation, electrofusion, dielectrophoresis, and the U.S. patents discussed below are representative of some of those innovations.

U.S. Pat. No. 4,441,972 discloses a device for electrofusion, cell sorting, and dielectrophoresis which includes specially designed electrodes which provide a non-uniform electrical field. The non-uniform electric fields are used for sorting cells. More specifically, at least one of the electrodes has a surface which includes a plurality of substantially concentric grooves. Because preparation of such concentric-groove-containing electrodes may be expensive and time consuming, it would be desirable if an electrofusion device could be provided that provides variations in electric fields applied to living cells without the use of electrodes having a plurality of concentric grooves.

The device in U.S. Pat. No. 4,441,972 can be used for cell sorting by dielectrophoresis. For cell sorting, the frequency and intensity of an AC voltage that is applied to the electrodes may be varied so that the cells which are desired for collection will arrive at a predetermined radial distance from an opening port and then later be collected and withdrawn through an exit port when the field is relaxed. DC electrical pulses are not used for cell sorting.

The device in U.S. Pat. No. 4,441,972 can also be used for electrofusion. With this manner of use, a low AC voltage is applied to the electrodes in order to allow the cells to contiguously align between the electrodes. Typically a mild AC field of about 10 volts rms at about 250 Khz may be utilized. Then, a single brief pulse of about 10 to about 250 volts DC for about 50 microseconds may be applied to cause fusion of the aligned cells. The patent discloses that the frequency, voltage and duration of impulse may be adjusted depending on the type and size of cells to be sorted or fused or upon the type of carrier stream used. In the patent, there is disclosure that various devices, including computers, can be used to control input frequency and voltage to the electrode. However, with particular attention being paid to electrofusion, in U.S. Pat. No. 4,441,972, there is no disclosure of using more than a single DC pulse for carrying out the electrofusion. It is noted that U.S. Pat. No. 4,476,004 is closely related to U.S. Pat. No. 4,441,972 and has a similar disclosure.

U.S. Pat. No. 4,695,547 discloses a probe for electrofusion, electroporation, and the like. A suitable source of high voltage pulses is disclosed as being capable of providing output voltage pulses in the range of 25–475 DC at currents up to 1 amp and durations of 1–990 ms. There is no disclosure of using a plurality of DC pulses for carrying-out electrofusion or electroporation.

U.S. Pat. No. 4,750,100 discloses a high-voltage and high-amperage switching device capable of delivering an exponential decay pulse or a rectangular wave pulse for electroporation. There is no disclosure of using a plurality of DC pulses for carrying out electroporation or transfection.

U.S. Pat. No. 4,832,814 discloses an electrofusion cell that is used for conducting electrofusion of living cells. An electrical power source provides a series of three DC pulses, each of 12 microsecond and of 68 volts with a 1 second separation between pulses. It is noted that each DC pulse has the same voltage and same duration as each other DC pulse.

U.S. Pat. No. 4,882,281 discloses a probe for electrofusion, electroporation, and the like. Just as disclosed in U.S. Pat. No. 4,695,547 described above, a suitable source of high voltage pulses is disclosed as being capable of providing output voltage pulses in the range of 25–475 DC at currents up to 1 amp and durations of 1–990 ms. There is no disclosure of using a plurality of DC pulses for carrying out electrofusion or electroporation.

U.S. Pat. No. 4,910,140 discloses a method for the electroporation of prokaryotic cells by applying high intensity electric fields of short duration. This patent discloses that the pulse will normally consist of a single pulse comprising the entire desired period. Alternatively, the pulse may consist of a plurality of shorter pulses having a cumulative time period coming with desired 2 to 20 msec range. Such a series of pulses must be spaced sufficiently close to one another so that the combined effect results in permeabilization of the cell wall. Typically, such pulses are spaced apart by 5 msec or less, more preferably being spaced apart by 2 msec or less.

U.S. Pat. No. 4,955,378 discloses electrodes for delivering pulses to animal or human anatomical sites for carrying out in vivo electrofusion. It is disclosed that, generally, electrofusion is preferably accomplished under constant voltage conditions by applying to the electrode 3 square waves of 20 volts amplitude and of 20 microsecond duration at a pulse rate of 1 pulse per second. It is noted that each DC pulse has the same voltage and same duration as each other DC pulse.

U.S. Pat. No. 5,007,995 discloses a device for electrofusion of living cells. Instead of using DC pulses, AC pulses were employed. A series of studies were conducted among the variables of AC frequency, AC voltage applied, and the time duration of the AC pulse. In each study, two of the three variables were held constant, and one variable was varied by setting the variable at different incremental settings. There is no disclosure of using a plurality of DC pulses for carrying out electrofusion.

U.S. Pat. No. 5,019,034 discloses a method for electroporating tissue for the purpose of transporting large molecules into the tissue. Frog skin is used as an example. In carrying out the electroporation, the shape, duration, and frequency of the pulse are selected. The peak voltage is also placed at an initial setting. The pulse is gradually cycled to higher voltages until electroporation occurs. At that point, the pulse shape, duration, frequency, and voltage are maintained until a desired amount of molecular transfer has occurred.

U.S. Pat. No. 5,124,259 discloses a method of electroporation using a specifically defined buffer in which the chloride ion is eliminated. There is a disclosure that, in carrying out the electroporation, the voltage may be 100–1000 V/cm and the time for applying the voltage may be 0.1–50 msec. There is no disclosure of using a plurality of DC pulses for carrying out the electroporation.

U.S. Pat. No. 5,128,257 discloses several chambers and electrodes used for electroporation. Power supplies provide a voltage range of 200 to 2000 volts. The pulse width is in a range from 0.1 to 100 milliseconds, preferably 1 to 10 milliseconds. There is no disclosure of using a plurality of DC pulses for carrying out the electroporation.

U.S. Pat. No. 5,134,070 discloses a specially coated electrode on which cells are cultivated. The cells on the electrode are subjected to electroporation. In carrying out the electroporation, a device for measuring electrical field intensity is appropriately interfaced to a micro-processor so that an "intelligent" electroporation device is provided which is capable of applying an ever increasing electrical potential until the cells have porated and which is capable of sensing at what field intensity the cells have porated. Since the device measures the conditions required to induce poration, and detects when poration occurs, substantial reductions in current mediated cell death will be realized since only enough energy to induce poration is introduced into the system. However, it is noted that there is no disclosure of using a plurality of DC pulses for carrying out electroporation. In addition, the electroporation device is capable of recording information concerning the poration potential required for various cell lines and the effects of various media compositions on the types and sizes of porations that may occur. It is noted, however, that provisions are not made to sustain pore formation that has been induced.

U.S. Pat. No. 5,137,817 discloses an apparatus and method for electroporation using specially designed electrodes for conducting electroporation in vivo. In carrying out the electroporation, a single DC voltage pulse is applied to the host cells. There is no disclosure of using a plurality of DC pulses for carrying out electroporation.

Each of U.S. Pat. Nos. 5,173,158 and 5,283,194 discloses an apparatus and methods for electroporation and electrofusion in which an electrode is employed that selectively admits cells of a certain size and excludes others. A single pulse generates an electric field which causes electroporation. There is no disclosure of using a plurality of DC pulses for carrying out either electroporation or electrofusion.

U.S. Pat. No. 5,186,800 discloses, as does U.S. Pat. No. 4,910,140 discussed above, a method for the electroporation of prokaryotic cells by applying high intensity electric fields of short duration. U.S. Pat. No. 5,186,800 also discloses that an applied pulse will normally consist of a single pulse comprising the entire desired period. Alternatively, the pulse may consist of a plurality of shorter pulses having a cumulative time period coming with desired 2 to 20 msec range. Such a series of pulses must be spaced sufficiently close to one another so that the combined effect results in permeabilization of the cell wall. Typically, such pulses are spaced apart by 5 microsec. or less, more preferably being spaced apart by 2 microsec. or less. A series of experiments were conducted to ascertain method parameters which provided maximum cell transformation. In each of the experiments, a single electrical pulse was used to bring about electroporation. Experimental parameters included a number of parameters of the electrical pulse, concentration of the host cells, concentration of the transforming material, and post-shock incubation period. It was observed that the viability and transformability of the cells undergoing electroporation were very sensitive to the initial electric field strength of the pulses. A conclusion reached was that cell survival declines steadily with increasing field strength; and in each of the experiments conducted, the maximum transformation efficiency is reached when 30 to 40% of the cells survive the pulse. There is no disclosure of using a plurality of DC pulses for carrying out electroporation. In view of the above, it would be desirable if a method of electroporation were provided in which the maximum transformation efficiency were achieved when greater than 40% of cells survive the pulse effecting electroporation.

U.S. Pat. No. 5,211,660 discloses a method for performing an in vivo electrofusion. Details relating to electrical parameters of a direct current electrical charge that is utilized are not disclosed.

U.S. Pat. No. 5,232,856 discloses an electroporation device which employs specially designed electrodes. A number of electroporation experiments were conducted using a number of different host cells and different transforming material. In each experiment, only a single DC pulse was applied to the host cells. There is no disclosure of using a plurality of DC pulses for carrying out electroporation.

U.S. Pat. No. 5,273,525 discloses a syringe based electroporation electrode for drug and gene delivery. In using the electroporation electrode, a conventional power supply is employed which provides from one to one hundred consecutive pulses having a constant pulse amplitude, a constant pulse width, and a constant pulse interval.

Each of U.S. Pat. Nos. 5,304,120 and 5,318,514 discloses an electrode for in vivo electroporation of living cells in a person. In applying electrical energy for bringing about electroporation, a power supply preferably applies electric fields repeatedly, and the amplitude and duration of the electric fields make the walls of the living cells sufficiently permeable to permit drugs or genes to enter the living cells without killing them. The power supply includes a unipolar oscillating pulse train and a bipolar oscillating pulse train. It is noted that, for a chosen pulse train, each pulse rises to the same voltage and has the same duration as each other pulse in a pulse train.

Having discussed a number of theoretical considerations and a number of prior art disclosures, attention is now returned to a further discussion of certain theoretical concepts relating to induction of pore formation in biological cells. It is understood, however, that none of the theoretical concepts discussed herein are intended to limit the scope of the invention. Instead, the scope of the invention is limited only by the claims appended hereto and equivalents thereof.

It has been discovered by the inventors of the present invention that changing pulse parameters during a pulse session reduces damage to cells while maintaining or improving electroporation and electrofusion efficiency. The reduced cell damage can be related to reduced energy applied to the cell. More specifically, two parameters determining total energy applied per pulse are pulse amplitude and pulse width. Variation of pulse width would have different effects than variation of pulse amplitude. Reduction of pulse width following application of a wider pulse would permit application of an above threshold voltage while reducing the total energy in a series of pulses.

Furthermore, for theoretical reasons described below, maintenance of pores already formed in a cell should require less energy than the energy required to initiate a new pore. Variation of pulse width while maintaining an above threshold voltage would be particularly useful in those instances where very small pores are initiated by a wider pulse. Narrower pulses could assist pore expansion in a controlled manner. The ideal condition for any particular type of cell would be to find a set of electrical pulse parameters that would cause pore expansion to a size large enough for permit a foreign molecule (such as a small organic molecule or DNA) to enter the cell without expanding the pore size to one beyond recovery. The pulse parameters to accomplish this goal would have to be experimentally determined for each cell type.

Variation of pulse amplitude would permit application of a below threshold maintenance pulse. Once a pulse of sufficient energy with an above threshold voltage is applied to a cell, a transient decrease in electrical resistance across the cell membrane occurs. Because of the decreased electrical resistance of the cell membrane, pulse voltages below threshold should be sufficient to maintain a cell pore induced by an above threshold pulse.

Thus, while the foregoing body of prior art indicates it to be well known to use electrical pulses to induce electroporation, the prior art described above does not teach or suggest a method of treating materials with pulsed electrical fields which has the following combination of desirable features: (1) provides a process for application of a series of electrical pulses to living cells wherein the electrical pulses produce reduced cell lethality; (2) provides an operator of electrical pulse equipment a process for maximum operator control of an applied pulse series; (3) provides a process for changing pulse width during a series of electrical pulses; (4) provides a process for changing pulse voltage during a series of electrical pulses; (5) provides a machine for control of the process; (6) provides a pulse protocol that sustains induced pores formed in electroporation; (7) provides a pulse protocol which provides three or more pulses to allow more time for materials to enter cells undergoing electroporation; (8) provides an electrical way to improve cell survival and transfection efficiency; and (9) provides a method of electroporation in which maximum transformation efficiency is achieved when greater than 40% of cells survive the pulse effecting electroporation. The foregoing desired characteristics are provided by the unique method of treating materials with pulsed electrical fields of the present invention as will be made apparent from the following description thereof. Other advantages of the present invention over the prior art also will be rendered evident.

Turning to another aspect of the science of electroporation, wherein treating substances are added to materials being electroporated, in the article "Electrochemotherapy: Transition from Laboratory to the Clinic", by Gunter A. Hofmann, Sukhendu S. Dev, and Gurvinder S. Nanda, in IEEE Engineering in Medicine and Biology, November/December 1996, pages 124–132, there is a disclosure of a mechanical switching arrangement for changing the directions of electrical fields applied to a set of electrodes arrayed around an in vivo organ. The mechanical switching arrangement is in the form of a mechanical rotating switch which mechanically selects electrodes in a six-needle array of electrodes. Such a mechanical switching arrangement bears a close relationship to an automobile distributor for distributing energy to spark plugs. Such a mechanical switching arrangement does not permit a wide variation in selectable sequences of pulse patterns for electrodes.

Aside from the field of electroporation, the concept of reversing the direction of electrical fields has been employed in a number of areas, such as cardiac cardioversion and defibrillation, gel electrophoresis and field inversion capillary electrophoresis.

With respect to cardiac applications, U.S. Pat. No. 5,324,309 of Kallok discloses a method and apparatus for cardioversion and defibrillation. In using this method, a plurality of pulses are directed to a plurality of electrodes placed in an array of locations around an animal heart. A microprocessor controlled switching device directs pulses to predetermined electrodes. The purpose of the Kallok method and apparatus is to modify the electrical system in the heart so that fibrillation or other electrical conduction problems are corrected. Kallok does not disclose adding any treating substances to the heart. In this respect, Kallok does not disclose that changing electrical fields aid in the uptake of the treating substances by the heart.

As a matter of interest, with gel electrophoresis, electrical fields from different directions are applied over relatively long periods of time (e.g. 0.6–125 seconds) and with relatively low voltages (e.g. 3.5–20 volts/cm.). Also, as a matter of interest, with field inversion capillary electrophoresis, the reverse-direction electrical fields are applied over relatively long periods of time (e.g. 2 seconds) and with relatively low voltages (e.g. 50 volts/cm). Moreover, with gel electrophoresis and field inversion capillary electrophoresis, membrane-containing materials (such as cells, tissues, organs and liposomes) do not undergo treatment.

DISCLOSURE OF INVENTION

Electrical pulse sequences are almost infinite in their potential variability. A great variety of pulse sequences are used in the areas of electrical communications and radar. For example, a pulse sequence can be continuous. A continuous pulse sequence can be unipolar or bipolar. A pulse sequence can include rectangular waves or square waves (a special case of rectangular waves). A predetermined number of rectangular pulses, either unipolar or bipolar, can be provided in a gated or burst pulse sequence. In a pulse sequence, pulses can be provided at different levels of amplitude (pulse amplitude modulation); this form of pulse train is used commonly in modems and computer to computer communications. Pulses can be provided with different pulse widths or durations (pulse width modulation); in such a case, a constant pulse interval can be maintained. Pulses can be provided with different pulse intervals (pulse interval modulation); in such a case, a constant pulse width can be maintained.

A specific category of electrical pulse sequences is known as an "agile pulse sequence". For purposes of the present patent, by definition, an agile pulse sequence has the following characteristics: (1) the number of pulses in the sequence can range from 2 to 1,000; (2) the pulses in the sequence are rectangular in shape; (3) each pulse in the sequence has a pulse width; (4) there is a pulse interval between the beginning of a pulse and the beginning of a succeeding pulse in the sequence; (5) pulse amplitude for pulses in the sequence is greater than 100 volts and preferably greater than 200 volts; and (6) pulse polarity can be unipolar or bipolar for pulses in the sequence. Another characteristic in an agile pulse sequence that may be present is that the "on" time of a rectangular pulse in the sequence is less than 10% of the pulse interval.

Although agile pulse sequences have been employed in communications and radar applications, agile pulse sequences have not been employed to treat materials. More specifically, the prior art does not disclose, and the subject invention provides, the use of agile pulse sequences to treat materials to provide very well controlled intense electric fields to alter, manipulate, or serve as a catalyst to cause well defined and controlled, permanent or temporary changes in materials.

More specifically, in accordance with the invention, a method is provided for treating materials, especially organic materials, with pulsed electrical fields, wherein the method includes the step of applying an agile pulse sequence having at least three pulses to a material, wherein the agile pulse sequence has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses.

More specifically, in accordance with the invention, a method is provided for treating materials, especially organic materials, with pulsed electrical fields and includes the step of applying an agile pulse sequence having at least three pulses to a material, wherein at least two of the at least three pulses differ from each other in pulse amplitude.

In accordance with the invention, a method is provided for treating materials, especially organic materials, with pulsed electrical fields and includes the step of applying an agile pulse sequence having at least three pulses to a material, wherein at least two of the at least three pulses differ from each other in pulse width.

In accordance with the invention, a method is provided for treating materials, especially organic materials, with pulsed electrical fields and includes the step of applying an agile pulse sequence having at least three pulses to a material, wherein a first pulse interval for a first set of two of the at least three pulses is different from a second pulse interval for a second set of two of the at least three pulses.

In accordance with another broad aspect of the invention, a method is provided for treating biological cells with pulsed electrical fields to induce pore formation in the cells. The method includes the step of applying an agile pulse sequence having at least three pulses to the cells, wherein the agile pulse sequence has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses, such that induced pores are sustained for a relatively long period of time, and such that viability of the cells is maintained.

More specifically, in accordance with the invention, a method is provided for treating biological cells with pulsed electrical fields to induce pore formation in the cells. The method includes the step of applying an agile pulse sequence having at least three pulses to the cells, wherein at least two of the at least three pulses differ from each other in pulse amplitude, such that induced pores are sustained for a relatively long period of time, and such that viability of the cells is maintained.

Further, in accordance with the invention, a method is provided for treating biological cells with pulsed electrical fields to induce pore formation in the cells. The method includes the step of applying an agile pulse sequence having at least three pulses to the cells, wherein at least two of the at least three pulses differ from each other in pulse width, such that induced pores are sustained for a relatively long period of time, and such that viability of the cells is maintained.

Also, in accordance with the invention, a method is provided for treating biological cells with pulsed electrical fields to induce pore formation in the cells. The method includes the step of applying an agile pulse sequence having at least three pulses to the cells, wherein a first pulse interval for a first set of two of the at least three pulses is different from a second pulse interval for a second set of two of the at least three pulses, such that induced pores are sustained for a relatively long period of time, and such that viability of the cells is maintained.

It is clear from the above description that an agile pulse sequence is a class of sequences of non-sinusoidal electrical pulses. In this respect, in accordance with the principles of the invention, other categories of non-sinusoidal electrical pulse sequences can employed for treating materials aside from agile pulse sequences.

In this respect, in accordance with a broader aspect of the invention, a method is provided for treating material with pulsed electrical fields and includes the step of applying a sequence of at least three non-sinusoidal electrical pulses, having field strengths equal to or greater than 100 V/cm and preferably equal to or greater than 200 V/cm, to the material. The sequence of at least three non-sinusoidal electrical pulses has one, two, or three of the following characteristics: (1) at least two of the at least three pulses differ from each other in pulse amplitude, (2) at least two of the at least three pulses differ from each other in pulse width, and (3) a first pulse interval for a first set of two of the at least three pulses is different from a second pulse interval for a second set of two of the at least three pulses. Preferably, the material is an organic material.

In accordance with another broad aspect of the invention, a method is provided for treating biological cells with pulsed electrical fields to induce pore formation in the cells and includes the step of applying a sequence of at least three non-sinusoidal electrical pulses, having field strengths equal to or greater than 100 V/cm and preferably equal to or greater than 200 V/cm, to biological cells. The sequence of at least three non-sinusoidal electrical pulses has one, two, or three of the following characteristics (1) at least two of the at least three pulses differ from each other in pulse amplitude, (2) at least two of the at least three pulses differ from each other in pulse width, and (3) a first pulse interval for a first set of two of the at least three pulses is different from a second pulse interval for a second set of two of the at least three pulses, such that induced pores are sustained for a relatively long period of time, and such that viability of the cells is maintained.

In accordance with still another aspect of the invention, a method of treating membrane-containing material with an added treating substance and with electrical fields is provided in which the directions of electrical fields are changed. In the field of electroporation, an important aspect is that the greatest effect is at sites on the cell where the electrical field is perpendicular to the tangent of the cell surface. Where electroporation is greatest, entry of the added treating substance into the cell is facilitated. Since cells are roughly round, the pores are therefore normally formed at the poles of the cells nearest the electrodes. The effect of the pulse decreases as the angle of the cell surface tangent becomes more parallel to the electrical field. The effect of electroporation becomes zero (on a perfect sphere) 90 degrees away from the site of maximal effect. With these considerations in mind, it has been realized that a change of electrical field direction would expose different areas of cells to maximal electrical fields, whereby entry of the added treating substance into the cells would be facilitated. This change of direction of electrical fields would induce the formation of more pores in the cell and, therefore, increase electroporation efficiency.

The method of the invention, in which the directions of electrical fields are changed, is comprised of the following steps. A plurality of electrodes are arranged in an array of locations around the membrane-containing material to be treated. The electrodes are connected to outputs of an electrode selection apparatus. Inputs of the electrode selection apparatus are connected to outputs of an agile pulse sequence generator. A treating substance is added to the membrane-containing material. Electrical pulses are applied to the electrode selection apparatus. The applied pulses are routed through the electrode selection apparatus in a predetermined sequence to selected electrodes in the array of electrodes, whereby the material is treated with the added treating substance and with electrical fields of sequentially varying directions.

The routing of applied pulses through the electrode selection apparatus in a predetermined sequence to selected electrodes in the array of electrodes can be done in a number of ways with the invention.

In one type of pulse routing, a first pulse can be applied to a first selected group of electrodes. Then, a second pulse can be applied to a second selected group of electrodes. Then, a third pulse can be applied to a third selected group of electrodes. This type of pulse routing can be generalized by stating that a sequence of N pulses can be routed to N selected groups of electrodes in sequence.

As an example, there can be eight electrodes arrayed around an in vivo tissue. Pulses applied can be high voltage agile pulse sequences of at least three non-sinusoidal electrical pulses, having field strengths equal to or greater than 100 V/cm, wherein the sequence of at least three non-sinusoidal electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second-pulse interval for a second set of two of the at least three pulses. A first pulse of an agile pulse sequence can be routed to the first, third, fifth, and seventh electrodes. A second pulse of an agile pulse sequence can be routed to the second, fourth, sixth, and eighth electrodes. A third pulse of an agile pulse sequence can be routed to the first, second, fourth, and fifth electrodes. The possible number of variations of selected groups of only eight electrodes from pulse to pulse is a very large number with the apparatus and method of the invention. Using even more electrodes, would provide even a greater number of possible variations. This type of pulse routing can be generalized by stating that N pulses which comprise an agile pulse sequence can be routed to N selected groups of electrodes in sequence. An even broader statement can be made to the effect that, with the invention, N pulses which comprise an agile pulse sequence can be routed to N selected groups of electrodes in any combination and in any order.

In another type of pulse routing for in vivo tissues, a first high voltage agile pulse sequence pattern can be applied to a first selected group of electrodes. Then, a second pulse pattern can be applied to a second selected group of electrodes. Then, a third pulse pattern can be applied to a third selected group of electrodes. This type of pulse routing can be generalized by stating that N pulses patterns can be routed to N selected groups of electrodes in sequence.

As another example, there can still be eight electrodes arrayed around an in vivo tissue. A first pulse pattern can be routed to the first, third, fifth, and seventh electrodes and returned by way of the second, fourth, sixth, and eighth electrodes. A second pulse pattern can be routed to the first, second, fourth, and fifth electrodes and returned by way of any one or more of the remaining electrodes. The possible number of variations of selected groups of only eight electrodes from pulse pattern to pulse pattern is a very large number with the apparatus and method of the invention. Using even more electrodes, would provide even a greater number of possible variations.

When the object subjected to high voltage agile pulse electrical pulse treatment is an in vivo object, e.g. an animal (including human) or plant tissue or organ, in which cells are being electroporated, the direction of the electric fields in a high voltage agile pulse sequence of pulses applied to the electrodes can be rotated, whereby electroporation into the in vivo body part is improved.

In accordance with another aspect of the invention, a method is provided for treating membrane-containing material in vitro with electrical fields. The membrane-containing material can include cells, tissue, organs, and liposomes. This in vitro method of the invention includes the steps of:

arranging the in vitro material in an array of locations;

arranging a plurality of electrodes in an array of locations corresponding to the array of in vitro material locations; connecting the electrodes to outputs of an electrode selection apparatus;

connecting inputs of the electrode selection apparatus to outputs of an electrical pulser apparatus;

applying electrical pulses to the electrode selection apparatus; and routing applied pulses through the electrode selection apparatus in a predetermined sequence to selected electrodes in the array of electrodes, whereby the in vitro material in the array of locations is treated with electrical fields sequentially in the array of locations.

In one manner of carrying out the in vitro method of the invention, at least two successive pulses applied to a selected electrode are reversed in electric field direction. In another manner of carrying out the in vitro method of the invention, the electrodes are arrayed as M pairs of electrodes associated with M wells in a testing plate. In another manner of carrying out the in vitro method of the invention, the electrodes are arrayed as a pair of electrodes associated with a cuvette. In another manner of carrying out the in vitro method of the invention, the electrodes are arrayed as P electrodes associated with a cuvette, wherein P is greater than two.

When the electrodes are arrayed as M pairs of electrodes for M wells (cuvettes) in a testing plate, high voltage pulses/electric fields may be routed to any of these cuvettes in any order by computer control of the electrode selection apparatus. This can be used to run a large number of experiments, for example in a sensitivity analysis greatly reducing the time to run the experiments by using one cuvette at a time.

When the object subjected to electrical pulse treatment is an in vitro object, e.g. a cuvette, in which cells are being electroporated, the direction of the electric fields in a sequence of pulses applied to the electrodes can be rotated, whereby electroporation is improved.

When the electrodes are arrayed as two electrodes located on opposite sides of a cuvette in which biological cells are being subject to electroporation, the direction of the electric fields in a sequence of pulses applied to the electrodes can be sequentially reversed, whereby electroporation is improved.

In accordance with yet another aspect of the present invention, an apparatus is provided for treating materials with electrical pulses. The subject apparatus includes an agile pulse sequence generator and an electrode selection apparatus electrically connected to the agile pulse sequence generator The electrode selection apparatus includes a set of input connectors electrically connected to the agile pulse sequence generator, a set of at least two output connectors, and an array of selectable switches connected between the input connectors and the output connectors. A set of electrodes is electrically connected to at least two of the output connectors of the electrode selection apparatus. Preferably, the selectable switches are programmable computer controlled switches. Alternatively, the selectable switches can be manually operated switches.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In view of the above, it is an object of the present invention is to provide a method of treating materials with pulsed electrical fields which provides a process for application of a series of electrical pulses to living cells wherein the electrical pulses produce reduced cell lethality.

Still another object of the present invention is to provide a method of treating materials with pulsed electrical fields that provides an operator of electrical pulse equipment a process for maximum operator control of an applied pulse series.

Yet another object of the present invention is to provide a method of treating materials with pulsed electrical fields which provides a process for changing pulse width during a series of electrical pulses.

Even another object of the present invention is to provide a method of treating materials with pulsed electrical fields that provides a process for changing pulse voltage during a series of electrical pulses.

Still a further object of the present invention is to provide a method of treating materials with pulsed electrical fields which provides a machine for control of the process.

Yet another object of the present invention is to provide a method of treating materials with pulsed electrical fields that provides a pulse protocol that sustains induced pores formed in electroporation.

Still another object of the present invention is to provide a method of treating materials with pulsed electrical fields which provides a pulse protocol which provides three or more pulses to allow more time for materials to enter cells undergoing electroporation.

Yet another object of the present invention is to provide a method of treating materials with pulsed electrical fields that provides an electrical way to improve cell survival and transfection efficiency.

Still a further object of the present invention is to provide a method of treating materials with pulsed electrical fields that provides a method of electroporation in which maximum transformation efficiency is achieved when greater than 40% of cells survive the pulse effecting electroporation.

Yet another object of the invention is to provide a method and apparatus for selectively applying electrical pulses to an array of electrodes, either in vivo or in vitro.

Still another object of the invention is to provide a method and apparatus for rotating an electrical field applied to either a tissue or organ in vivo or a cuvette in vitro.

Yet another object of the invention is to provide a method and apparatus for sequentially applying and reversing electrical fields applied to a cuvette in vitro.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF DRAWINGS

The invention will be better understood and the above objects as well as objects other than those set forth above will become more apparent after a study of the following detailed description thereof. Such description makes reference to the annexed drawing wherein:

FIGS. 2A–2O are circuit diagrams relating to the interface-control assembly of FIG. 2. More specifically, FIG. 2A is a circuit diagram of Status to microprocessor (IN). FIG. 2I is a circuit diagram of HV Power Supply VMON. FIG. 2O is a circuit diagram of Non Volatile Static RAM.

FIGS. 3A–3I are circuit diagrams relating to the high voltage assembly shown in FIG. 3. More specifically, FIG.

3A is a circuit diagram of HV Control and PS VMON. FIG. 3B is a circuit diagram of the Reservoir Capacitor. FIG. 3C is a circuit diagram of the HV Switch. FIG. 3D is a circuit diagram of Power Supply and Pulse Disable with FAULT. FIG. 3E is a circuit diagram of HV Power Supply Program Voltage and Discharge Control. FIG. 3F is a circuit diagram of Pulse Voltage Monitor (P-VMON). FIG. 3G is a circuit diagram of Pulse Control Monitor (P-IMON). FIG. 3H is a circuit diagram of Signal Bus Interface. FIG. 3I is a circuit diagram of Fault Monitor Circuits.

FIGS. 10A–10F illustrate a first exemplary pattern of moving electric fields through the single cuvette wherein a two-pole electric field is rotated through the cuvette.

FIGS. 11A–11F illustrate a second exemplary pattern of moving electric fields through the single cuvette wherein a four-pole electric field is rotated through the cuvette.

MODES FOR CARRYING OUT THE INVENTION

Figure 1:
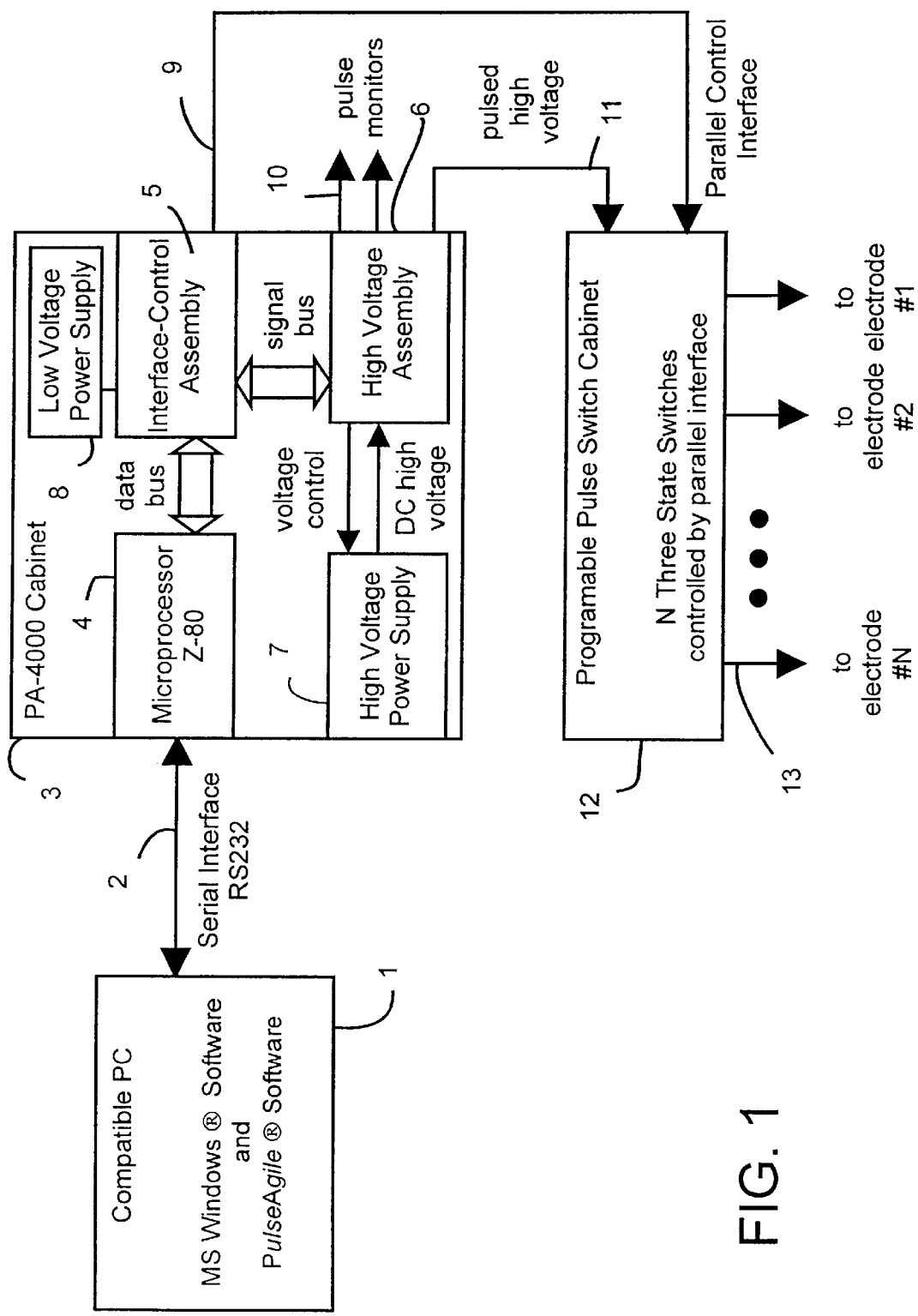
FIG. 1 is a block diagram of the overall apparatus used to carry out the method of the invention of treating materials with pulsed electrical fields and with a programmable electrode selection apparatus.

This invention involves a process for applying electrical pulses to living cells for the purpose of electroporation or electrofusion. The parameters of pulse width and pulse voltage can be changed from pulse to pulse by prior hardware or software programming. An important object of applying pulses of changing voltage and width is to maximize the desired result of electroporation or electrofusion and minimize lethal damage to cells. This object may be achieved by optimizing the energy applied to cells through reduction of applied energy after an initial higher energy pulse.

Conventional theory in the fields of electroporation and electrofusion teaches that a threshold voltage must be exceeded to achieve cell electroporation or electrofusion. In implementing the conventional theory, a single pulse is employed by applying a pulse with a voltage above threshold. Moreover, the single pulse concept is extended in conventional theory to include a series of pulses without accounting for the changes in cell membrane resistance induced by the first above-threshold pulse. The inventors of the subject invention described herein have realized that changes in cell membrane resistance induced by the first above-threshold pulse should be taken into consideration in applying subsequent pulses.

It also is accepted in conventional theory that the energy of a pulse is as important as the voltage of a pulse. Within limited parameters, decreasing pulse width has the same effect as decreasing pulse voltage. Again, conventional wisdom does not take into consideration the altered electrical resistance following the first pulse when sequential pulses of equal energy are applied.

The diameter of a pore induced in a cell is increased by increasing energy. Beyond a critical energy level that is dependent upon cell type and size, a pore is created that destroys the cell by unlimited expansion. Cell structures such as the cell cytoskeleton, limit the expansion of cell pores. Maximum poration is achieved by a maximum number of pores of a size as close to but not larger than the pore size that results in unlimited pore expansion.

It is understood that the metes and bounds of the subject invention are not bound by theoretical considerations. However, for purposes of better understanding of the use and operation of the subject invention, a brief theoretical explanation may be helpful. More specifically, in accordance with new theoretical considerations set forth by the inventors herein, if an applied pulse initiates pore formation in a cell and that pulse is followed by a pulse of lesser energy, the second pulse would have the effect of expanding the pore at a slower rate than a pulse of full initial energy. Pulses of continually decreasing energy would have the effect of even slower pore expansion thus allowing a greater control of pore expansion nearer the critical maximum pore size.

As stated above, conventional theory relating to electroporation does not discuss an occurrence of decreased cell membrane resistance with continually expanding pore size. However, it is appreciated by the inventors herein that this decreased resistance may actually result in less effect of the applied voltage because the local voltage decreases in proportion with the decreased local resistance. This would result in additional attenuation of the tendency to expand pore size. In this respect, conventionally applied pulse trains may expand pores too rapidly to take advantage of this natural attenuation of pore expansion. It is the inventors' appreciation that approaching maximum pore size through the application of stepwise decreasing or continually decreasing the pulse energy in a train of pulses would permit maximum usage of the natural attenuation of pore size expansion through decreased cell membrane resistance.

Electroporation of a cell is a heterogenous process for several reasons. First, cells are roughly round and the electrical force upon the cell membrane is proportional to the angle of the cell membrane relative to the direction of current. The greatest force is at the site of the cell where the cell membrane is perpendicular to the current. Second, cell membranes are irregular in shape. Some cells have projections that have cell membrane sections perpendicular to the current at sites distant to the site nearest to the electrode. Irregularities is cytoskeleton contribute to heterogenous electroporation.

Irregular electroporation makes maximization of electroporation difficult because if only one pore expands beyond rupture, the cell will die. This makes it imperative to develop a technique that gently expands pores after pore initiation. The subject invention satisfies this need.

With reference to the drawings, apparatus for carrying out the method of treating materials with pulsed electrical fields embodying the principles and concepts of the present invention are illustrated.

The apparatus employed for carrying out the method of treating material with pulsed electrical fields of the invention includes the Model PA-4000 Electroporation System of Cyto Pulse Sciences, Inc., Columbia, Md., USA, shown in FIG. 1. The Model PA-4000 Electroporation System is designed to accomplish a wide range of electroporation tasks, many of which are not possible with existing equipment. Some of the new tasks that can be carried out by the Model PA-4000 Electroporation System include: changing pulse width from one pulse to the next; changing pulse amplitude from one pulse to the next; changing pulse interval from one pulse to the next; producing a high fidelity pulsed electric field, effectively independent of load; providing a pulse amplitude monitor which gives a very accurate replica of high voltage pulses; providing a pulse current monitor which gives a very accurate replica of pulse current; providing a computer-generated agile pulse sequence; and providing automatic data logging and recall of each pulse sequence used. As a result, the Model PA-4000 Electroporation System provides a sequence of very finely controlled, high fidelity, pulsed electric fields to electroporate a wide variety of materials including plant and mammalian cells.

The Model PA-4000 Electroporation System includes three major components: a high voltage agile pulse sequence generator 7 (known as Pulse Agile (™) generator); a combined control computer and computer interface 4; and a cuvette apparatus. The cuvette apparatus operates with standard 0.4 cm, 0.2 cm and 0.1 cm cuvettes. Custom interfaces are available for other cuvette holders and delivery systems. The Model PA-4000 Electroporation System specifications are contained in the Specifications Table presented below.

Specifications Table
for Model PA-4000 Electroporation System

| PULSE PARAMETERS | Field Strength vs Cuvette Used | | |
|---|---|---|---|
| | 0.4 cm | 0.2 cm | 0.1 cm |
| Voltage-Low Range: (step size 1 volt) | | | |
| Minimum 10 volts | 25 v/cm | 50 v/cm | 100 v/cm |
| Maximum 255 volts | 637 v/cm | 1275 v/cm | 2550 v/cm |
| High Range: (step size 5 volts) | | | |
| Minimum 50 volts | 125 v/cm | 250 v/cm | 500 v/cm |
| Maximum 1100 volts | 2750 v/cm | 5500 v/cm | 11000 v/cm |

| | |
|---|---|
| Time Required to Decrease Amplitude (previous pulse to next pulse) | <50 milliseconds |
| Maximum Pulse Current | 120 amps |
| Pulse Droop | <5% at pulse width of 100 Microsecs into 20 ohms |
| Width | 1 Microsec to 1000 Microsecs |
| Width Step Size | 1 Microsec |
| Rise Time | <100 ns |
| Interval: | |
| Minimum | 0.1 seconds (a function of amplitude change) |
| Maximum | 4,000 seconds |
| Interval Step Size | 1 millisec |

-continued

Specifications Table
for Model PA-4000 Electroporation System

MODES

Rectangular wave up to 99 times 9 pulses
Agile Pulse Sequence
9 Groups; Pulse Parameters Constant Within Group
1 to 100 pulses per group
FRONT PANEL STATUS LED'S Cuvette Holder Open
Fault
Pulser Ready
Process On
High Voltage Enabled
High Voltage Off Zero
Pulsing
WINDOWS OPERATOR INTERFACE Set-up of Pulse Sequence
Automatic Save of Sequence File with Unique File Name
Automatic Data Logging
SAFETY Pulser will not operate when cuvette holder open
Front Panel Sequence Stop Button
Load resistance check before high voltage turned on
High Voltage Pulsing Shut Down on Detection of Load Fault
High Voltage Pulsing Shut Down on Detection of Internal Fault More specifically with respect to the agile pulse sequencer (known as Pulse Agile (™) generator) the overview is shown in FIG. 1. This Figure shows the PA-4000 system configured with the Programmable Pulse switch. The cuvette Holder may also be connected at the output of the Programmable Pulse Switch or if the Programmable Pulse Switch is not used the Cuvette Holder may be connected directly to the Pulsed high voltage out 11. Also available are pulse voltage and current monitor ports, 10. An oscilloscope may be connected to these port to view replicas of the pulse signals. A control cable 9 is used to control the Programmable Pulse Switch. The programmable Pulse Switch has N output which are set to one and only one of three states, pulse out, pulse return, no connection 13.

The system consists of three cabinets, the compatible PC 1, the PA-4000 cabinet 3 which contains the control microprocessor 4, the Interface-Control Assembly 5, the High Voltage Assembly 6, the High Voltage Power Supply 7, and the low voltage power supply 8 and the Programmable Pulse Switch Cabinet 12.

The interface to the user is the PulseAgile software installed on the compatible PC and operating under the MS Windows operating system 1. The operator set the pulse parameter and control the process start and stop. After the protocol is run a data log report is presented on the computer screen. The PulseAgile software in the compatible PC generates commands and sends the commands over a standard RS 232 serial interface 2 to the Z-80 microprocessor in the PA-4000 cabinet 4. The Z-80 interprets the commands and in turn controls all other assemblies. In addition the Z-80 monitors the status of the circuits, and provides status report back via the RS-232 link to the PulseAgile operator interface software. Communicating over the serial interface can be accomplished with any terminal program. However, the graphical interface software in the PC makes the interface much more user friendly.

Figure 2:
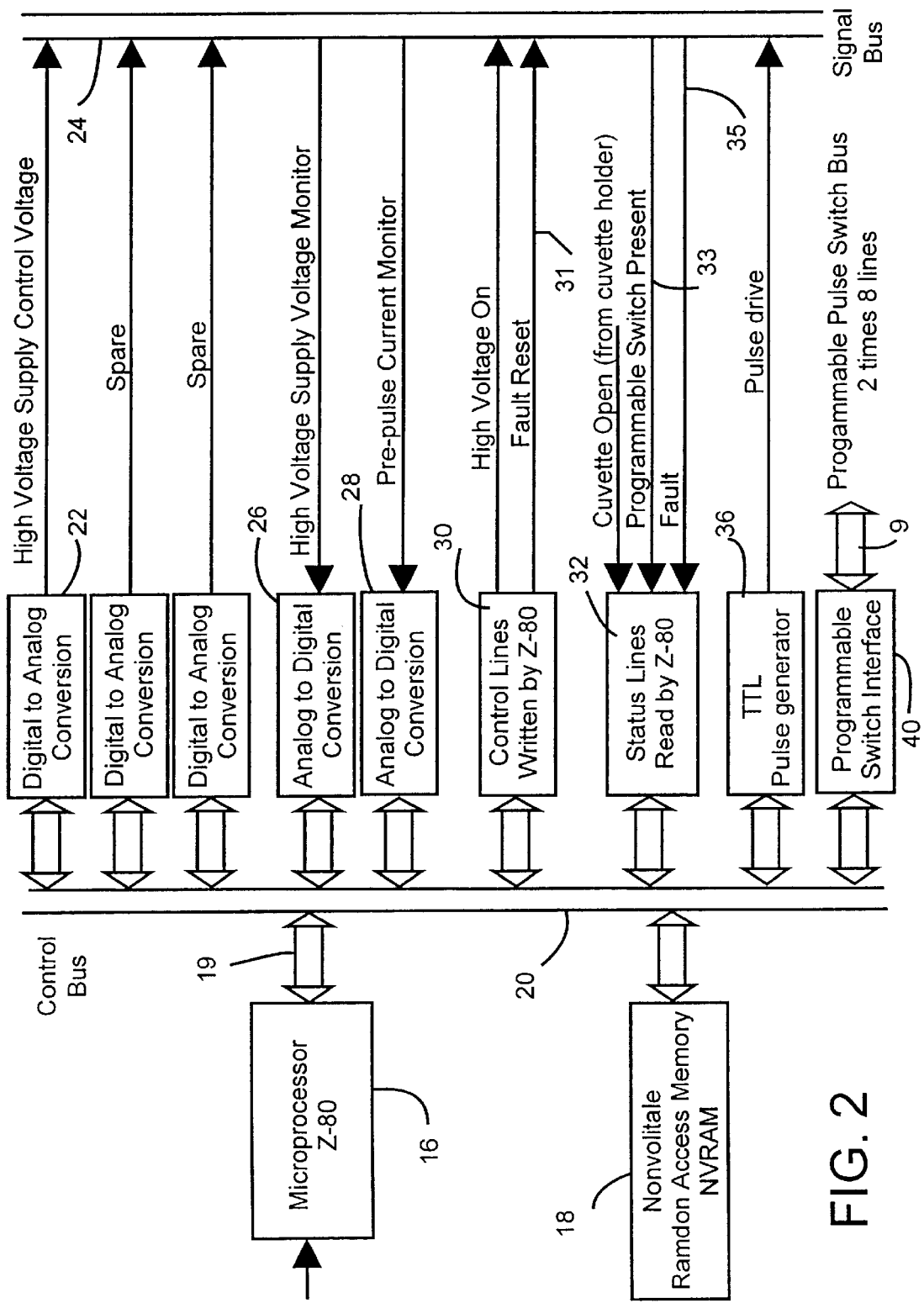
FIG. 2 is a block diagram, partially in schematic form, showing major functional units of the interface-control assembly shown in FIG. 1.
Figure 2A:
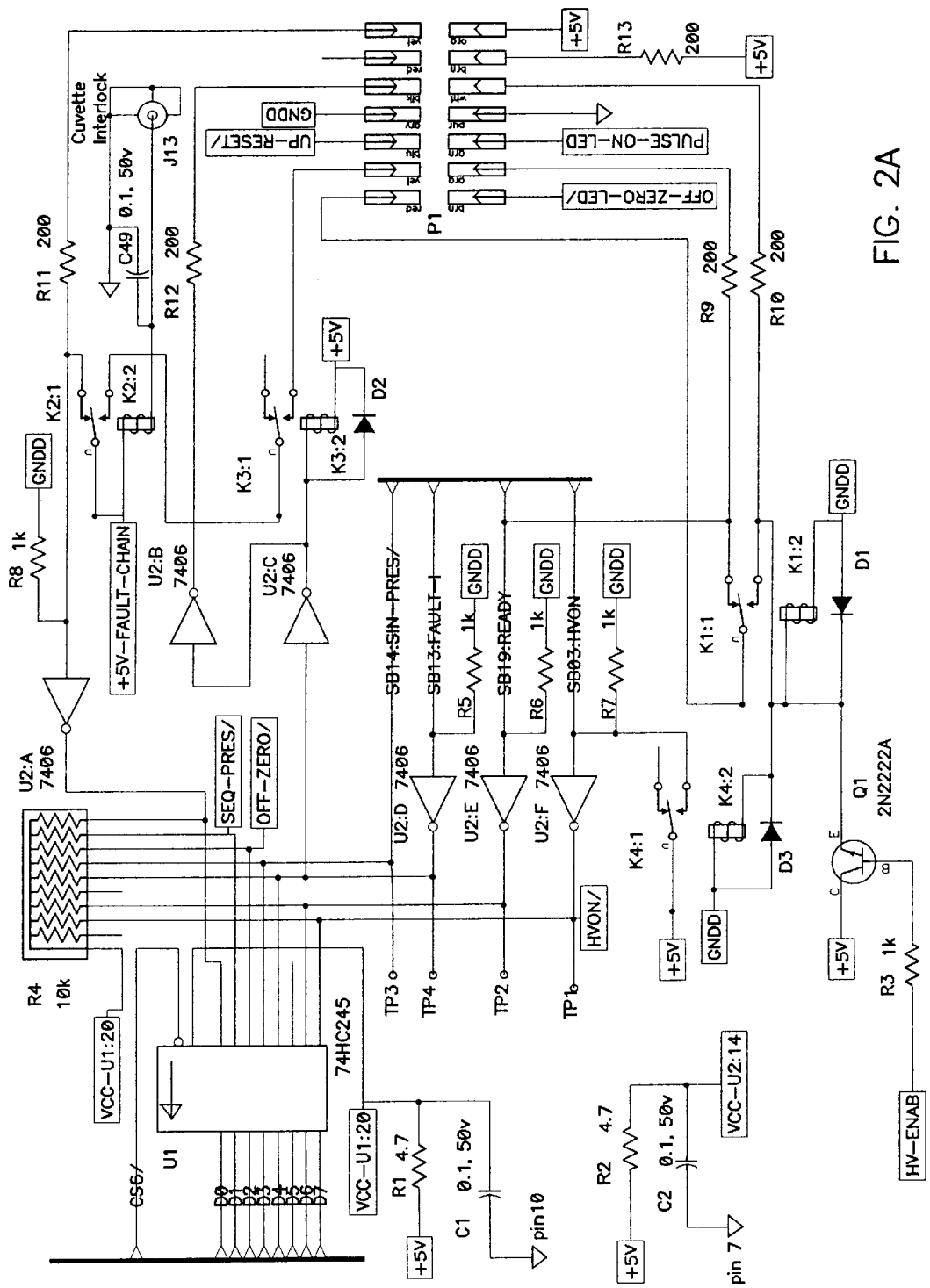
Figure 2B:
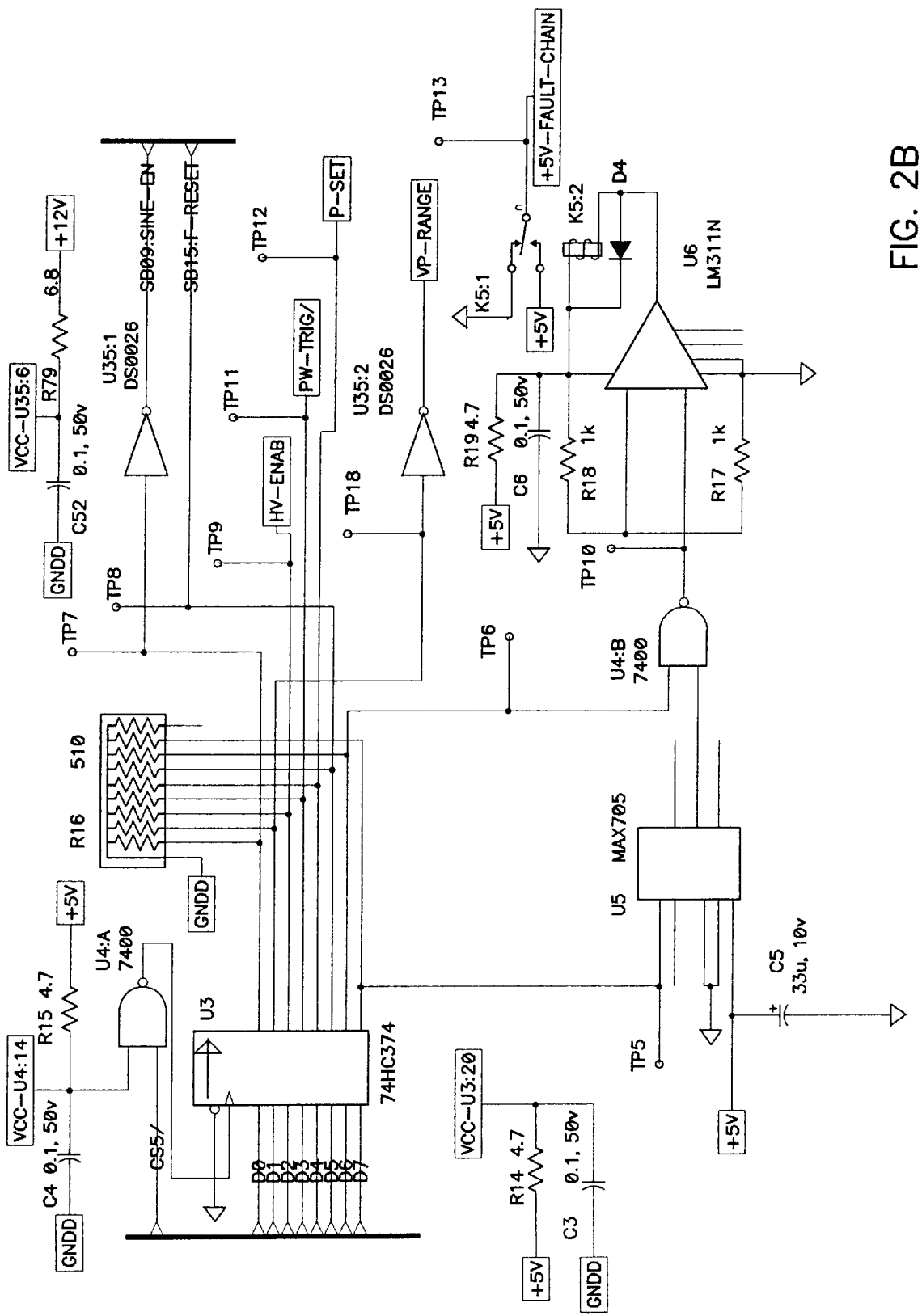
FIG. 2B is a circuit diagram of control from microprocessor (OUT).
Figure 2C:
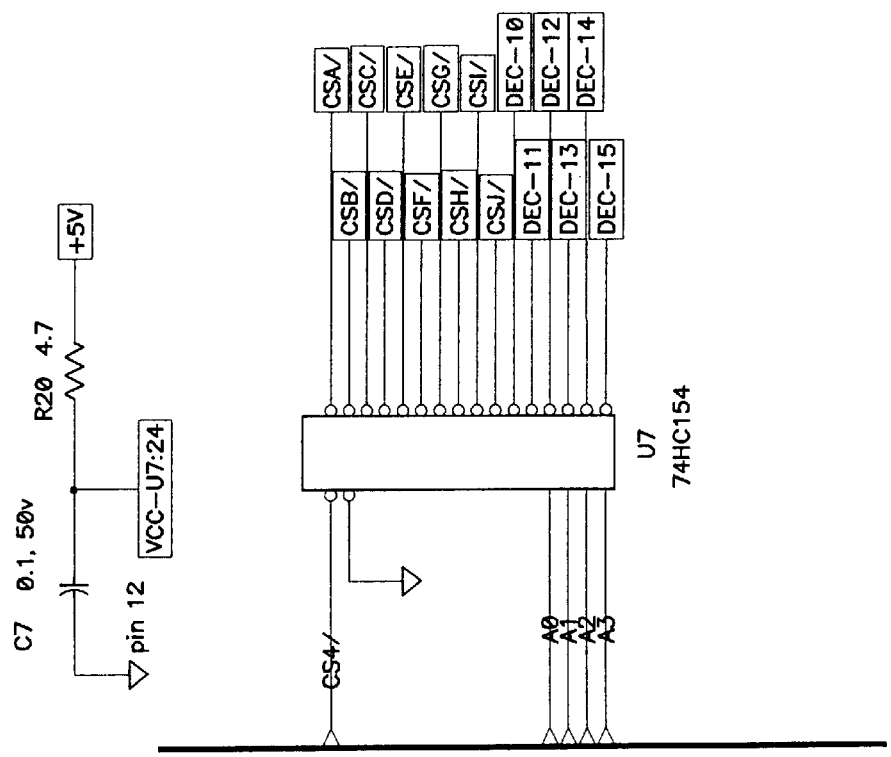
FIG. 2C is a circuit diagram of Chip Select Decoder.
Figure 2D:
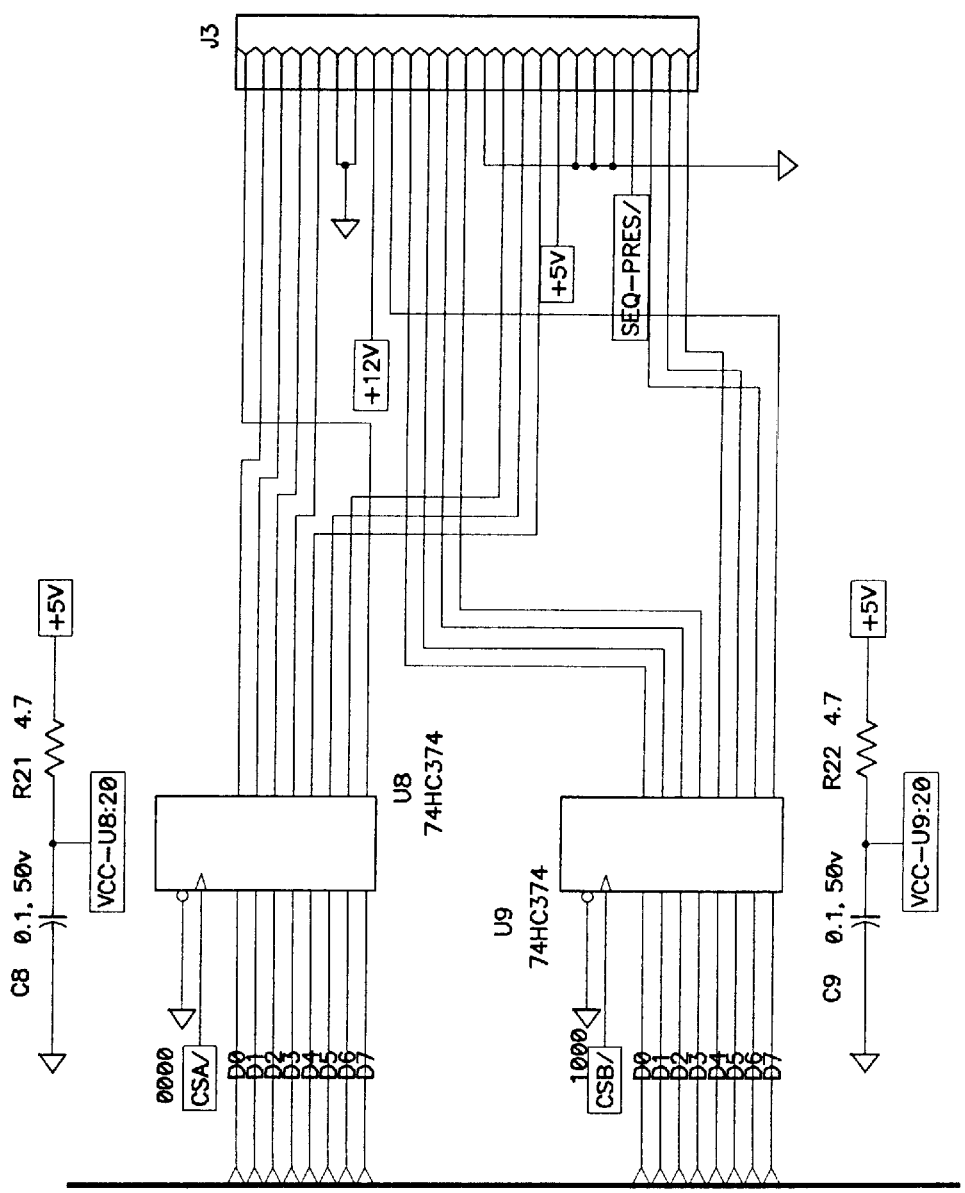
FIG. 2D is a circuit diagram of Pulse Router Interface.
Figure 2E:
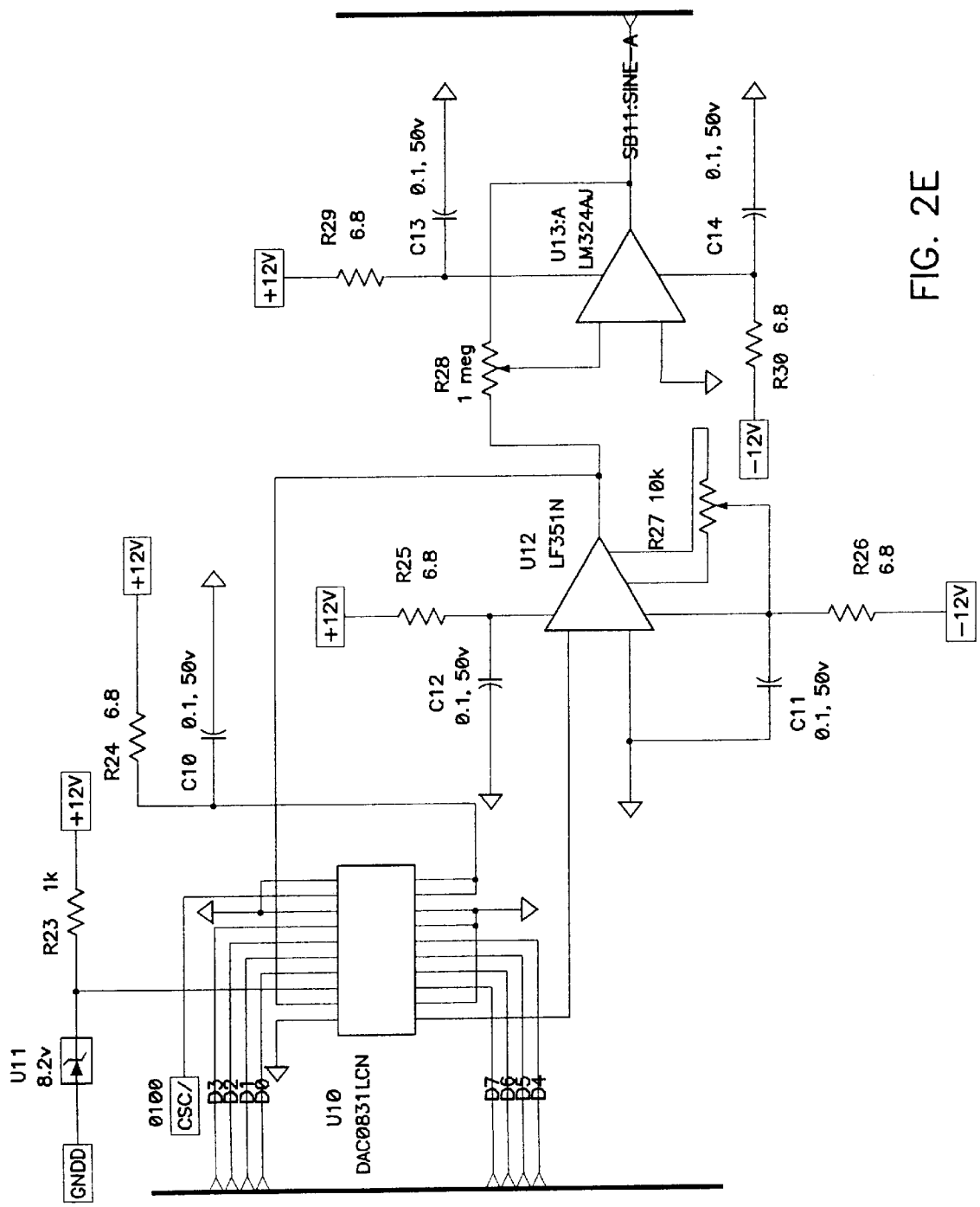
FIG. 2E is a circuit diagram relating to Sinewave Amplitude.
Figure 2F:
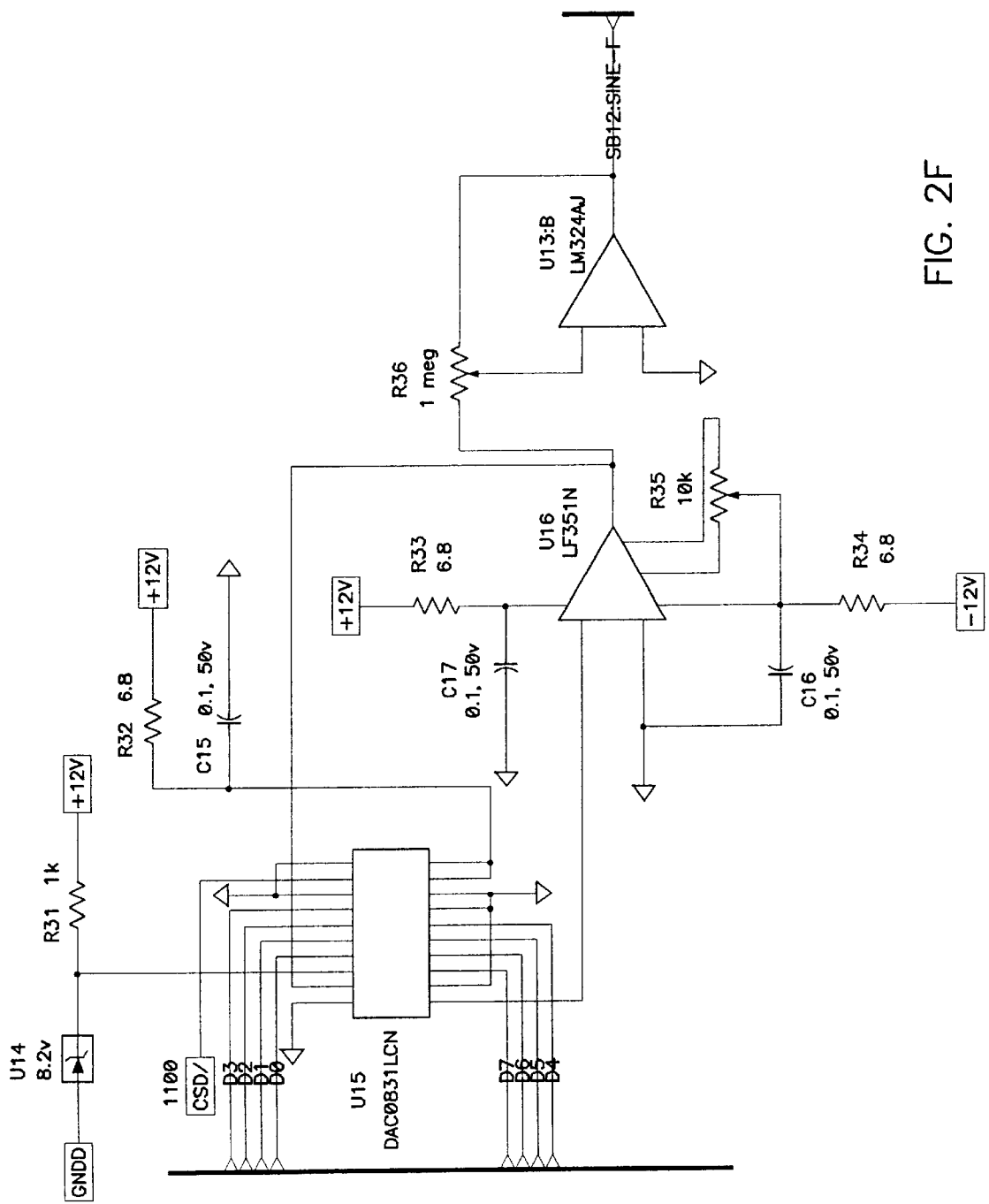
FIG. 2F is a circuit diagram relating to Sinewave Frequency.
Figure 2G:
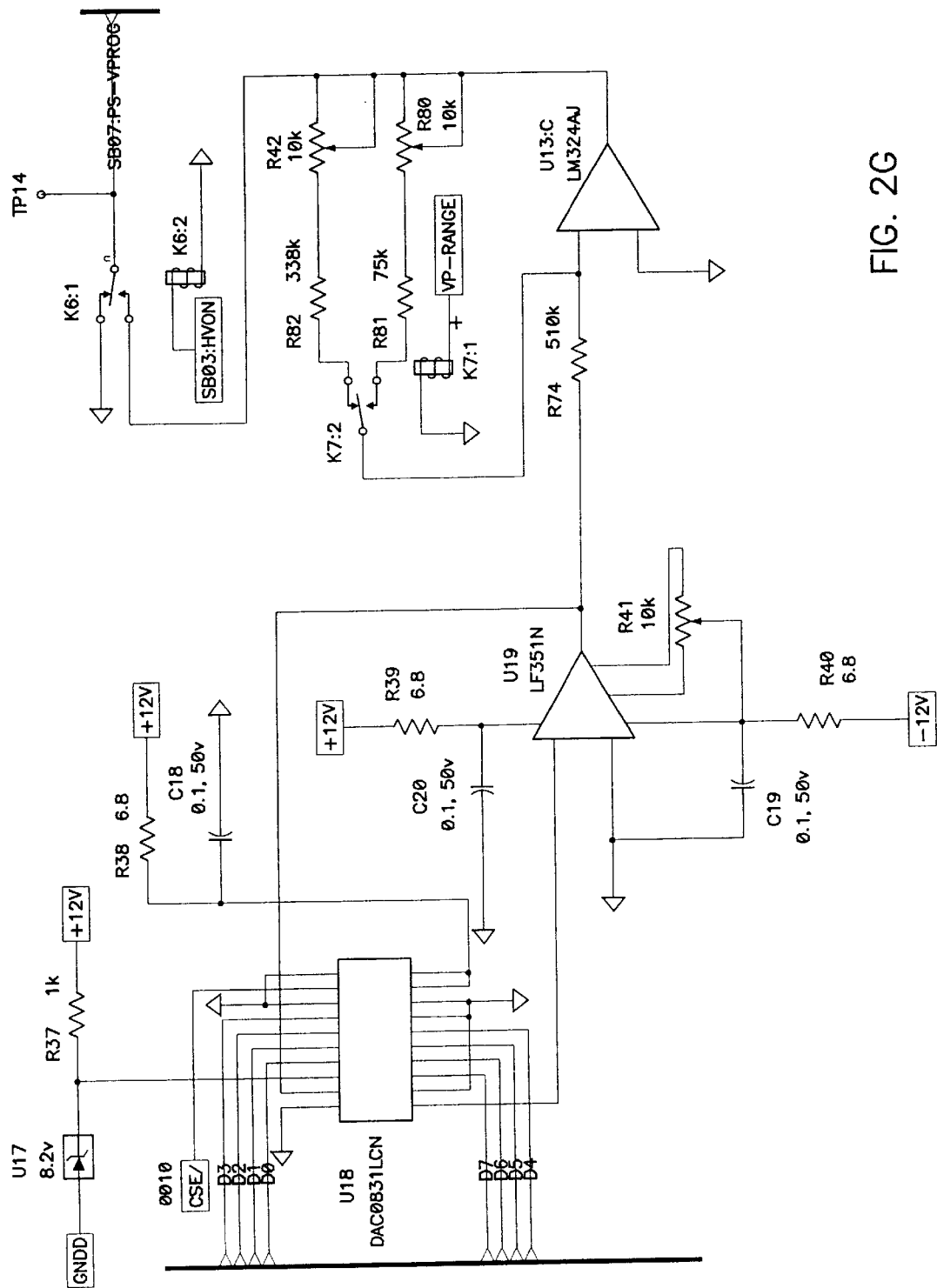
FIG. 2G is a circuit diagram of HV Power Supply Vprog.
Figure 2H:
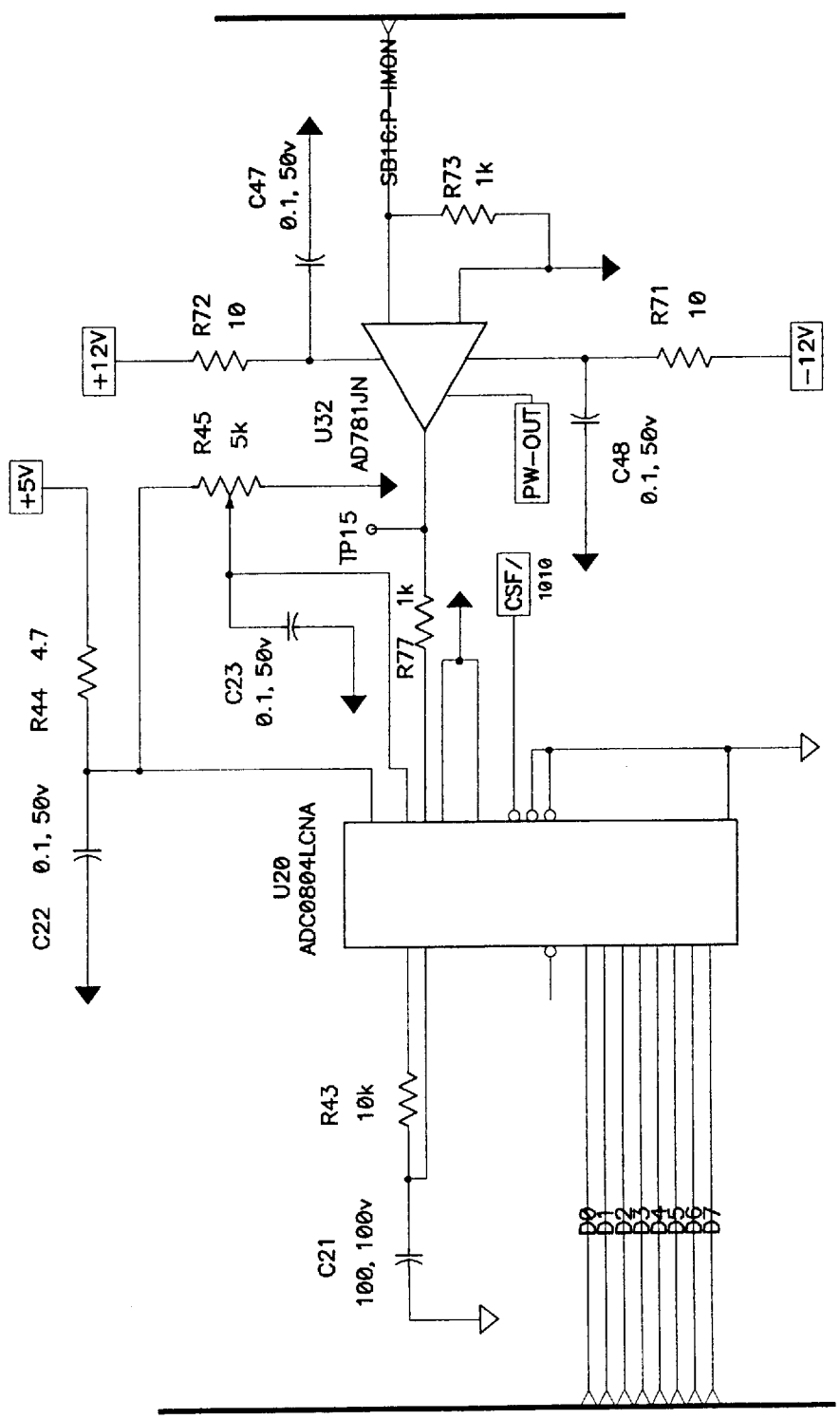
FIG. 2H is a circuit diagram of Pulse Current Monitor (P-IMON).
Figure 21:
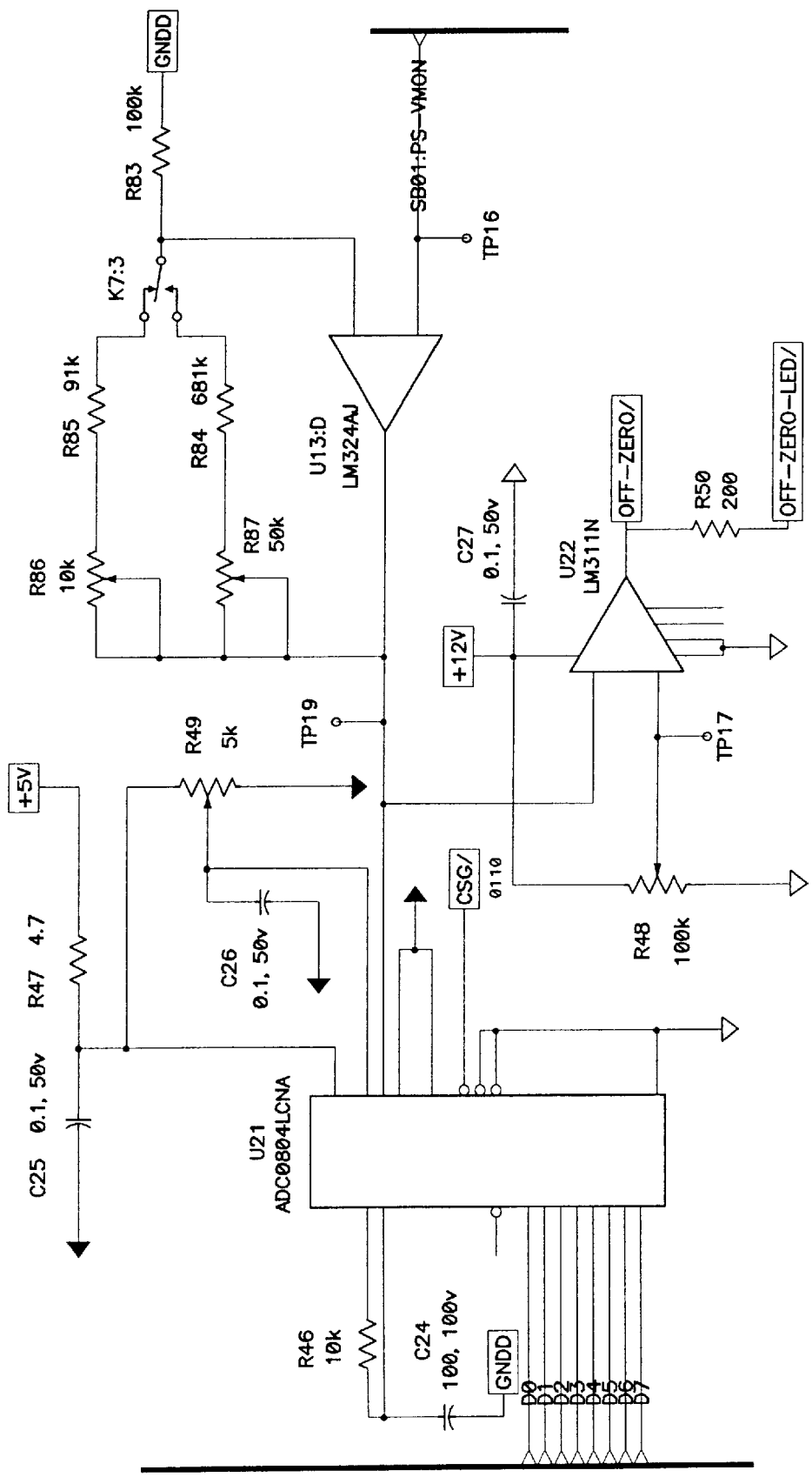
Figure 2J:
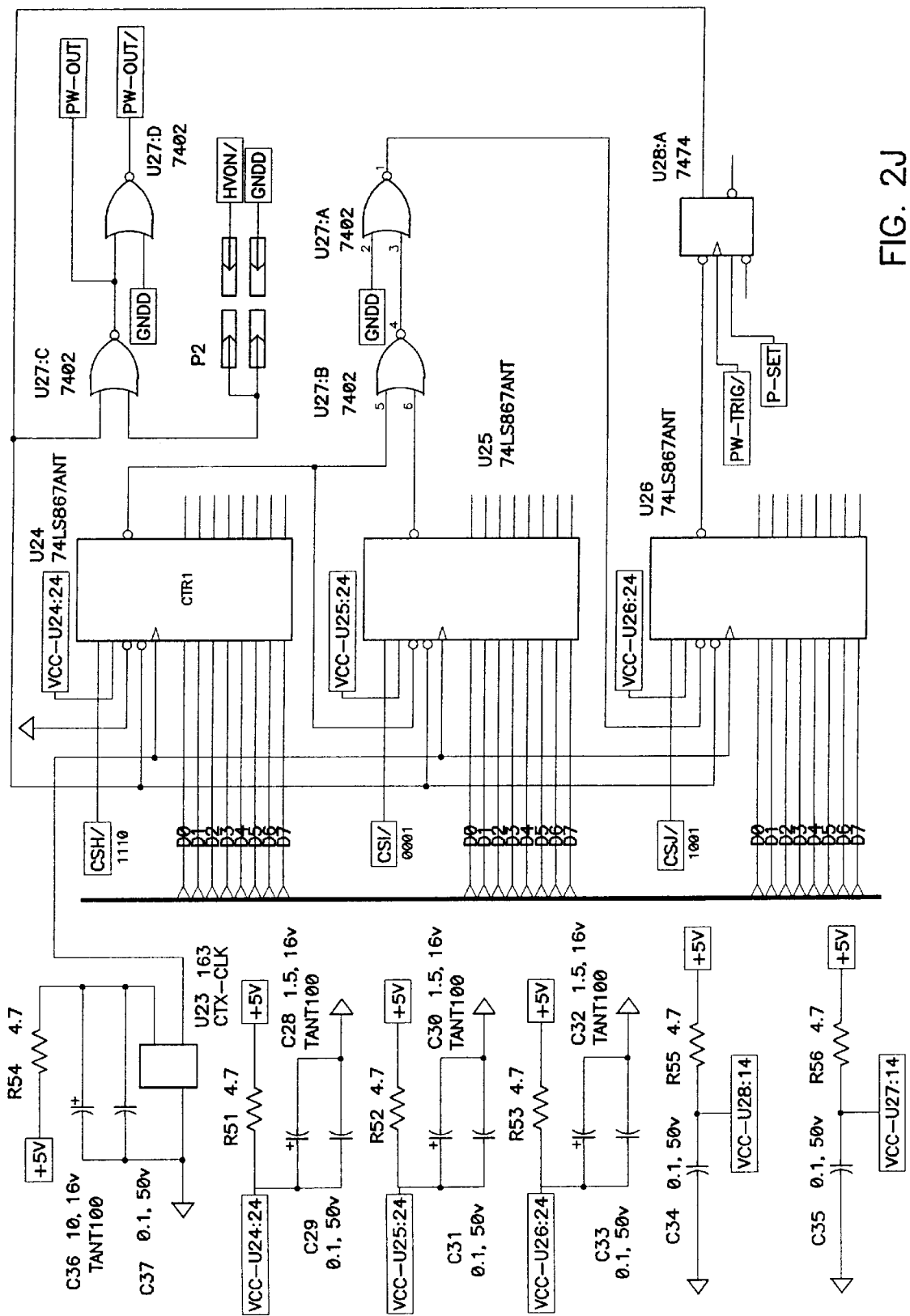
FIG. 2J is a circuit diagram of Pulse Width Counter.
Figure 2K:
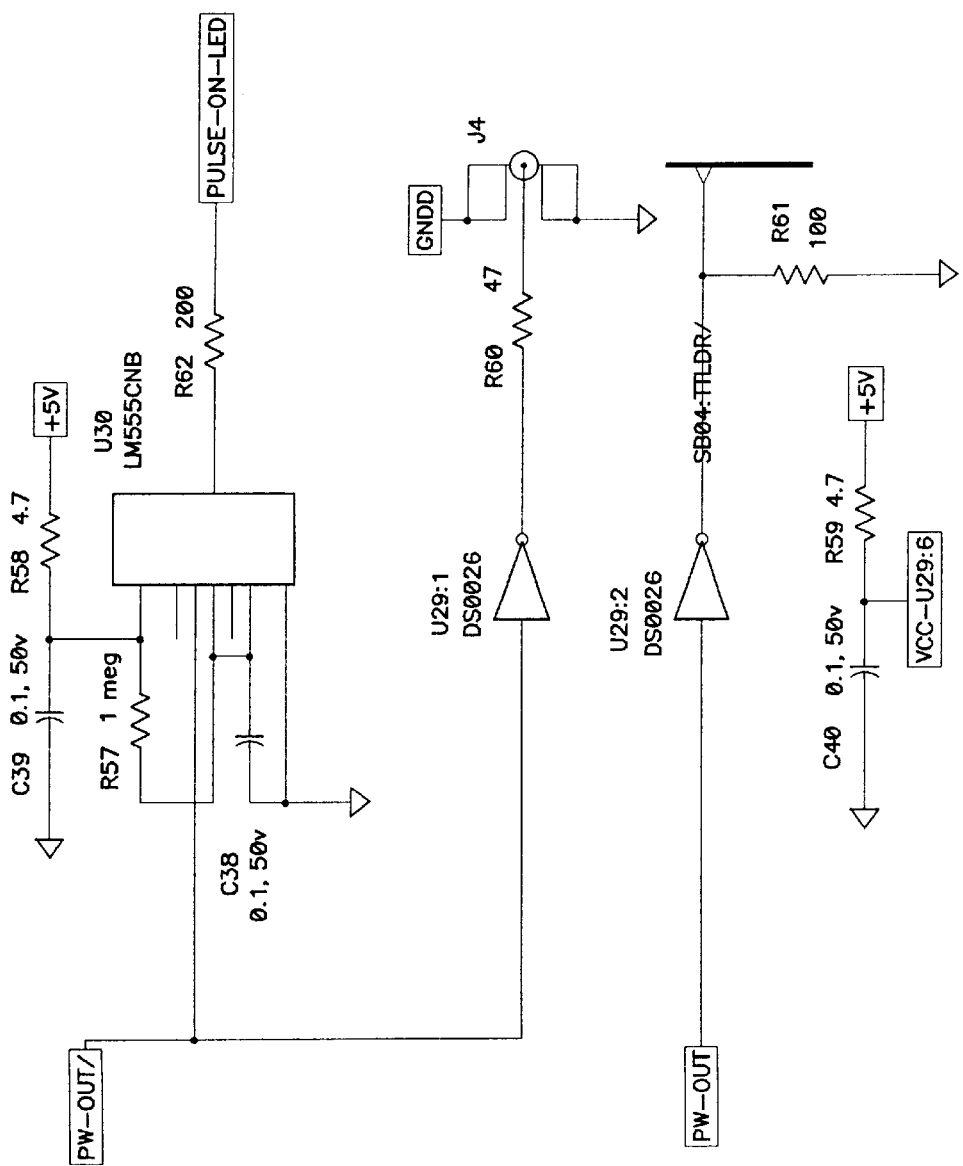
FIG. 2K is a circuit diagram of Pulse Out Drivers.
Figure 2L:
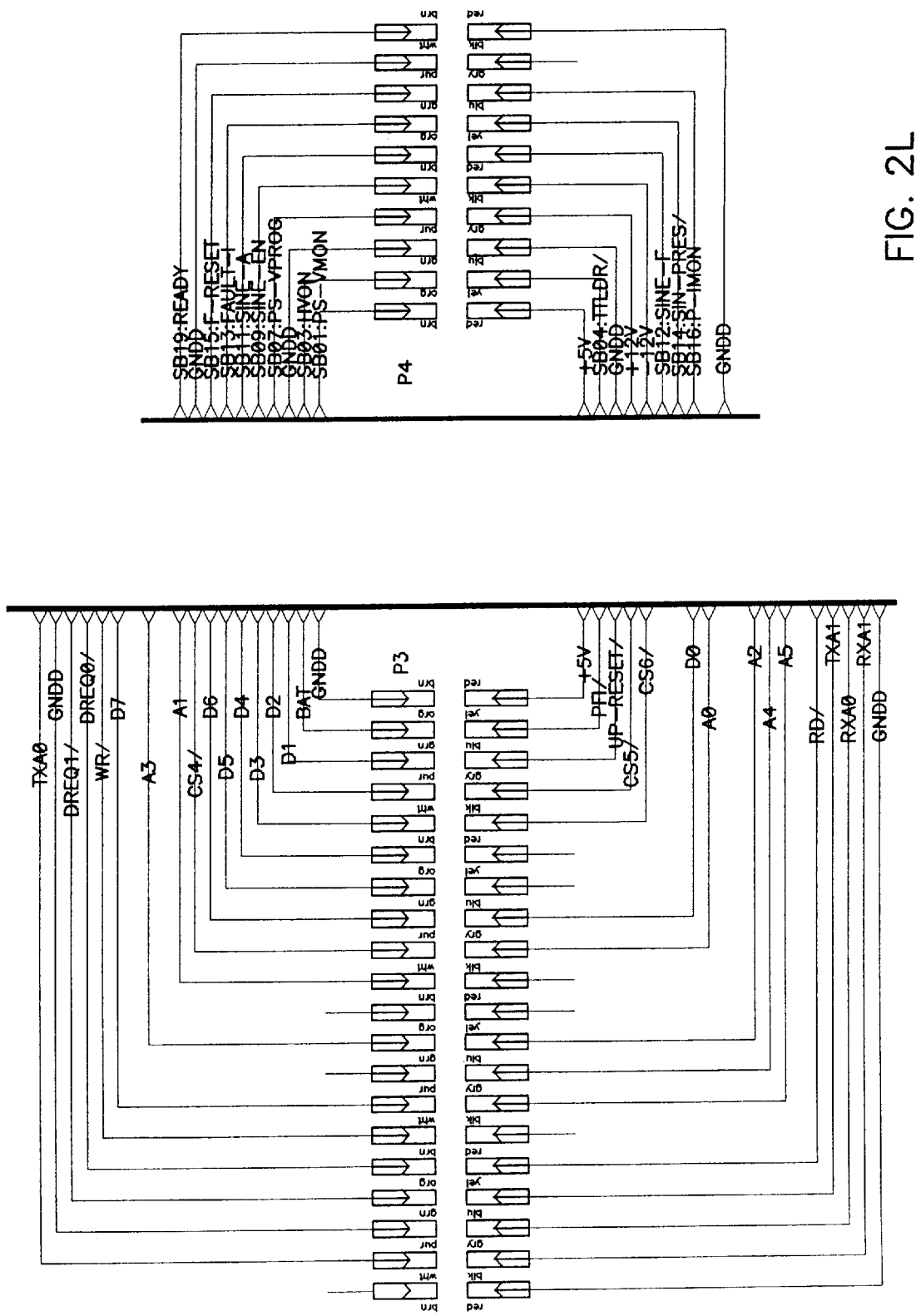
FIG. 2L is a circuit diagram of Bus Connectors.
Figure 2M:
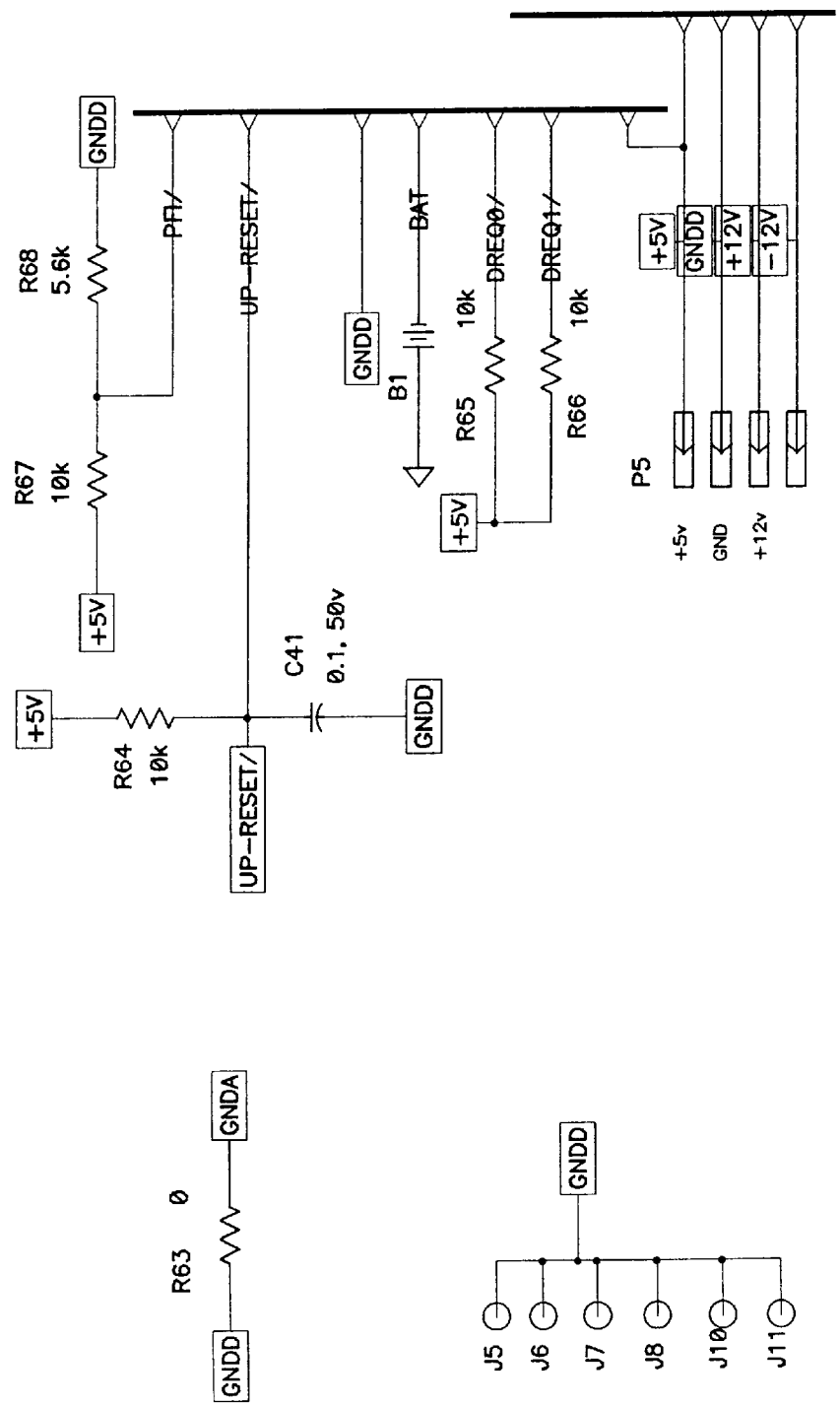
FIG. 2M is a circuit diagram of Power and Reset.
Figure 2N:
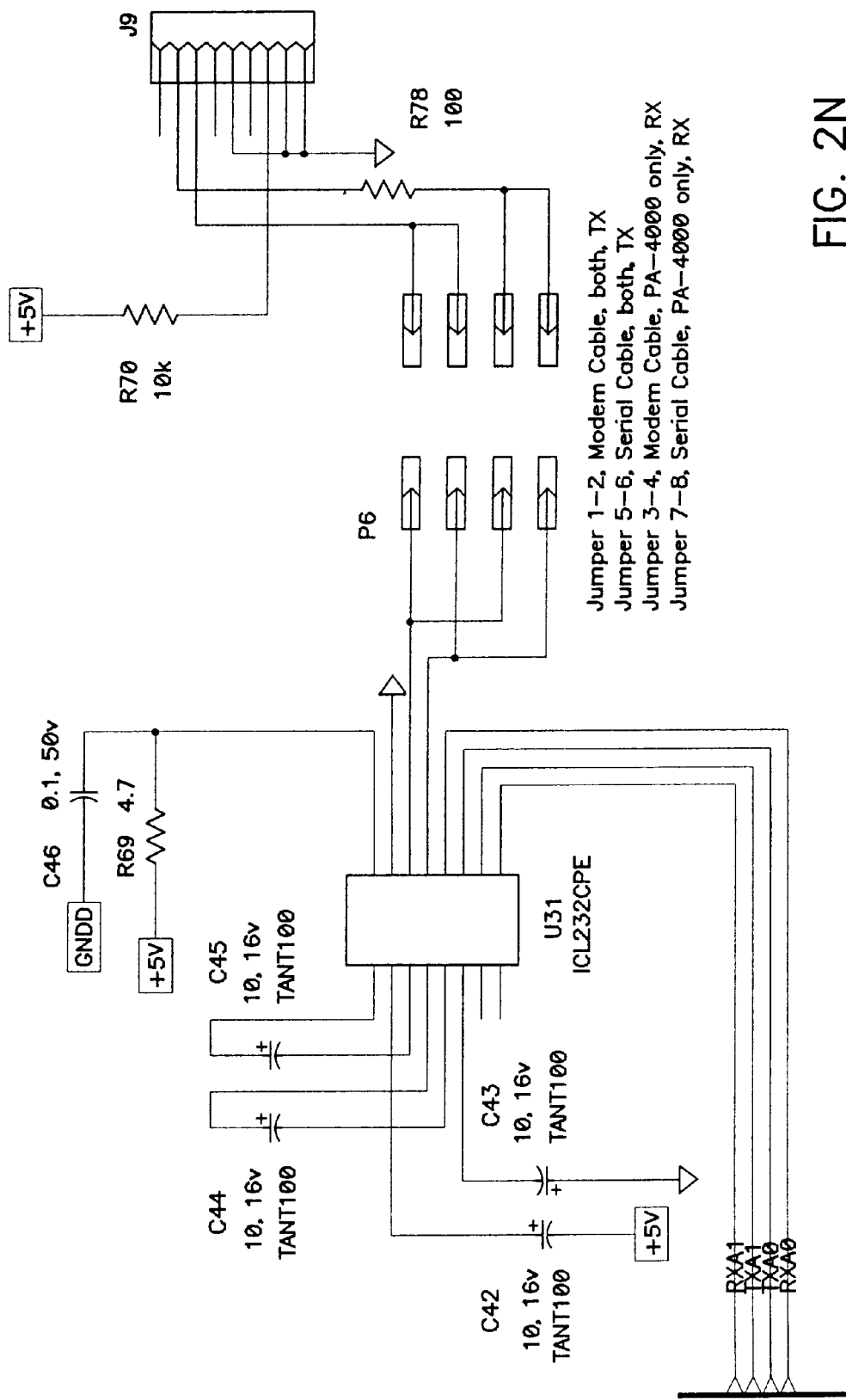
FIG. 2N is a circuit diagram of RS232.
Figure 20:
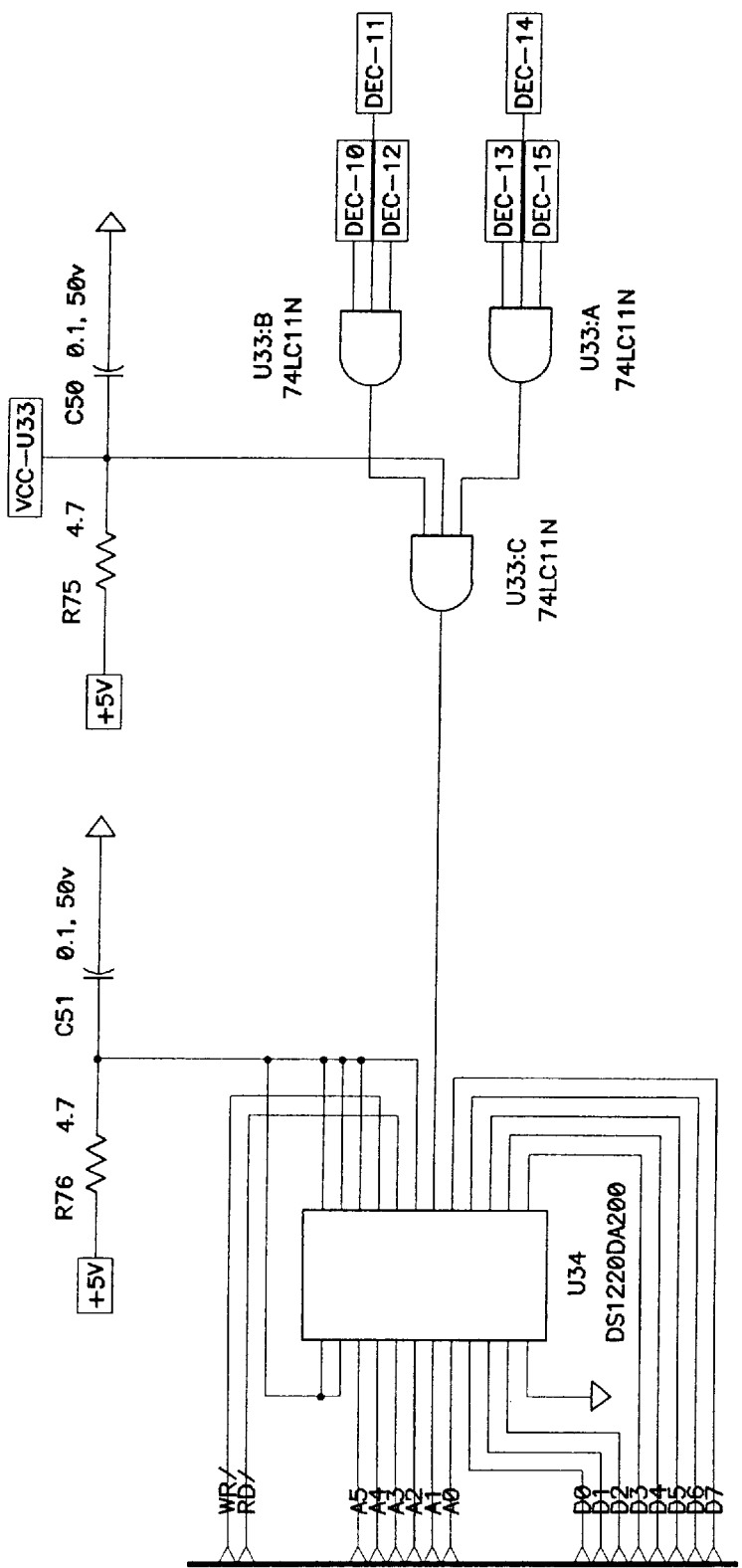

The Interface Control Assembly contains, the microprocessor, the analog to digital converts, digital to analog converters, high/low control and status line, pulse generator and programmable pulse switch interface, see FIG. 2

The microprocessor is connected to all other circuits via a 40 pin connector 19 Digital Bus 20. This bus contain 8 data line, 5 address line and 6 chip select lines. The data bus line transfer information to other circuit bases on the state of the chip select and address lines. A nonvolatile random access memory (NVRAM) part 18 is also connected to the Digital Bus 20. The NVRAM accumulates information on how many time the discharge relay is opened and closed and at what voltage it is opened and closed. This is information is printed out at the end of each protocol run and is used for failure analysis.

A Digital to Analog Converter (DAC) is used to convert the microprocessor 8 bit word into an actual voltage to set the power supply 22. This DAC output has a voltage range of 0 to 6 volts. This 0 to 6 voltage is carried over the Signal Bus 24 to the high voltage power supply. A 0 to 6 volt input to the high voltage supply 7 produces a 0 to 1100 volt high voltage output. There are two spare DAC connected to the Digital Bus.

An Analog to Digital Converter (A/D) 26 is used to convert the high voltage power supply output voltage monitor signal level of 0 to 5 volts into a digital word which is used by the microprocessor. A 0 to 1100 volt high voltage supply output results in the 0 to 5 volts monitor signal.

An Analog to Digital Converter (A/D) 28 is used to convert the pre-pulse current monitor signal monitor signal level of 0 to 2 volts into a digital word which is used by the microprocessor. This pre-pulse is generated by the microprocessor when the user starts the protocol. Before the high voltage is turned on a 9 (s, 2 volts pulses is generated. This pulse propagates through the load (cuvette, etc.). The current resulting from this pulse is converted into the 0 to 2 volt signal. This voltage is proportional to the load resistance. If the load resistance is too low (ionic concentration, etc. is too high) this can result in excessive current which could damage the material being porated. If the current is too high the microprocessor will not turn on the high voltage and will issue a "Load Current Too High" message.

There are several high/low control signal lines produced by the microprocessor 30. One is HVON (high voltage on) which is carried over the Signal Bus to the High Voltage Assembly, 6. Another control line, also carried over the Signal Bus to the High Voltage Assembly 6 is the Fault Reset line. This line is used to reset a latch if a fault occurs.

These are several status lines which are read by the microprocessor and used for control 32. One is a line from the Cuvette Holder 33. The Cuvette holder has magnet in the bottom. If the handle is slid open exposing the cuvette, this will break the contact. If this circuit is not closed, that is the handle push fully in, the microprocessor display a "Cuvette Open" message an the high voltage cannot be turned on, or if on will immediately be turned off. A second status line 34 is a contact in the Programmable Pulse switch. When the PPS parallel control cable is plugged in this line is grounded. This low line is then read by the microprocessor which indicated the PPS is available. A third line 34 is the Fault line. If a fault is detected in the High Voltage Assembly, this line goes high. The microprocessor is constantly monitoring this line and if it goes high a "Fault" message is display and the high voltage and pulse generator are immediate disabled.

The microprocessor control the low voltage pulse drive circuit 36. This circuit has a pulse width generator which is programmed by the microprocessor followed by a trigger signal which generates the pulse, the-next pulse width is then set followed by a trigger signal, etc. until all pulses have been generated.

The Programmable Pulse Switch interface 40 receives the setup commands from the microprocessor and sends the setup instructions via a special PPS parallel interface 9. This interface consists of a set of eight line which go high of a Pulse Out is programmed and a second set of eight line which goes high pulse return is programmed. If switch I to remain not connected than both line stay low.

Figure 3:
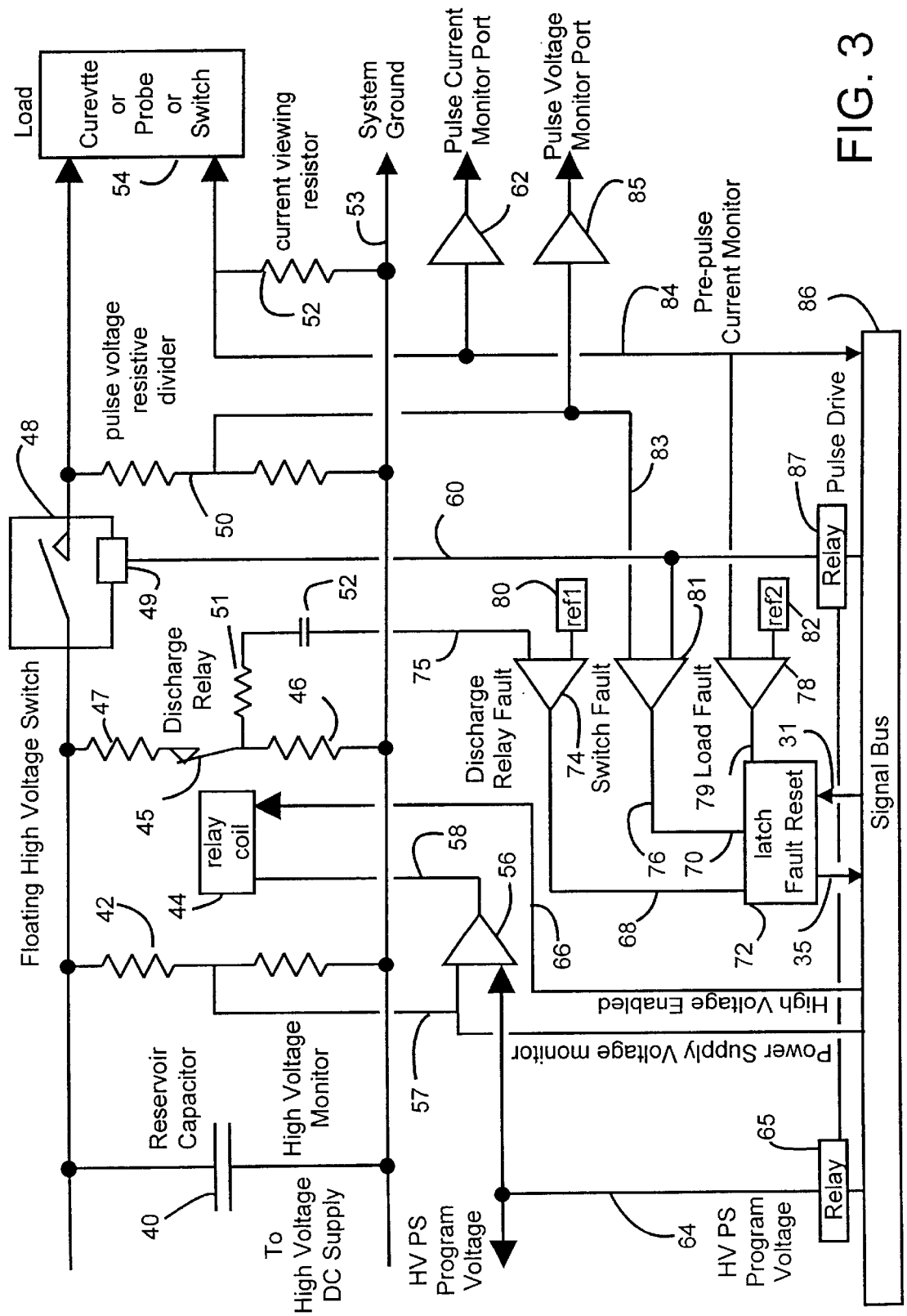
FIG. 3 is a circuit diagram showing major components of the high voltage assembly shown in FIG. 1.
Figure 3A:
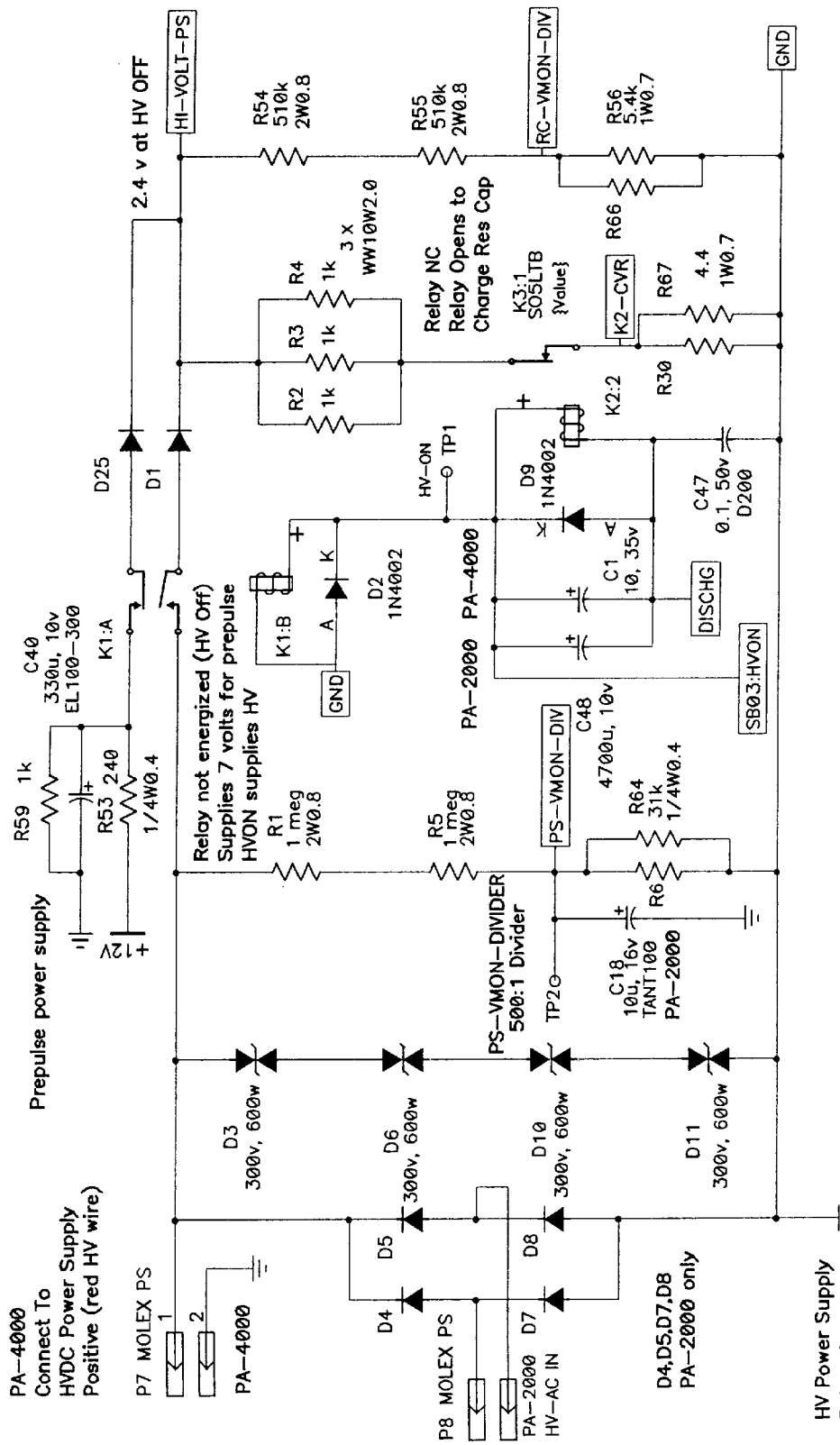
Figure 3B:
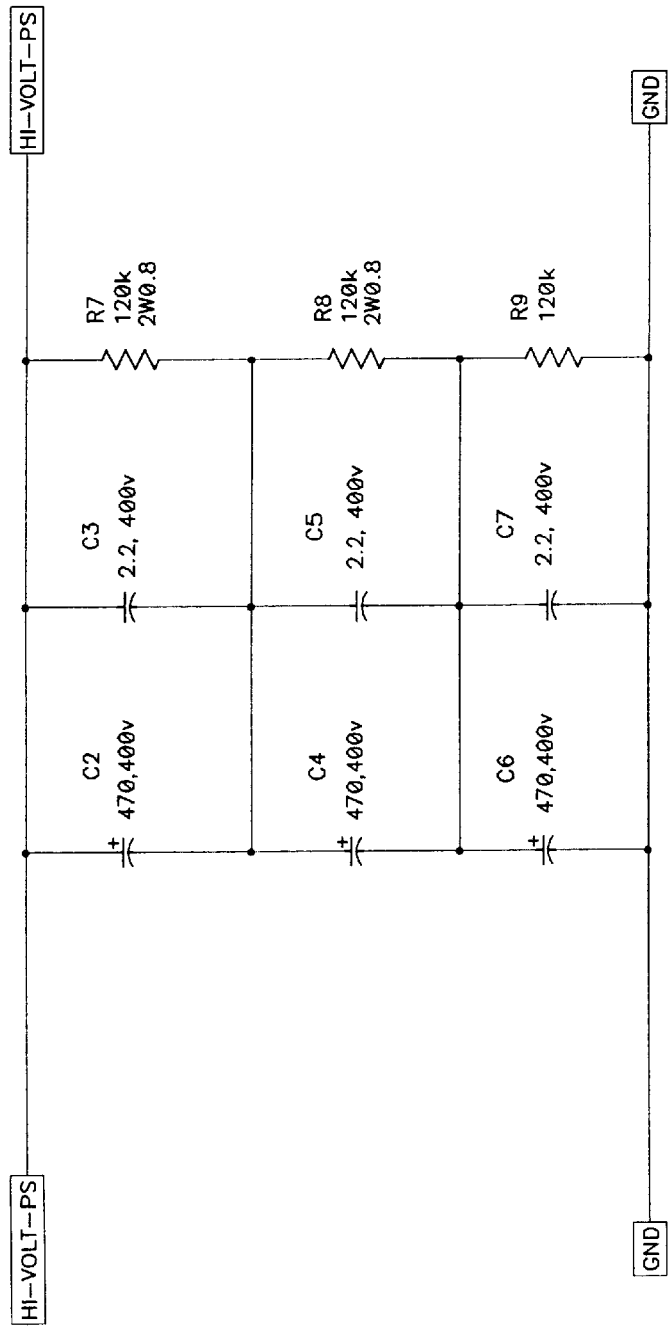
Figure 3C:
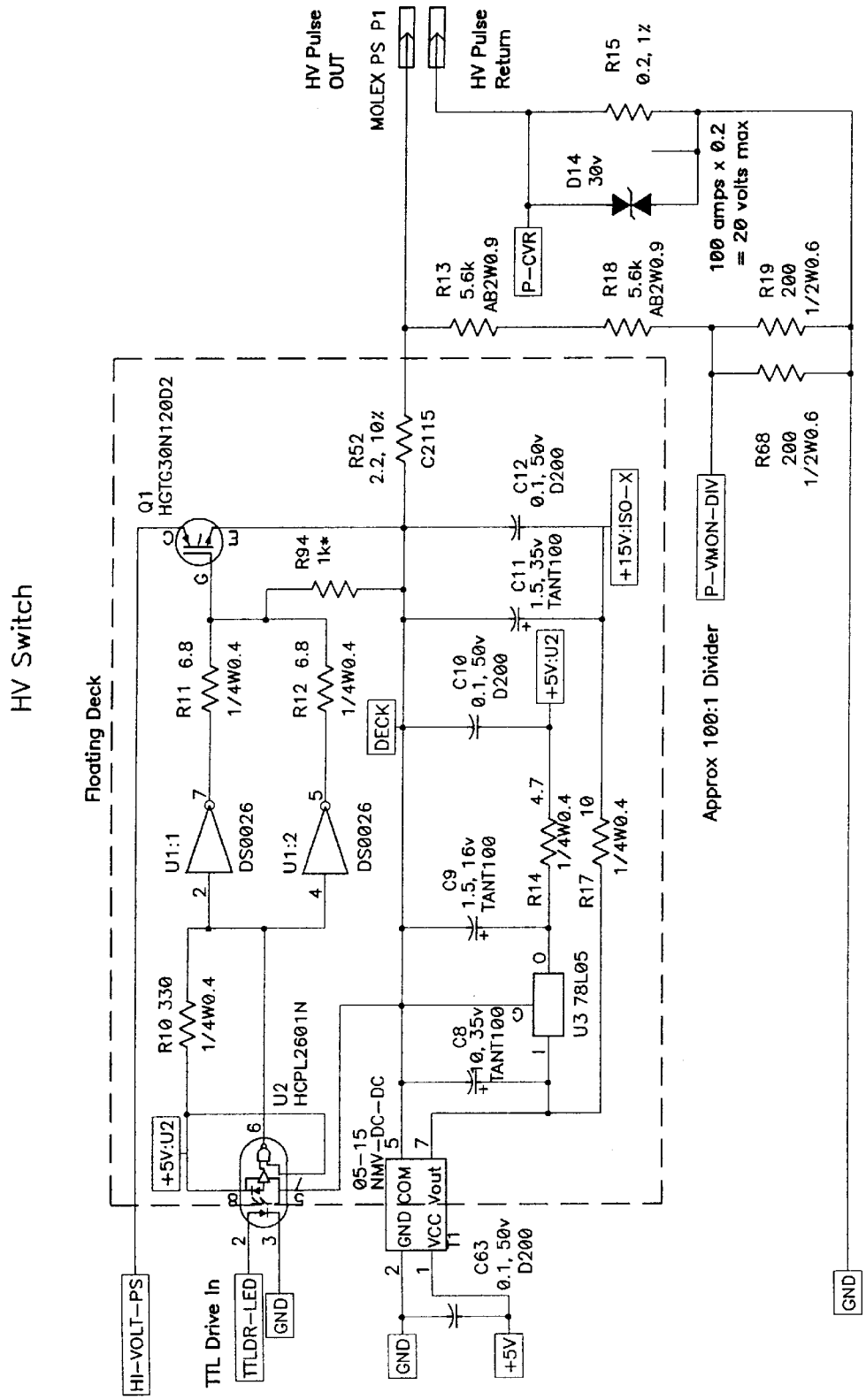
Figure 3D:
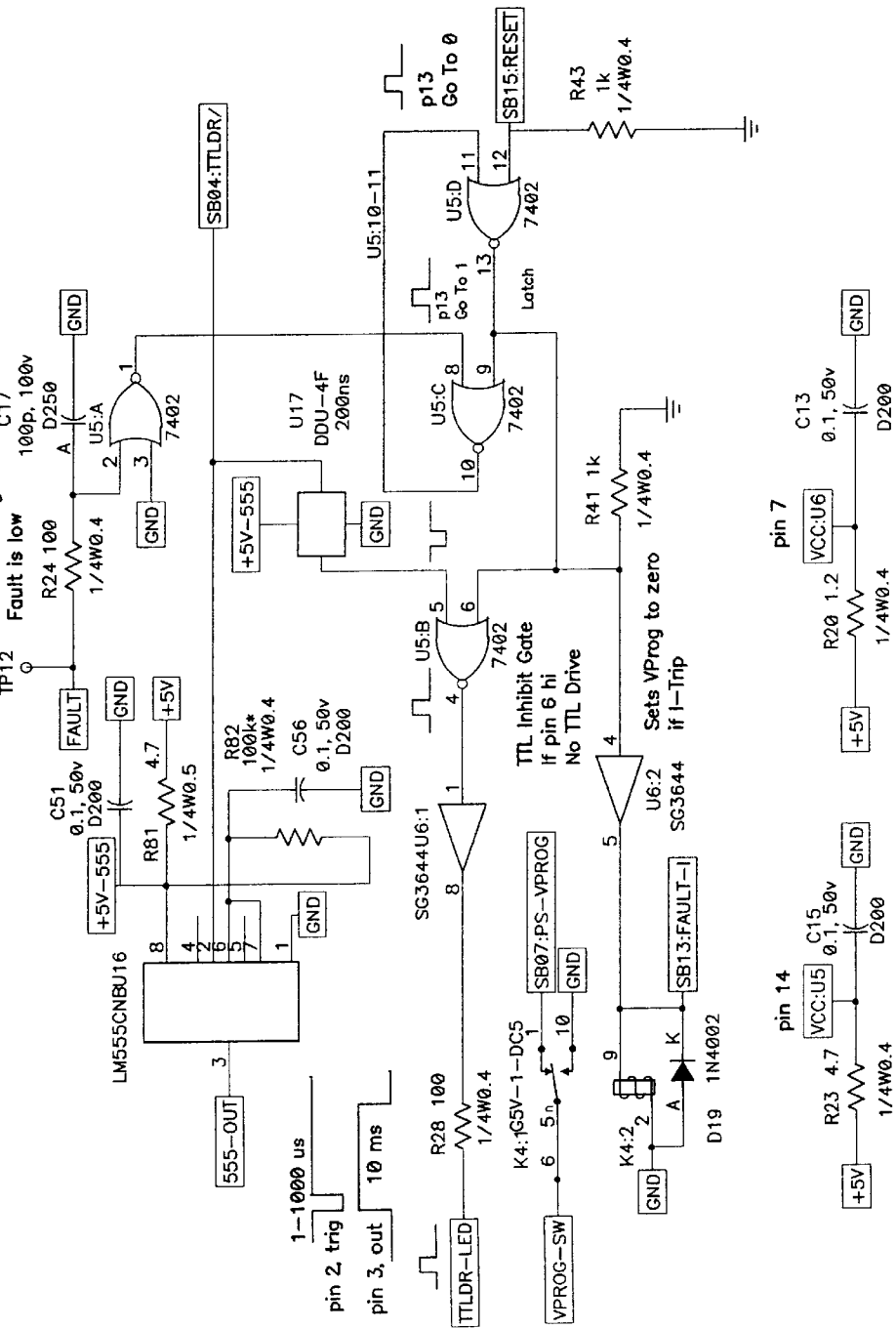
Figure 3E:
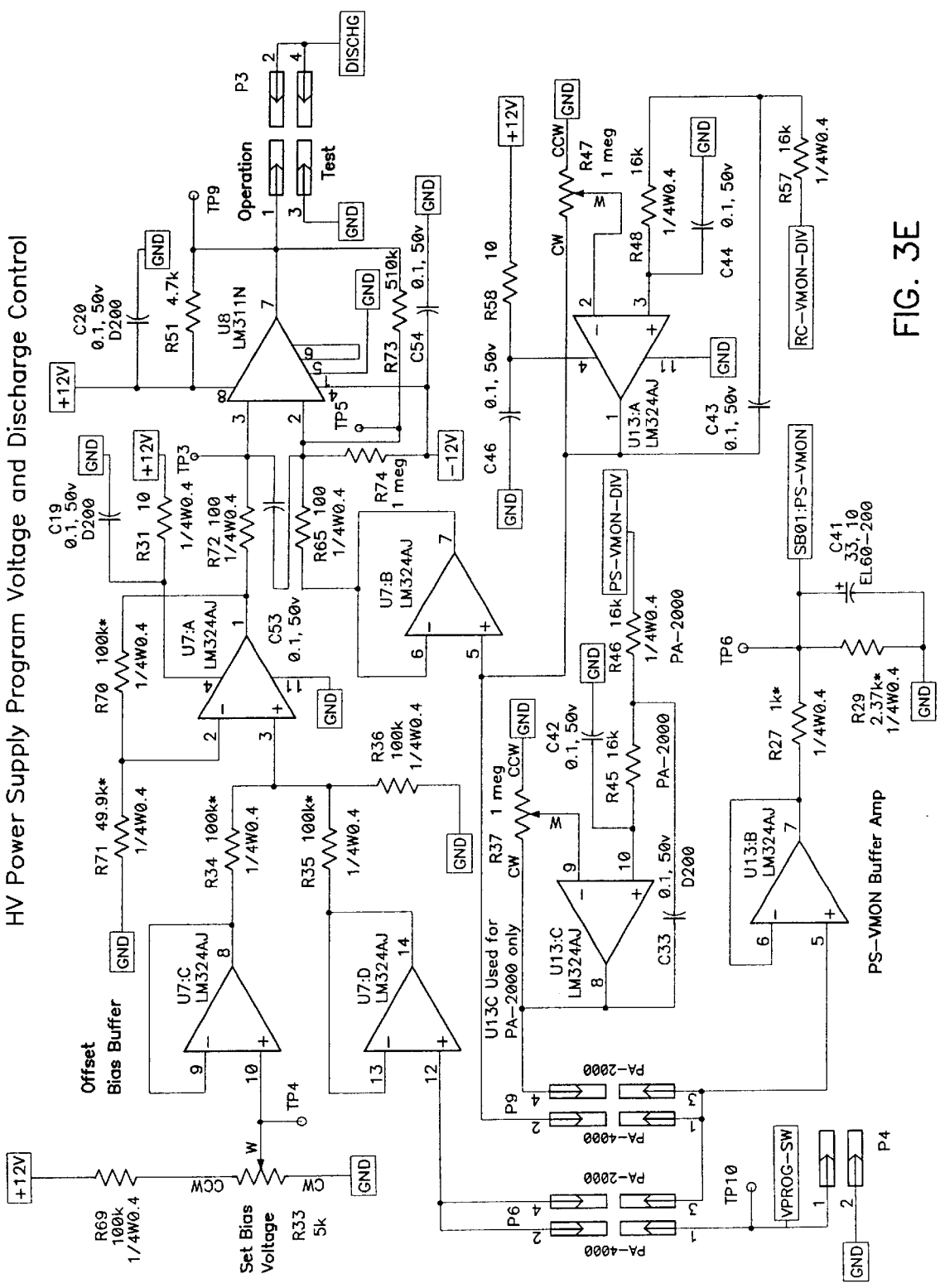
Figure 3F:
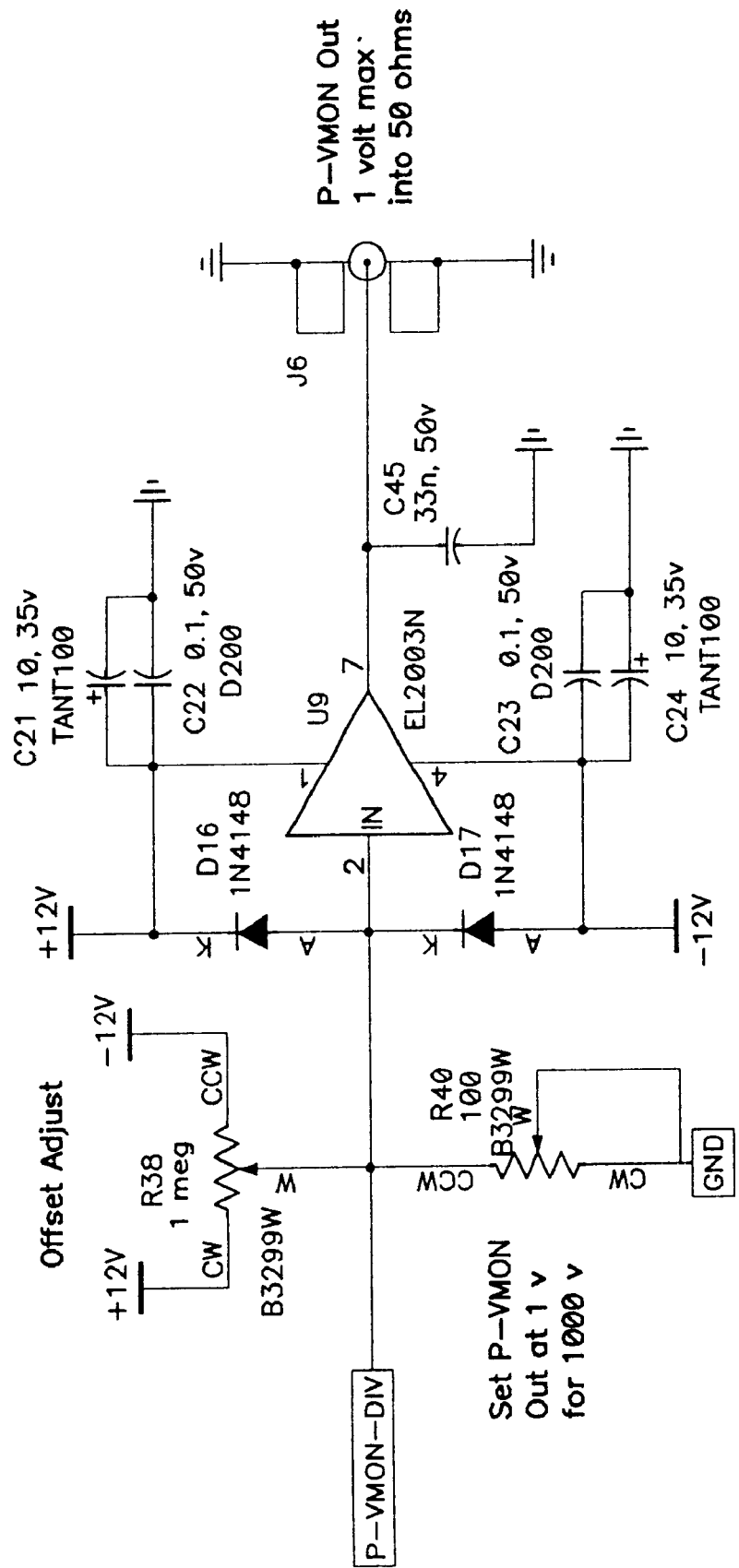
Figure 3G:
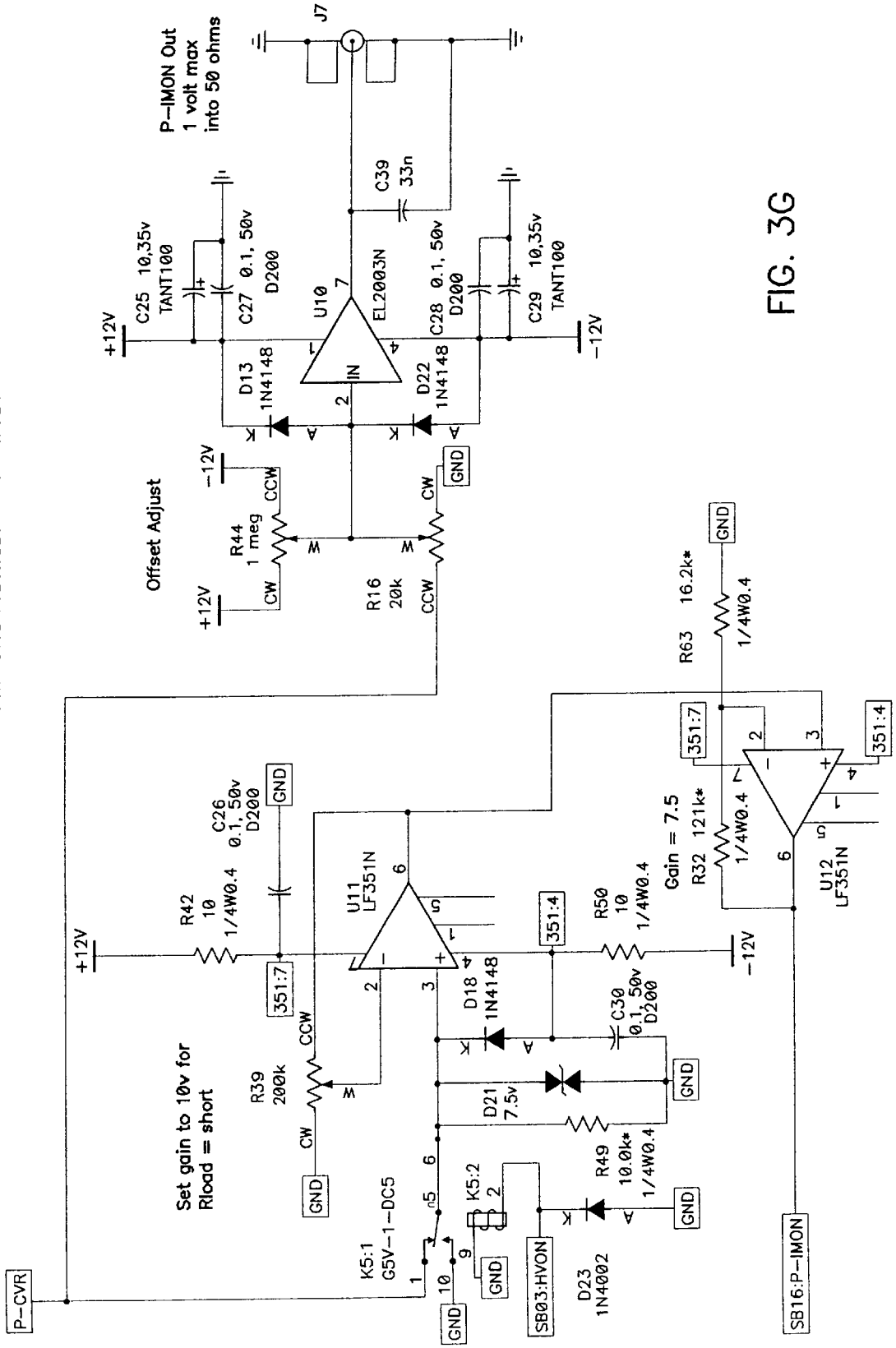
Figure 3H:
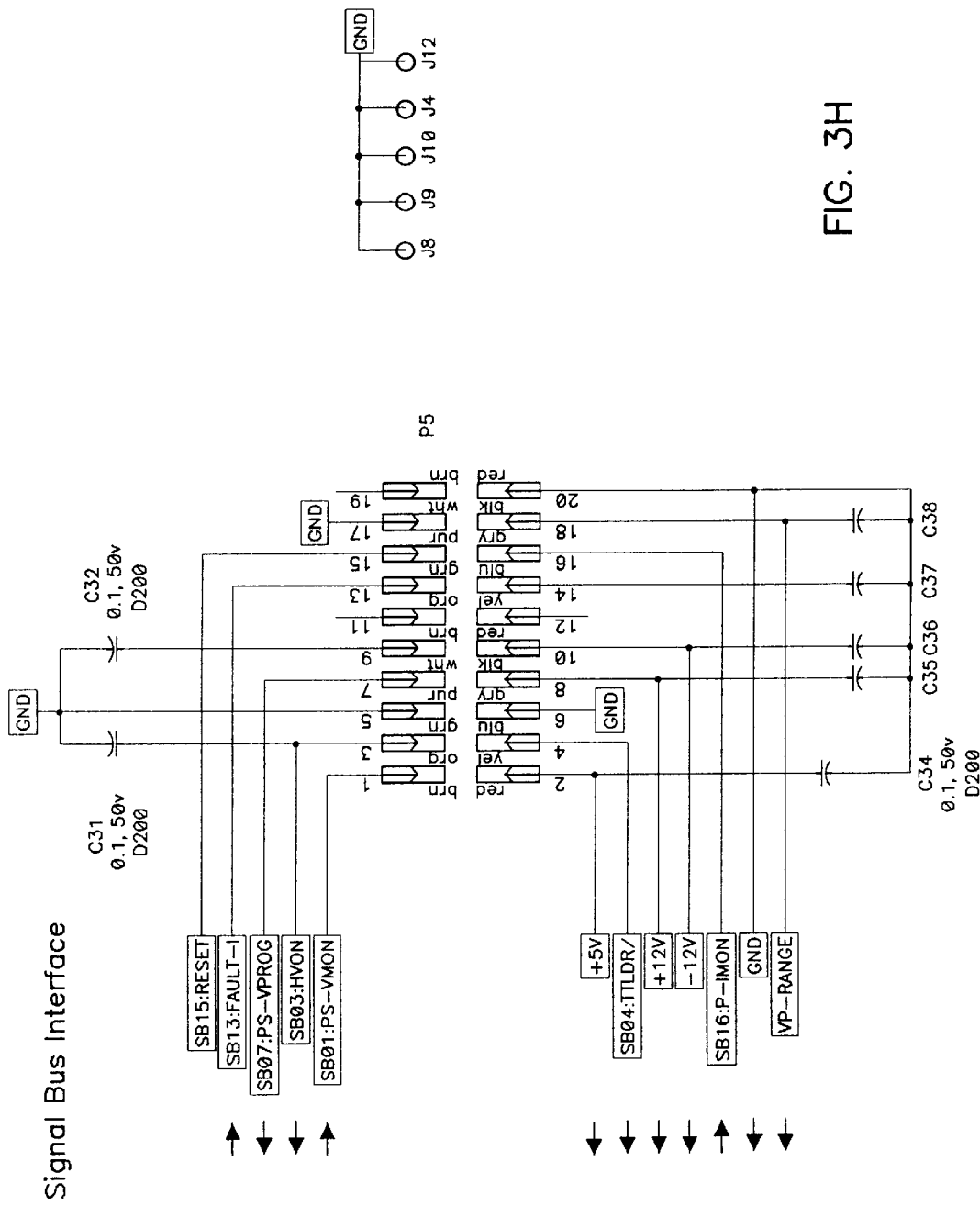
Figure 31:
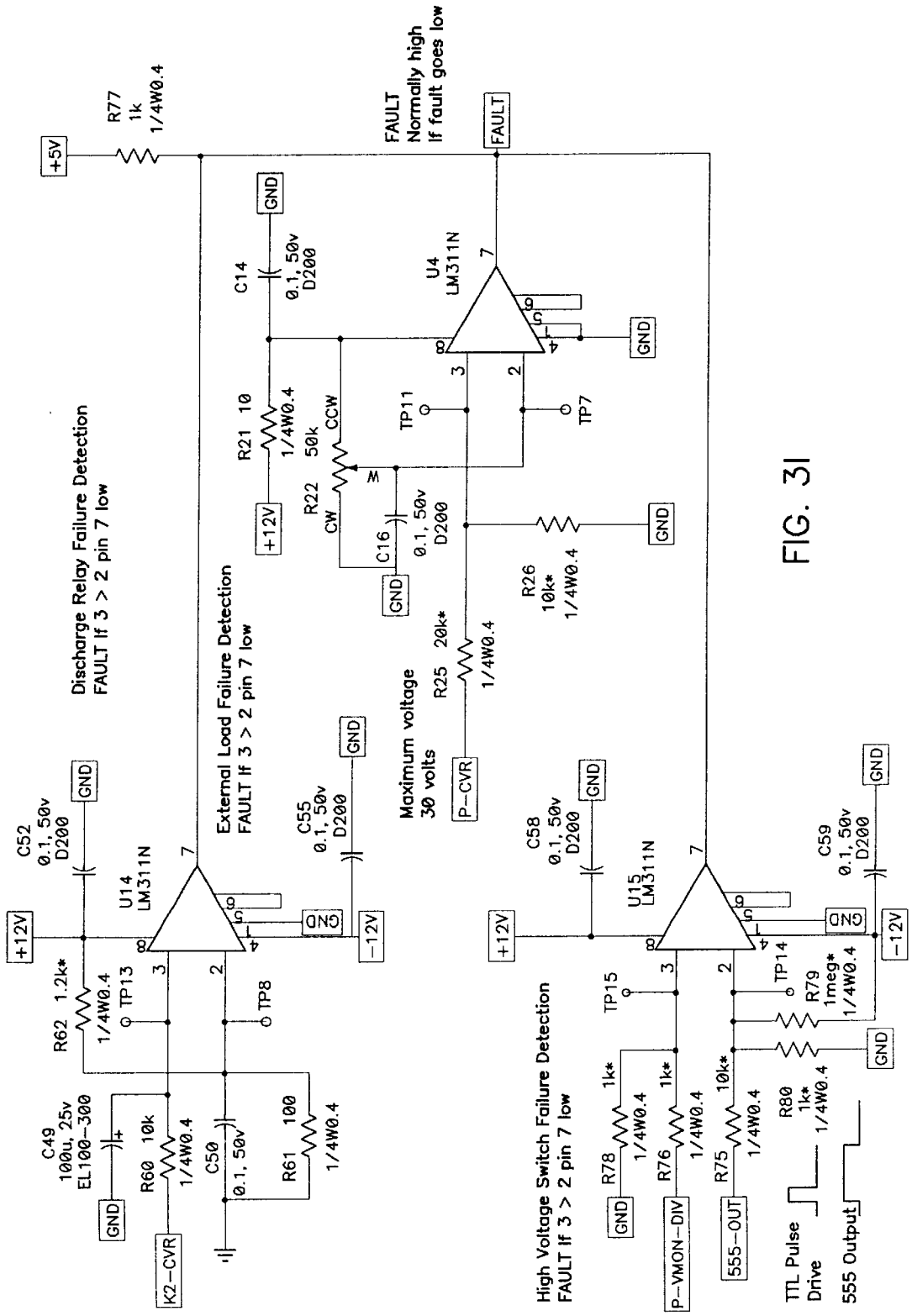

The High Voltage Assembly contains the high voltage switch circuit, the reservoir capacitor, power supply voltage monitor, pulse voltage and pulse current monitors, discharge relay and fault detection circuits, see FIG. 3.

When the high voltage is enabled the relay coil 44 is energized and the discharge relay 45 is opened. The power supply voltage program voltage is then set at the specified level. The high voltage supply then charges the reservoir capacitor 40. The floating high voltage switch 48 is then turned on by the pulse drive signal 60 via the Signal Bus. The low voltage signal is connected to the floating high voltage switch via an opto isolator 49. When the high voltage switch is turned on current from the reservoir capacitor flows through the load 54, the pulse current monitor viewing resistor 52 to System Ground 53 which is connected to the power supply ground completing the current path. The resistive voltage divider 42 produces a low voltage signal proportional to the high voltage across the reservoir capacitor 40. This scaled voltage 57 is connected to the Signal Bus and read periodically by the microprocessor.

The scales version of the pulse current is produced by the pulse current flowing though the current viewing resistor 52. This voltage which is approximately 20 volts for 100 amps, is buffer by amplifier 62. This is the Pulse Current Monitor Port. The scaled pulse voltage is produced by the resistive voltage divider 50. This voltage is then buffered by amplifier 85. The output is the Pulse Voltage Monitor Port.

In the PA-4000 the pulse amplitude may be changed from pulse to pulse, that is changed from 1100 voltage (maximum) to 50 volts (minimum) on the next pulse which can occur is as little time as 125 milliseconds. This is accomplished by the Discharge Relay Circuit 44, 45, 46, 47, 56, 57, 58. A voltage comparator 56 compare the voltage between the high voltage power supply program voltage 64 and the scaled voltage on the reservoir capacitor 57. If the high voltage power supply program voltage 64 is greater than or equal to the capacitor scaled voltage 57 then the comparitor out 58 is low. When the output 58 is low and the high voltage is enabled, the opposite side of the relay coil is high 66. This differential voltage across the relay coil 44 energizes the coil 44 and opens the relay 45. If the high voltage power supply program voltage 64 is lower than the scaled voltage on the reservoir capacitor 40, the output of the comparitor 58 goes high. If 58 is high and the other side of the relay coil 44 is high 66 (high voltage on) then there is no voltage across the relay coil 44 and the relay closes 45. When the relay 45 closes the reservoir capacitor 40 is connected to system ground 53 through resistor 47. This total current during discharge is limited by resistor 47 to prevent the relay contacts from welding. The time constant between the reservoir capacitor 40 and resistor 47 can reduce the voltage across the capacitor by 95% in 50 milliseconds which is half the time of the minimum pulse interval. If the power supply program voltage 64 is set at voltage which results in, for example 400 volts, out of the power supply 7 the comparitor will go high 58 when that voltage is reached and the relay 45 will open and the Reservoir Capacitor 40 will not discharge any further. Thus the voltage on the Reservoir Capacitor 40 may be set rapidly to any level between the maximum and minimum within the shortest pulse interval.

There are three fault detection circuits in the high Voltage assembly, high voltage switch 60, 83, 81, 76, discharge relay 75, 80, 74, 68, and load 84, 82, 78, 79. All three are connected to a latch circuit 72. If any of one of the three line 68, 76, 79 go low the latch out 35 will go high. If 35 goes high the program voltage 64 is disconnected via relay 65 and the pulse drive is disconnected via relay 87 in hardware. The microprocessor constantly monitors the latch out 35 and if it goes high a "Fault" message is displayed. The system may be reset from the PC which momentarily bringing the rest line high 31.

The relay discharge fault circuit 75, 80, 74, 68 monitors the proper operation of the discharge relay 45. If the relay 45 fails and connects the power supply 7 and reservoir capacitor 40 through resistor 47 to ground 53 continuously, damage to the internal circuits could occur. If the relay 45 does fail and remains closed, current through viewing resistor 46 will produce a voltage which will integrate up by RC combination 51, 52 until it is 75 larger than the comparitor reference voltage 80. This takes a few milliseconds if the high voltage power supply 7 is set to maximum voltage.

The high voltage switch fault circuit 60, 83, 81, 76 monitor the proper operation of the high voltage switch. This circuit is to insure that no high voltage appears at the load 54 if the high voltage switch 48 fails shut continuously. If that happens and the high voltage power supply 7 is turned on a voltage will appear at the scale pulse voltage resistive divider 50. This voltage 83 is compared to the presence of the drive pulse. Without a drive pulse 60 the output of the comparitor 81 goes low if 83 is more than 10 volts within 1 (s. This is vary rapid and the power supply does not have time to turn on.

The load fault circuit 84, 82, 78, 79 monitor the current through the load 54. If the load current becomes excessive while the high voltage pulse is on pulse is on due to break down in the cuvette, etc., the contents of the cuvette could vaporize or internal circuits may be damaged. If the current becomes excessive the voltage across the viewing resistor 52 increase above the threshold vale 82. When the reference is exceed the output of the comparitor 79 goes low in less than 1 (s.

The high voltage power supply 7 is a commercial unit which delivery 110 ma at 1100 volts and is programmed with a 0 to 6 volt signal. The low voltage power supply 8 provides voltage to all control circuits, +5 volts, +12 volts, −12 volts. It is a commercial unit.

Figure 4:
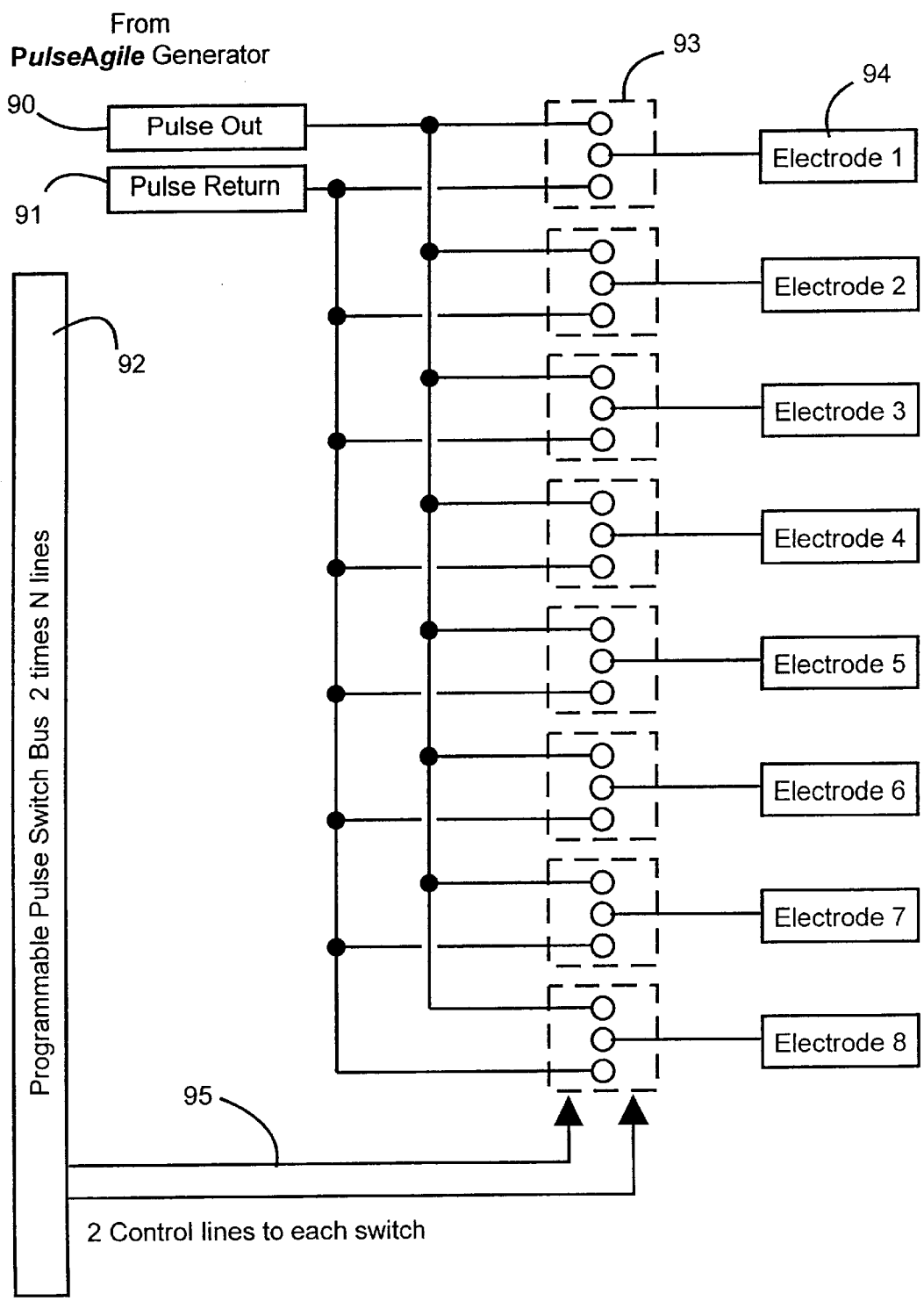
FIG. 4 is a block diagram, partially in schematic form, showing major components of the programmable pulse switches shown in FIG. 1.

The Programmable Pulse Switch 12 is connected to the PA-4000 by a high voltage cable 11 and parallel control cable 9. An overview is presented in FIG. 4. There are may be N switches 93 in the Programmable Pulse Switch, all of which operate identically. The high voltage pulse 90 and return 91 is provide via coaxial cable form the PA-4000 cabinet 5. Two control lines 95 one for selecting pulse out and one for selection pulse return. If the pulse out control line is high the pulse out will be connected to the electrode 94, If the pulse return control line is high the pulse return will be connected to the electrode 94. If neither is high nothing will be connected to the electrode 94, If both are high nothing is connected to the electrode 94.

Figure 4A:
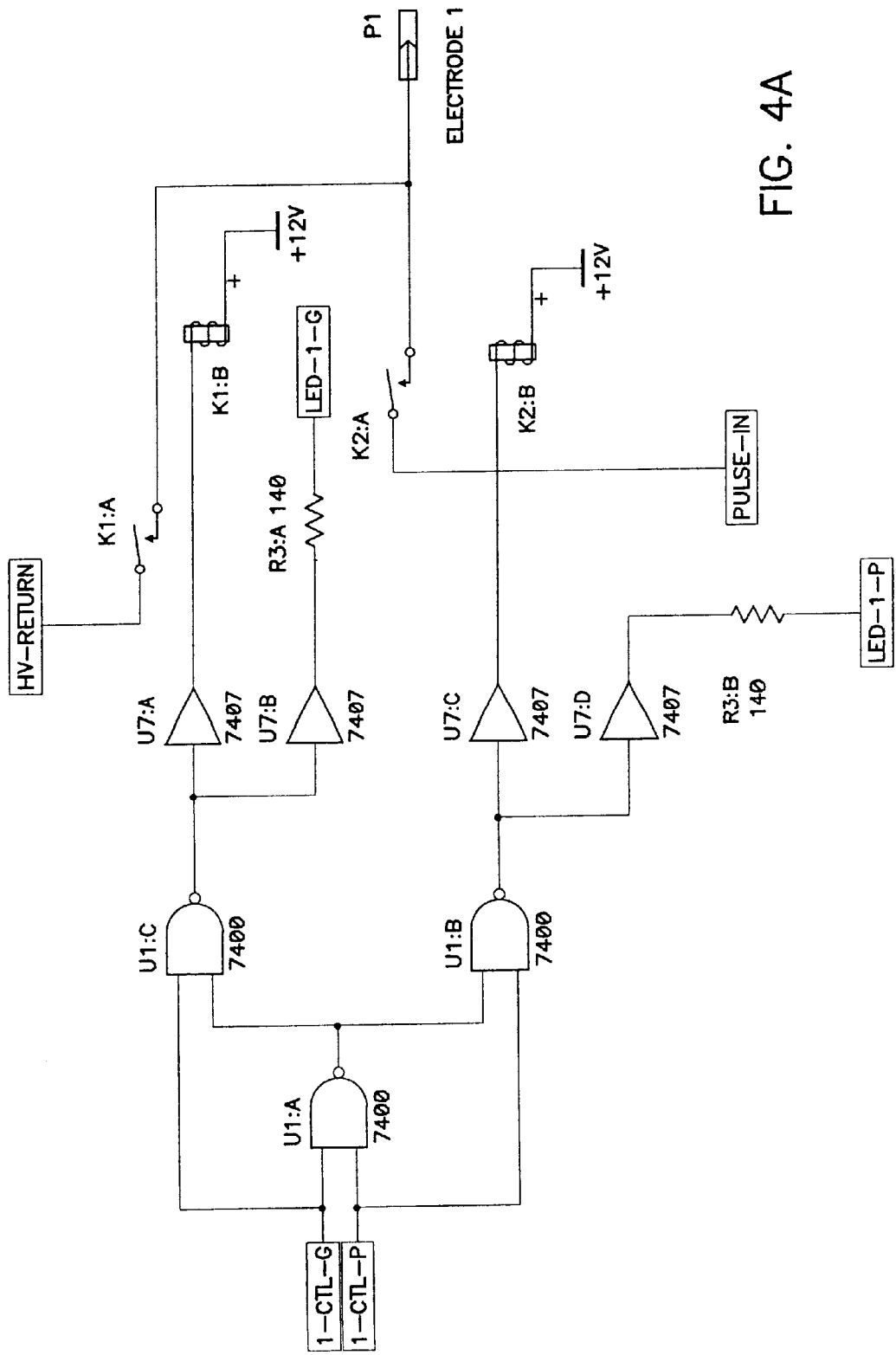
FIG. 4A is an electrical schematic diagram of one of the three-state switches shown in FIG. 4.

A detailed circuit diagram of the Three State Switch is present in FIG. 4A. Each switch has two inputs from the microprocessor, pulse return select, 161 and pulse out select 162, two inputs from the high voltage circuit, high voltage pulse, 164 and high voltage pulse return, 163, and one output port, 167 at which is connected to high voltage pulse, high voltage return or nothing at all depending on the command from the microprocessor. There are also two indicator output which are connected to light emitting diodes (LED), 166 (pulse), 165 (return) which indicate the state of the switch.

The high voltage pulse and high voltage return from the Agile Pulse generator are connected to all N switches.

There are two control line for each switch from the microprocessor, select pulse, 162 or select return, 161. If the select pulse control line goes high, the input to two NOR gates, U1A and U1B go high. U1A pin 2 is then high and pin two should be low causing pin 3 (out) to be high. The second NOR gates, U1B then has pin 4 high and pin 5 high which causes pin 6 (out) to be low. If pin 6 is low then the output of the non inverting, open collector driver U7C pin 6 is low. When this pin is low pin 16 on relay K2 is low energizing the relay coil and closing the relay K2. When this relay is closed the high voltage pulse in is connected to the output electrode. The second non-inverting driver is connected to a LED which is illuminated if the relay is energized, 166.

The same procured occurs if the microprocessor selects return. In that case relay K1 is closed connecting high voltage pulse return to the output port, 167.

If the microprocessor inadvertently sets both the high voltage pulse and high voltage pulse return lines high the NOR U1A output goes low and neither relay is energized. This is a safety feature to prevent the possibility of both relays being energized at the same time resulting is a short circuit.

There are then four possible conditions at the two lines from the microprocessor.

Pulse Select line high—pulse high voltage is then connected to the output port.

Pulse Return Select line high—Pulse return is then connected to the output port.

Neither line high—neither pulse or pulse return is connected to the output port.

Both lines high—neither pulse nor pulse return is connected to the output port.

In summary, all N switches are operated independently via the microprocessor and will present either a high voltage pulse, a high voltage return or nothing at all at the single output port of the switch.

Figure 5:
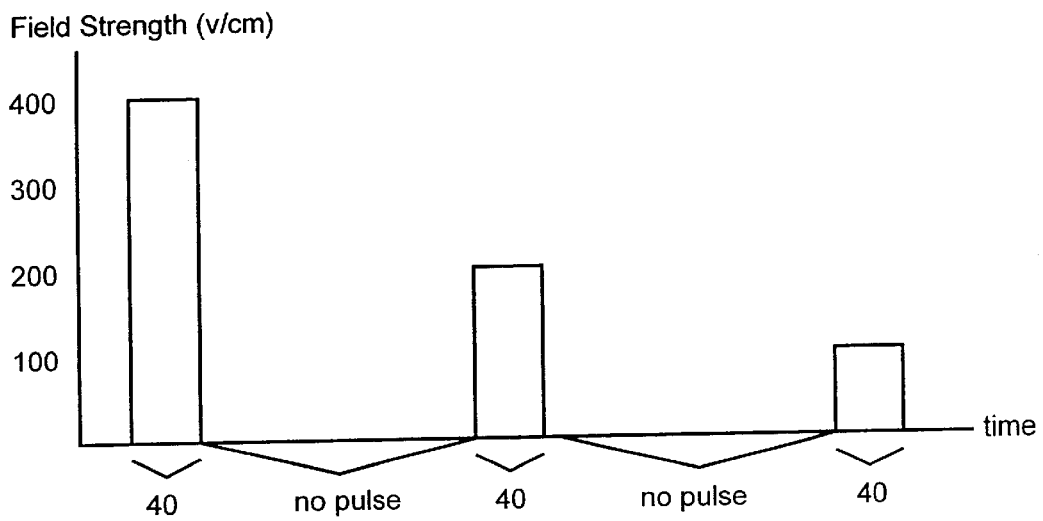
FIG. 5 illustrates non-sinusoidal pulses wherein at least two of the at least three pulses differ from each other in pulse amplitude.

FIG. 5 illustrates non-sinusoidal pulsed wherein at least two of the at least three pulses differ from each other in pulse amplitude.

Figure 6:
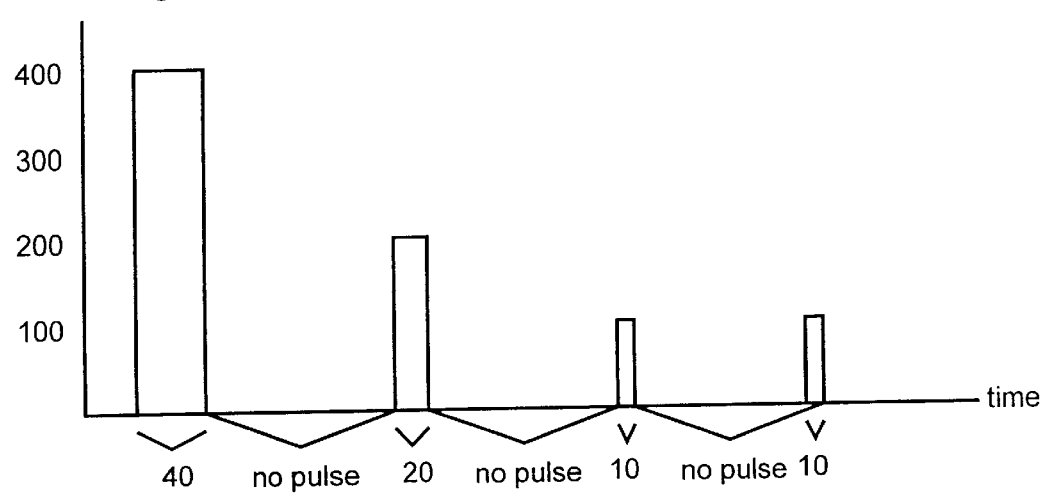
FIG. 6 illustrates non-sinusoidal pulses wherein at least two of the at least three pulses differ from each other in pulse width. It is noted that FIG. 6 also corresponds with Group A in Table I hereinbelow.

FIG. 6 illustrates non-sinusoidal pulsed wherein at least two of the at least three pulses differ from each other in pulse width. It is noted that FIG. 6 also corresponds with Group A in Table I hereinbelow.

Figure 7:
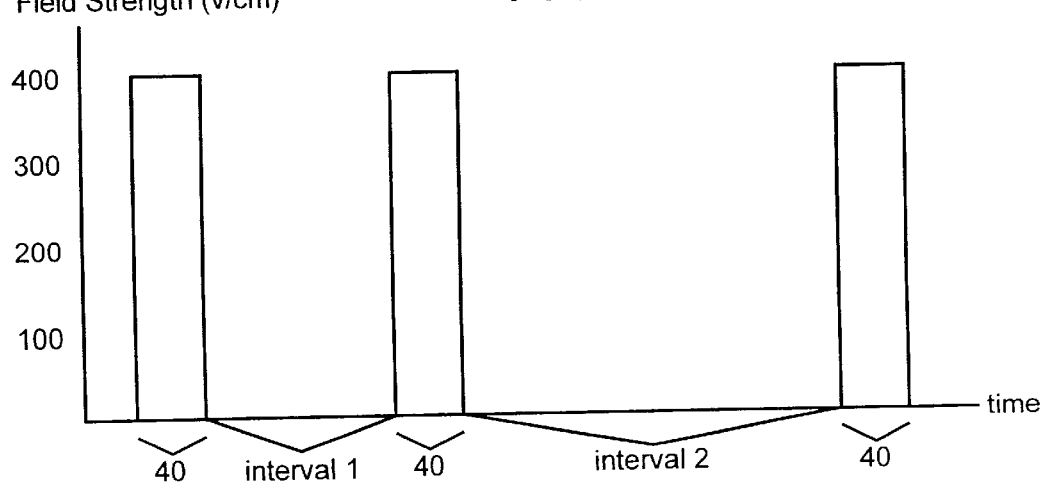
FIG. 7 illustrates non-sinusoidal pulses wherein a first pulse interval for a first set of two of the at least three pulses is different from a second pulse interval for a second set of two of the at least three pulses.

FIG. 7 illustrates non-sinusoidal pulses wherein a first pulse interval for a first set of two of the at least three pulses is different from a second pulse interval for a second set of two of the at least three pulses.

It is noted that the following terms herein are substantially synonymous: pulse selector apparatus; electrode selection apparatus 110; and Programmable Pulse Switch Cabinet 12.

The electrode selection apparatus 110 is manufactured and sold as a PA-101 of Cyto Pulse Sciences, Inc., Columbia, Md., which is the same company that manufactures and sells the Model PA-4000 Electroporation System described herein). The PA-101 is externally mounted and may be purchased separately from the high voltage agile pulse sequence generator. The PA-101 includes a set of eight computer-controlled HV switches which can connect any electrode to high voltage pulse, ground reference, or "float" the electrode (disconnected from any reference). The electrode selection apparatus is controlled by the same PA-4000 control software which controls the PA-4000, described below. A DB-25 control cable connects the PA-101 to the PA-4000.

As stated above, Model PA-4000 PulseAgile(™) Electroporation System is manufactured and sold by Cyto Pulse Sciences, Inc. of Columbia, Md. The Model PA-4000 system runs all standard square wave and many CD protocols. The Model PA-4000 system also runs advanced PulseAgile™ protocols. The Model PA-4000 PulseAgile(™) Electroporator accomplishes a wide range of electroporation tasks, many of which are not possible with existing equipment presently available. This system permits researchers to use standard protocols and has the increased flexibility of changing pulse parameters within a protocol. More tools are available for optimization. The system provides very fine control of the high fidelity pulsed electric fields to electroporate a wide variety of materials including plant cells, mammalian cells, and bacterial cells in aqueous solution and tissue.

Figure 8:
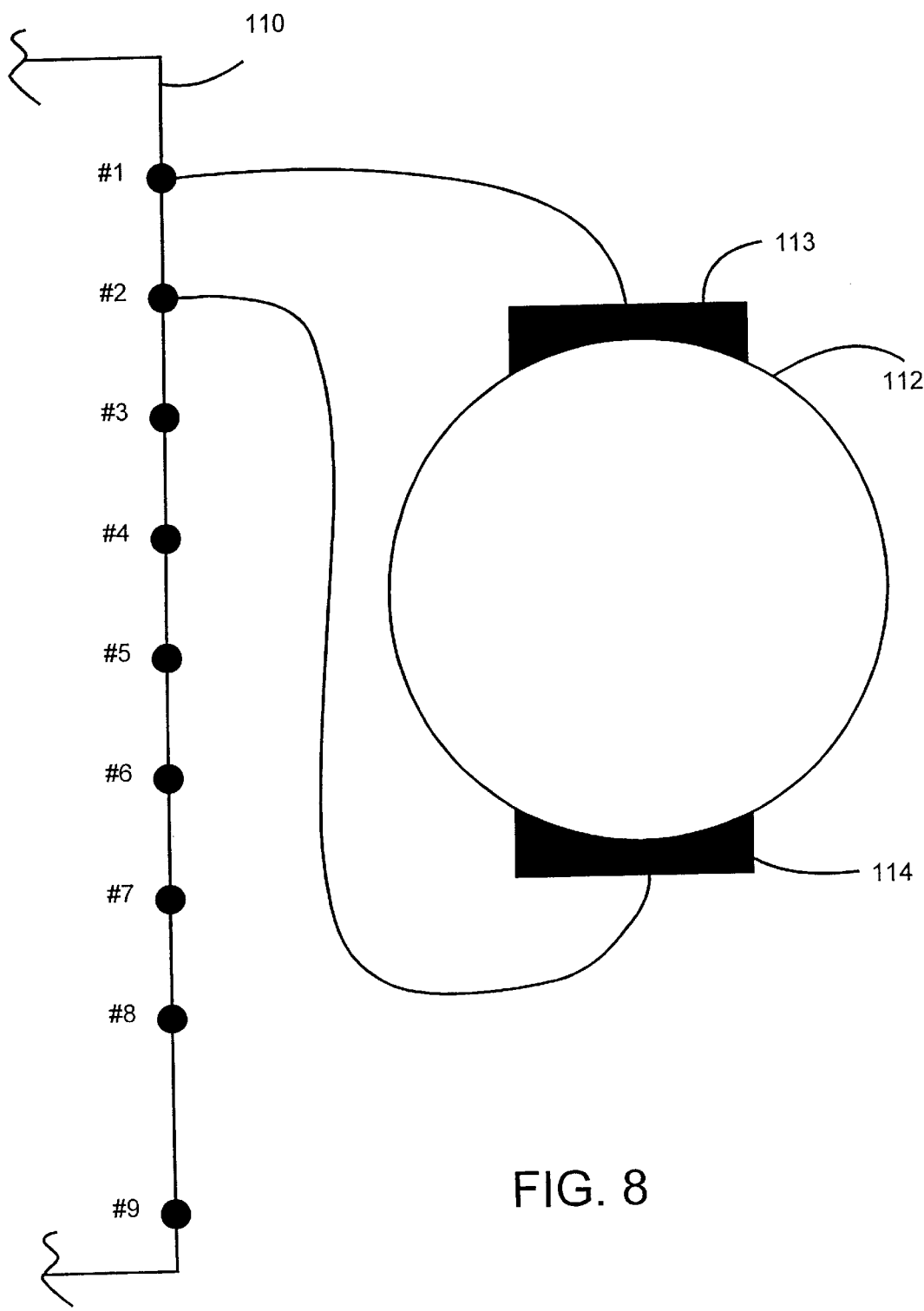
FIG. 8 illustrates a single cuvette equipped with two electrodes connected to an electrode selection apparatus of the invention.

Turning to FIG. 8, this figure illustrates a single cuvette 112 equipped with two electrodes 113, 114. One electrode 113 is connected to Terminal No. 1 of the electrode selection apparatus 110. The second electrode 114 is connected to Terminal No. 2 of the electrode selection apparatus 110. The electrode selection apparatus 110 can be programmed to sequentially reverse polarity of pulses applied to the two electrodes, whereby the direction of the electric field is reversed across the cuvette 113 for each polarity reversal. Polarity reversal can be carried out for each successive pulse, or, alternatively, for a predetermined pulse pattern.

Figure 9:
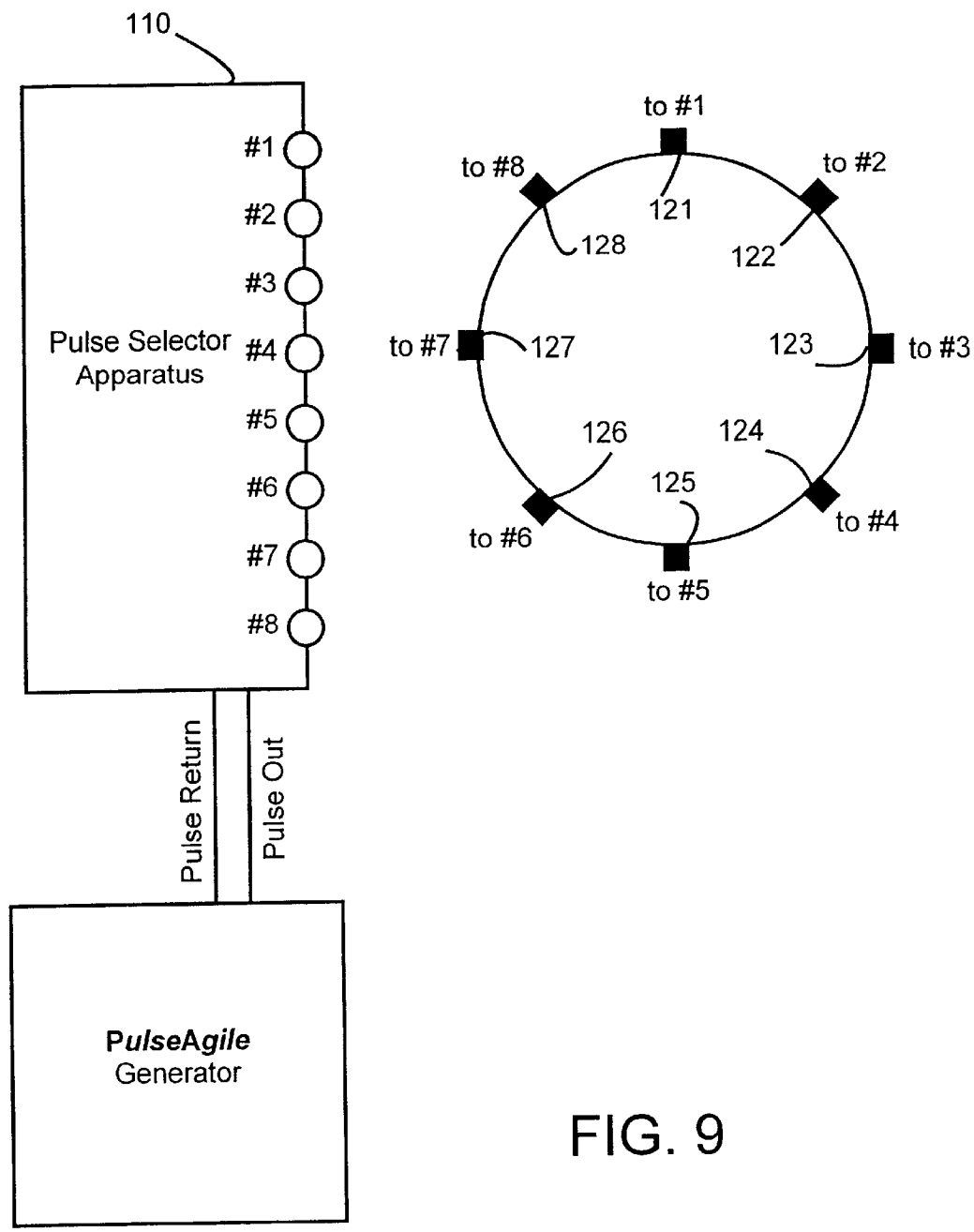
FIG. 9 illustrates a single cuvette equipped with eight electrodes distributed peripherally at different locations around the cuvette and connected to an electrode selection apparatus of the invention.

FIG. 9 illustrates a single cuvette 133 equipped with eight electrodes distributed peripherally at different locations around the cuvette. Electrode Nos. 121–128 are connected to Terminal Nos. 1–8, respectively, of the electrode selection apparatus 110. Positive/negative polarities can be applied first to Electrode Nos. 121 and 125, respectively. Then, positive/negative polarities can be applied to Electrode Nos. 122 and 126, respectively. Then, positive/negative polarities can be applied to Electrode Nos. 123 and 127, respectively. Then, positive/negative polarities can be applied to Electrode Nos. 124 and 128, respectively.

At this point, polarity reversals can be applied. That is, positive/negative polarities can be applied to Electrode Nos. 125 and 121, respectively. Then, positive/negative polarities can be applied to Electrode Nos. 126 and 122, respectively. Then, positive/negative polarities can be applied to Electrode Nos. 127 and 123, respectively. Then, positive/negative polarities can be applied to Electrode Nos. 128 and 124, respectively.

It is clear from the above, that this manner of applying pulses to Electrode Nos. 121–128 results in an electric field that rotates around and through the cuvette 133.

Such a cyclic pattern of positive/negative polarity application can be repeated as many times as desired.

FIG. 9 can also be thought of as illustrative of another application of the invention. The large circle can be representative of an in vivo organ, such as from an animal or plant. The Electrode Nos. 121–128 can be placed around the organ in three dimensions. Each of the electrodes is connected to a respective terminal on the electrode selection apparatus 110. The electrode selection apparatus 110 is connected to the high voltage agile pulse sequence generator 2. In this way, high voltage, non-sinusoidal agile pulses can be generated in the high voltage agile pulse sequence generator 2 and routed through the electrode selection apparatus 110 to the selected Electrode Nos. 121–128. Substantially any desired agile pulse sequence from the high voltage agile pulse sequence generator 2 can be routed to any desired subset of Electrode Nos. 121–128 in any desired programmable sequence.

FIGS. 10A–10F illustrate a first exemplary pattern of moving electric fields through the single cuvette wherein a two-pole electric field is rotated through the cuvette.

FIGS. 11A–11F illustrate a second exemplary pattern of moving electric fields through the single cuvette wherein a four-pole electric field is rotated through the cuvette.

Figures 12A, 12B, 12C:
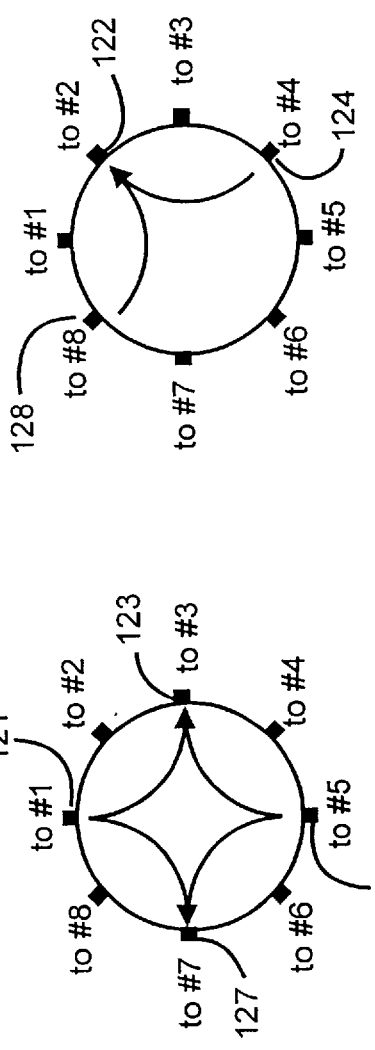
FIGS. 12A–12C illustrate a third exemplary pattern of moving electric fields through the single cuvette wherein the electric field changes from a four-pole field to a three-pole field to a five-pole field.

FIGS. 12A–12C illustrate a third exemplary pattern of moving electric fields through the single cuvette wherein the electric field changes from a four-pole field to a three-pole field to a five-pole field.

From just the few examples indicated above, it is clear that a very large number of patterns of electrical field distribution can be applied through the cuvette by changing the permutations and combinations of electrodes that are selected by the electrode selection apparatus in association with pulses that are provided by the agile pulse sequence generator to the electrode selection apparatus 110.

More specifically, with the electrode selection apparatus 110 of invention, to permit it to have such enormous flexibilty in electric field distribution either in vivo or in vitro, at least one of the selected electrodes serves as a pulse-receiving electrode, and at least one of the selected electrodes serves as a pulse-returning electrode. Moreover, any electrode, in any combination of electrodes, must function as either a pulse-receiving electrode, a pulse-returning electrode, or an non-pulse-conveying electrode.

Generally, N applied pulses can be routed to N groups of electrodes in sequence. Furthermore, successive groups of electrodes in the N groups of electrodes can be comprised of different individual electrodes. Alternatively, successive groups of electrodes in the N groups of electrodes can be comprised of the same individual electrodes.

Figure 13:
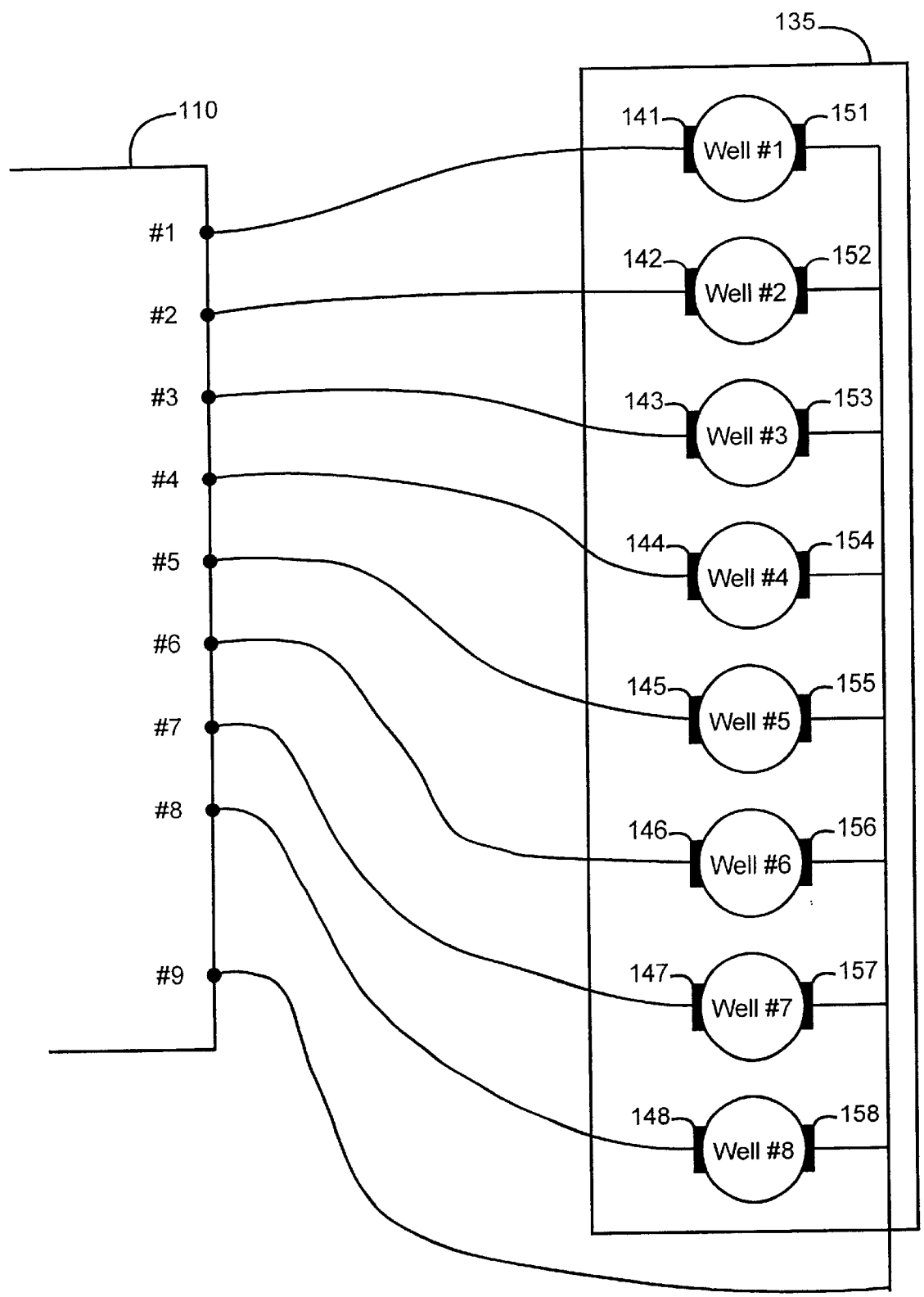
FIG. 13 illustrates a test plate that has eight test wells, each of which has an electrode connected to a respective terminal on the electrode selection apparatus.

In FIG. 13, a test plate 135 is illustrated that has Test Well Nos. 1–8. Each test well has a respective first electrode 141–148 connected to a respective Terminal No. 1–8 on the electrode selection apparatus 110. Each test well also has a respective second electrode 151–158 connected to Return Terminal No. 9 on the electrode selection apparatus 110. Each test well can be pulsed in a desired way either different from or the same as other test wells.

Turning to results obtained by employing the above-described apparatus for carrying out one aspect of the method of electroporation of the invention, Table I set forth herein is a tabulation of results of experiments which compare employing principles of the invention and employing conventional principles for carrying out electroporation. In carrying out the experiments tabulated in Table I, specific details relating to the following topics were taken into consideration: cells employed; electroporation conditions; determination of percent of cells porated; and determination of cells surviving electroporation. Details relating to these topics follow.

Cells. CHO—K1 cells (ATCC) were maintained in complete medium ($CO_2$ Independent medium (Gibco) plus 10% heat inactivated fetal calf serum, 2 mM L-glutamine, 100 units/ml penicillin, 100 μg/ml streptomycin and 0.25 μg/ml amphotericin B). Cells were grown in flat bottom T-150 flasks. For suspension cultures, cells were scrapped from T-150 flasks with a cell scraper. The cell suspension was added to a 100 ml spinner flask. Complete medium was added to make a total volume of 100 ml. Spinner flasks were maintained at 37° C. with a stir speed of 80 rpm. Spinner cultures were fed by removing 90% of the cell suspension and replacing the volume with complete medium. For the electroporation, 50 ml of cell suspension was removed from a log phase spinner culture. The cells were counted manually using a hemocytometer. The cells were centrifuged at 400× g for 10 minutes. The cells were re-suspended in serum free medium ($CO_2$ Independent medium without supplements) at a concentration of 5 million cells per ml.

Electroporation. A cell suspension volume of 250 μl was added to a sterile, disposable electroporation cuvette (Bio-Rad) with a 2 mm electrode gap. If indicated, 50 μl of either 1% Trypan blue solution (Sigma) or a solution containing 10 μg of plasmid DNA was added to the cuvette. The cuvette was added to a homemade cuvette holder. The pulser and computer control for the electroporation were those described in this patent. The pulser was turned on and the voltage was set. The pulse train was programmed-into the attached lap top computer and the pulse train executed by computer control.

Determination of percent of cells porated. Fifty microliters of 1% Trypan blue dye solution (2.4 gm of 44% trypan blue dye added to 100 ml distilled water) was added to the 250 μl of cell suspension in the electroporation cuvette. Before applying the high voltage pulses, a 10 μl sample was taken to determine the percent of cells that take up dye (dead cells) prior to electroporation. The pulses were applied to the cells as programmed. After electroporation, a 10 μl sample was taken to determine the percent of cells electroporated. The cells were counted manually on a hemocytometer. Blue cells were counted as positive and clear cells negative. Actual electroporation was calculated by subtracting background from both positive and negative counts.

Determination of cells surviving electroporation. Cells surviving electroporation were determined by the percent of cells able to attach to a tissue culture plate. A 24 well plate was prepared for the assay by adding 1 ml of complete medium to each well. Cells were added to the electroporation cuvette as described. A 10 μl (20 μl in some experiments) sample of cells was removed from the cuvette and placed into a well of the 24 well plate. Cells were rocked to evenly spread them across the plate. After the pulse session was applied, an equal sample was taken from the cuvette and placed into a different, adjacent well of the 24 well plate. Cells were cultured overnight at 37° C. The next day, cells were washed in PBS and fixed in 10% buffered formalin for 1 hour. Cells were washed with PBS then distilled water. Cells were stained with 1% Crystal Violet in distilled water by adding 400 μl dye to each well. The cells were incubated for 5 min then washed with distilled water until no dye was eluted from the plate. The cells were air dried until reading of the plate. One ml of 70% alcohol was added to each well and incubated for 5 min. The optical density of the alcohol-dye mixture was measured at 592 nM with an alcohol blank. Percent live cells was calculated as OD of sample after electroporation divided by OD of the sample before electroporation.

TABLE I

Comparison of percent poration and percent of cells surviving poration. In accordance with the invention, multiple sets of pulses having a 10 μs pulse width and having a 400 volt pulse amplitude were preceded by longer duration single pulses of either 40 μs plus 20 μs (for Group A) or 20 μs alone (for Group B). A prior art set of pulses is provided by Group C.

| Number of 10 μs Pulses[1,2] | | |
|---|---|---|
| Group A[3] | | |
| | % porated | % live |
| 0 | 25.51 | 81.98 |
| 1 | 55.62 | 87.91 |
| 2 | 55.62 | 86.94 |
| 4 | 81.51 | 85.84 |
| 8 | 88.29 | 95.14 |
| 16 | 96.31 | 76.99 |
| Group B[4] | | |
| | % por. | % live |
| 0 | 16.45 | 90.97 |
| 1 | 15.72 | 99.45 |
| 2 | 12.11 | 92.11 |
| 4 | 29.88 | 88.46 |
| 8 | 85.08 | 94.34 |
| 16 | 98 | 80.01 |
| Group C[5] (PRIOR ART) | | |
| | % por. | % live |
| 0 | ND | ND |
| 1 | 5.25 | 94.05 |
| 2 | 12.03 | 87.75 |
| 4 | 28.48 | 77.2 |
| 8 | 70.52 | 77.36 |
| 16 | 83.96 | 70.59 |

[1]All pulse voltages were 400 volts.
[2]Pulse intervals were 0.1 second.
[3]Group A. In accordance with the invention, pulse trains of 10 μ seconds were preceded by a single pulse of 40 μs and a single pulse of 20 μs.
[4]Group B. In accordance with the invention, pulse trains of 10 μs were preceded by a single pulse of 20 μs.
[5]Group C. As presented in the prior art, pulse trains of 10 μs were delivered without preceding pulses.

In interpreting the results of the experiments tabulated in Table I, it is recalled that Group C data represent a prior art pulse train of pulses having a constant pulse amplitude of 400 volts, having a constant pulse interval of 0.1 seconds, and having a constant pulse width of 10 microsecs.

The data for Group A, with the exception of "0" additional microsecond pulses, represent a pulse train in accordance with the invention in which pulses have three different pulse widths. For the pulses for Group A, the pulses have a constant pulse amplitude and a constant pulse interval.

The data for Group B, with the exception of "0" additional microsecond pulses, represent a pulse train in accordance with the invention in which pulses have two different pulse widths. For the pulse for Group B, the pulses have a constant pulse amplitude and a constant pulse interval.

It is noted that, generally, the larger the number of pulses, the larger the percentage of porated cells. This is true for both the prior art pulse train (Group C) and the two pulse trains of the invention (Groups A and B). The maximum percent poration for the prior art pulse train is 83.96%. However, in sharp contrast, the maximum percent poration for Group A pulse trains of the invention is 96.31%. The maximum percent poration for Group B pulse trains of the invention is 98%. Clearly, with the invention, the percent poration exceeds the prior art percent poration.

With respect to viability, the average percent live for Group C is 81.39%. The average percent live for Group A, excluding the data from "0" additional 10 microsecond pulses, is 86.56%. The average percent live for Group B, excluding the data from "0" additional 10 microsecond pulses, is 90.87%. Clearly, the average percent viability for the data which are encompassed by the method of the invention in both Group A and Group B exceed the average percent viability for the prior art data in Group C.

To derive further meaning from the data present in Table I, Table II has been prepared. Table II relates to the fact that success in electroporation depends upon both the number of cells that are porated and the number of cells that remain alive. In Table II, for each group of data, a product has been obtained by multiplying the value of % porated by its corresponding value of % live. Such products provide a composite number that represents both the number of porated cells and the number of cells which survive the electroporation process. Such a composite number is more representative of the efficacy of electroporation that either % poration or % live alone.

TABLE II

For each of the data in Groups A, B, and C, respectively, in Table I, multiply % porated × % live. This product gives a composite figure for the overall electroporation efficiency taking into account both the extent of poration and the viability of the cells.

| Number of 10 μs Pulses | Group A (% porated × % live) | Group B (% porated × % live) | Group C (% porated × % live) |
|---|---|---|---|
| 0 | 2091 | 1493 | — |
| 1 | 3218 | 1563 | 494 |
| 2 | 4836 | 1115 | 1056 |
| 4 | 6997 | 2643 | 2199 |
| 8 | 8400 | 8026 | 5455 |
| 16 | 7415 | 7841 | 5927 |

Clearly, the products for each of Groups A and B (the invention) exceed the corresponding product for Group C (prior art). Clearly, then, the overall electroporation efficiency, taking into account both the extent of poration and the viability of the cells, is greater with pulse trains of the invention than with the prior art.

It is apparent from the above that the present invention accomplishes all of the objects set forth by providing a method of treating materials with pulsed electrical fields provides a process for application of a series of electrical pulses to living cells wherein the electrical pulses produce reduced cell lethality. With the invention, a method of treating materials with pulsed electrical fields provides an operator of electrical pulse equipment a process for maximum operator control of an applied pulse series. With the invention, a method of treating materials with pulsed electrical fields is provided which provide a process for changing pulse width during a series of electrical pulses. With the invention, a method of treating materials with pulsed electrical fields is provided which provide a process for changing pulse voltage during a series of electrical pulses. With the invention, a method of treating materials with pulsed electrical fields provides a machine for control of the process. With the invention, a method of treating materials with pulsed electrical fields provides a pulse protocol that sustains induced pores formed in electroporation. With the invention, a method of treating materials with pulsed electrical fields provides a pulse protocol which provides three or more pulses to allow more time for materials to enter cells undergoing electroporation. With the invention, a method of treating materials with pulsed electrical fields provides an electrical way to improve cell survival and transfection efficiency. With the invention, a method of treating materials with pulsed electrical fields provides a method of electroporation in which maximum transformation efficiency is achieved when greater than 40% of cells survive the pulse effecting electroporation.

While the present invention has been described in connection with the drawings and fully described above with particularity and detail in connection with what is presently deemed to be the most practical and preferred embodiments of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed is:

1. A method of treating membrane-containing material in vitro with electrical fields, comprising the steps of:
    arranging the in vitro material in an array of locations,
    arranging a plurality of electrodes in an array of locations corresponding to the array of in vitro material locations,
    connecting the electrodes to outputs of an electrode selection apparatus,
    connecting inputs of the electrode selection apparatus to outputs of an electrical pulser apparatus,
    applying electrical pulses to the electrode selection apparatus, and
    routing applied pulses through the electrode selection apparatus in a predetermined sequence to selected electrodes in the array of electrodes, whereby the in vitro material in the array of locations is treated with electrical fields of sequentially varying directions in the array of locations.

2. The method of claim 1 wherein at least one of the selected electrodes serves as a pulse-receiving electrode and wherein at least one of the selected electrodes serves as a pulse-returning electrode.

3. The method of claim 2 wherein any electrode, in any combination of electrodes, must be either a pulse-receiving electrode, a pulse-returning electrode, or a non-pulse-conveying electrode.

4. The method of claim 1 wherein N applied pulses are routed to N groups of electrodes in sequence.

5. The method of claim 4 wherein successive groups of electrodes in the N groups of electrodes are comprised of different individual electrodes.

6. The method of claim 4 wherein successive groups of electrodes in the N groups of electrodes are comprised of the same individual electrodes.

7. The method of claim 1 wherein at least two successive pulses applied to a selected electrode are reversed in electric field direction.

8. The method of claim 1 wherein the electrodes are arrayed as M pairs of electrodes associated with M wells in a testing plate.

9. The method of claim 1 wherein the electrodes are arrayed as a pair of electrodes associated with a cuvette.

10. The method of claim 1 wherein the electrodes are arrayed as P electrodes associated with a cuvette, wherein P is greater than two.

* * * * *